(12) United States Patent
Clarkson et al.

(10) Patent No.: US 7,314,743 B2
(45) Date of Patent: Jan. 1, 2008

(54) MODIFIED ENZYMES, METHODS TO PRODUCE MODIFIED ENZYMES AND USE THEREOF

(75) Inventors: Kathleen A. Clarkson, Palo Alto, CA (US); Fred Fenel, Helsinki (FI)

(73) Assignee: Genencor International, Palo Alto, CA (US)

( * ) Notice: Subject to any disclaimer, the term of this patent is extended or adjusted under 35 U.S.C. 154(b) by 0 days.

(21) Appl. No.: 10/565,954

(22) PCT Filed: Sep. 10, 2004

(86) PCT No.: PCT/US2004/029575

§ 371 (c)(1),
(2), (4) Date: Jul. 31, 2006

(87) PCT Pub. No.: WO2005/108565

PCT Pub. Date: Nov. 17, 2005

(65) Prior Publication Data

US 2006/0270006 A1    Nov. 30, 2006

Related U.S. Application Data

(60) Provisional application No. 60/503,251, filed on Sep. 15, 2003.

(51) Int. Cl.
| | |
|---|---|
| C12N 9/24 | (2006.01) |
| C12N 1/20 | (2006.01) |
| C12N 15/75 | (2006.01) |
| C12P 19/04 | (2006.01) |
| C12P 21/06 | (2006.01) |
| C07H 21/04 | (2006.01) |
| C08B 1/00 | (2006.01) |

(52) U.S. Cl. ............... 435/200; 435/101; 435/252.3; 435/69.1; 435/471; 536/23.2; 536/56

(58) Field of Classification Search ........... 435/200, 435/101, 252.3, 69.1, 471; 536/23.2, 56
See application file for complete search history.

(56) References Cited

U.S. PATENT DOCUMENTS

| | | | |
|---|---|---|---|
| 4,683,202 A | 7/1987 | Mullis | |
| 5,736,384 A | 4/1998 | Fukunaga et al. | |
| 5,759,840 A | 6/1998 | Sung et al. | |

FOREIGN PATENT DOCUMENTS

| | | | |
|---|---|---|---|
| EP | 1 131 447 B1 | 11/1999 | |
| WO | WO01/27252 A1 | * 4/2001 | |

OTHER PUBLICATIONS

Altschul et al., "Basic local alignment search tool," *J. Mol Biol.*, Oct. 5, 1990, 215(3):403-410.
Arase et al., "Stabilization of xylanase by random mutagenesis," *FEBS Lett*. V316:2, 123-127 (1993).
Bailey et al., "Interlaboratory testing of methods for assay of xylanase activity," *J. Biotechnol*, 23 257-270, (1992).
Beucage S.L. et al., (1981) *Tetrahedron Letters* 22, p. 1859-1869.
Biely, P et al., "Soluble Chromogenic Substrates for the Assay of Endo-1,4-β-xylanases and Endo-1,4-β-glucanases," *Analytical Biochemistry*, 144, 142-146 (1985).
Bodie et al., 1995—should be 1994, Strain improvement of chymosin-producing strains of *Aspergillus niger* var. *awamori* using parasexual recombination, *Encymae Microb. Technol.*, 1994, V. 16, pp. 376-382.
Bodie et al., 1995—should be 1994, Economically Important Organic Acid and Enzyme Products, Chapter 22, pp. 561-602, *Progress in Industrial Microbiology*, 29(*Aspergillus: 50 years on*).
Davies et al., "Structures and mechanisms of glycosyl hydrolases," *Structure*, 1995, 3(9):853-9.
Devereux et al., "Acomprehensive set of sequence analysis programs for the VAX," *Nuc. Acids Research*, V12:1, pp. 387-395 (1984).
Harris et al.., "Structural basis of the properties of an industrially relevant thermophilic xylanase," *Proteins*, 29, 77-86 (1997).
Henrissat, B. and Bairoch, A., "New families in the classification of glycosyl hydrolases based on amino acid sequence similarities," *Biochem. J.*, 293 781-8 (1993).
Henrissat, B. and Davies, G., "Structural and sequence-based classification of glycoside hydrolases," *Curr. Opin. Struct.* Biol. 7 637-44 (1997).
Higgins DG & Sharp PM, "Clustal: a package for performing multiple sequence alignment on a microcomputer," *Gene* 73(1), 237-244) (1988).
Livingstone et al., "Protein sequence alignments: a strategy for the hierarchial analysis of residue conservation," *Comput.Appl Biosci.*, V9:6, 745-756 (1993).
Matthes et al., "Simultaneous apid chemical synthesis of over one hundred oligonucleotides on a microscale," *EMBO J.*, V3:4, p. 801-805, (1984).
Morinaga et al., "Improvement of Oligonucleotide-Directed Site-Specific Mutagenesis using double-stranded plasmid DNA," *Biotechnology* (1984) 2, p. 646-649.
Nelson and Long , "A General Method of Site-Specific Mutagenesis Using a Modificxation of the Thermus acquaticus Polymerase Chain Reaction," *Analytical Biochemistry* V180, p. 147-151), (1989).
Nielsen et al., "Identification of prokaryotic and eukaryotic signal peptides and prediction of their cleavage sites," *Protein Eng.* 1997 10:1 pp. 1-6.
Prade, R.A., "Xylanases: from biology to biotechnology," *Biotechnol. Genet. Eng. Rev.*, 13, 101-131 (1996).
Saiki R K et al. "Primer-Directed Enzymatic Amplification of DNA with a Thermostable DNA Polymerase," *Science*, V239, pp. 487-491, (1988).

(Continued)

Primary Examiner—Rebecca S. Prouty
Assistant Examiner—Iqbal Chowdhury
(74) Attorney, Agent, or Firm—Jennifer A. Haynes

(57) ABSTRACT

The invention is directed to modified xylanases having increased stability in harsh industrial environments, such as increased pH and/or temperature.

13 Claims, 21 Drawing Sheets

OTHER PUBLICATIONS

Sandgren et. al., " The x-ray Crystal Structure of the *Trichoderma reesei* Family 12 Endoglycanase 3, Cell2A, at 1.9 A Resolution ," *J. Mol. Bio.* (2001) 308, 295-310.

Sarkar and Sommer, "The "Megaprimer" Method of Site-Directed Mutagenesis," (*Biotechniques* (1990), V8:4, pp. 404-407.

Stirk et al., "Depicting topology and handedness in jellyroll structures," *FEBS Lett.* Aug. 10, 1992, 308(1):1-3.

Tatusova et al., "Blast 2 Sequences, a new tool for comparing protein and nucleotide sequences," *FEMS Microbiol Lett*, 174 (2): 247-50, (1999).

Tatusova, T. et al., "Erratum to Blast 2 Sequences, a new tool for comparing protein and nucleotide sequences," *FEMS Microbiol Lett*, V177: 187-188, (1999).

Taylor W.R., "The Classification of Amino Acid Conservation," (1986) *J.Theor.Biol.* 119; 205-218.

Tenkanen et al., "Two major xylanases of *Trichoderma reesei*," *Enzyme Microb. Technol,.* 14 566-574 (1992).

Törrönen, A. and Rouvinen, J., "Structural comparison of two major endo-1,4-xylanases from *Trichoderma reesei*," *Biochemistry* 34 847-56, (1995).

Törrönen, A. and Rouvinen, J., "Structural and functional properties of low molecular weight endo-1,4-beta-xylanases," *J. Biotechnol.*, 57 137-149 (1997).

Vogt et al., "Protein thermal stability, hydrogen bonds, and ion pairs," *J. Mol. Biol.*, 269 631-43 (1997).

Wakarchuk et al., "Thermostabilization of the *Bacillus circulans* xylanase by the introduction of disulfide bonds," *Protein Eng.*, 7:11, 1379-86 (1994).

* cited by examiner

Figure 1

```
                     10        20        30        40        50
                      |         |         |         |         |
XYN2_TRIRE   ---MVSFTSLLAASPP-SRASCRPAAEV---ESVAVEKRQTIQ------P
XYN1_HUMIN   ---MVSLKSVLAAATAVSSAIAAPFDFVPRDNSTALQARQVTP------N
XYNA_BACST   ---------------------MKLKKKMLTLLLTASMSFGLF------G
XYN1_TRIRE   ---MVAFSSLICALTSIASTLAMPTGLEPESSVNVTERGMYDFVLGAHND
XYN1_ASPAW   --------------MKVTAAFAGLLVTAFAAPVPEPVLVS---------
XYN2_BACST   MCSSIPSLREVFANDFRIGAAVNPVTLEAQQSLLIRHVNSLTAENHMKFE 60        70        80        90       100
                      |         |         |         |         |
XYN2_TRIRE   GTGYNNGYFYSYWNDGHGGVTYTNGPGGQFSVNWS--NSG-NFVGGKGWQ
XYN1_HUMIN   AEGWHNGYFYSWWSDGGGQVQYTNLEGSRYQVRWR--NTG-NFVGGKGWN
XYNA_BACST   ATSSAATDYWQYWTDGGGMVNAVNGPGGNYSVTWQ--NTG-NFVVGKGWT
XYN1_TRIRE   HRRRASINYDQNYQTG-GQVSYSPSNTG-FSVNWN--TQD-DFVVGVGWT
XYN1_ASPAW   --RSAGINYVQNYNGNLGDFTYDESAGT-FSMYWEDGVSS-DFVVGLGWT
XYN2_BACST   HLQPEEGRFTFDIAIKSSTSPFSSHGVRGHTLVWHNQTPSWVFQDSQGHF 110       120       130       140       150
                      |         |         |         |         |
XYN2_TRIRE   PGTKNKVINFS-GSYNPNGNSYLSVYGWSRNPLIEYYIVENF---GTYNP
XYN1_HUMIN   PGT-GRTINYG-GYFNPQGNGYLAVYGWTRNPLVEYYVIESY---GTYNP
XYNA_BACST   VGSPNRVINYNAGIWEPSGNGYLTLYGWTRNALIEYYVVDSW---GTYRP
XYN1_TRIRE   TGS-SAPINFGGSFSVNSGTGLLSVYGWSTNPLVEYYIMED-----NHNY
XYN1_ASPAW   TGS-SNAITYSAEYSASGSSSYLAVYGWVNYPQAEYYIVEDY---GDYNP
XYN2_BACST   VGRDVLLERMKSHISTVVQRYKGKVYCWDVINEAVADEGSEWLRSSTWRQ 160       170       180       190       200
                      |         |         |         |         |
XYN2_TRIRE   STGATKLGEVTSDGSVYDIYRTQRVNQPSIIGTATFYQYWSVRRNHRSSG
XYN1_HUMIN   GSQAQYKGTFYTDGDQYDIFVSTRYNQPSIDGTRTFQQYWSIRKNKRVGG
XYNA_BACST   T--GNYKGTVNSDGGTYDIYTTMRYNAPSIDGTQTFQQFWSVRQSKRPTG
XYN1_TRIRE   PAQGTVKGTVTSDGATYTIWENTRVNEPSIQGTATFNQYISVRNSPRTSG
XYN1_ASPAW   CSSATSLGTVYSDGSTYQVCTDTRTNEPSITGTSTFTQYFSVRESTRTSG
XYN2_BACST   IIGDDFIQQAFLYAHEADPEALLFYNDYNECFPEKREKIYTLVKSLRDKG
Figure 1

210       220       230       240       250
                      |         |         |         |         |
XYN2_TRIRE   S----VNTANHFNAWA-QQGLTLGTMD-YQIVAVEGYFSSGSASITVS--
XYN1_HUMIN   S----VNMQNHFNAWQ-QHGMPLGQHY-YQVVATEGYQSSGESDIYVQTH
XYNA_BACST   SNV-SITFSNHVNAWR-SKGMNLGSSWAYQVLATEGYQSSGRSNVTVW--
XYN1_TRIRE   T----VTVQNHFNAWA-SLGLHLGQMN-YQVVAVEGWGGSGSASQSVSN-
XYN1_ASPAW   T----VTVANHFNFWA-QHGFGNSDFN-YQVMAVEAWSGAGSASVTISS-
XYN2_BACST   IPIHGIGMQAHWSLNRPTLDEIRAAIERYASLGVILHITELDISMFEFDD 260       270       280       290       300
                      |         |         |         |         |
XYN2_TRIRE   --------------------------------------------------
```

Figure 1 (continued)

```
XYN1_HUMIN   ------------------------------------------------
XYNA_BACST   ------------------------------------------------
XYN1_TRIRE   ------------------------------------------------
XYN1_ASPAW   ------------------------------------------------
XYN2_BACST   HRKDLAAPTNEMVERQAERYSQIFSLFKEYRDVIQNVTFWGIADDHTWLD
```

```
                   310       320       330
                    |         |         |
XYN2_TRIRE   ---------------------------------
XYN1_HUMIN   ---------------------------------
XYNA_BACST   ---------------------------------
XYN1_TRIRE   ---------------------------------
XYN1_ASPAW   ---------------------------------
XYN2_BACST   HFPVQGRKNWPLLFDEQHNPKPAFWRVVNI
```

Figure 3

| | |
|---|---|
| H22K | 5'- GAACGATGGC<u>AA</u>GGGCGGCGTGACG -3' |
| S65C | 5'- CTTCTCGGGC<u>TGC</u>TACAACCCAAACGG -3' |
| N92C | 5'- ACATCGTCGAG<u>TGT</u>TTGGCACCTAC -3' |
| F93W | 5'- CATCGTCGAGAAC<u>TGG</u>GGCACCTACAACC -3' |
| N97R | 5'- GGCACCTAC<u>CGA</u>CCGTCCACG -3' |
| V108H | 5'- CAAGCTGGGCGAG<u>CAC</u>ACCTCCGAC -3' |
| H144C | 5'- CGCCGCAAC<u>TGT</u>CGCTCGAGC -3' |
| F180Q | 5'- GTGGAGGGTTAC<u>CAA</u>AGCTCTGGCTCTGC -3' |
| S186C | 5'- TCTGGCTCTGCT<u>TGC</u>ATCACCGTCAGC -3' |
| T2C | 5'-GAGAAGCGCCAG<u>TGC</u>ATTCAGCCCGGC-3' |
| T28C | 5'-GTGACGTAC<u>TGC</u>AATGGTCCCGGCGGG-3' |
| K58R | 5'-GGCACCAAGAAC<u>AGG</u>GTCATCAACTTCTCGGGC-3' |
| I91D | 5'-TCCATCACCGTCAGC<u>GAT</u>TAAAGGGGGCTCTTC-3' |
| P5C | 5'-CCCAGACGATTCAGT<u>GC</u>GGCACGGGCTACAAC-3' |
| N19C | 5'-CTTCTACTCGTACTGG<u>TGC</u>GATGGCCACGGCG-3' |
| T7C | 5'-CGATTCAGCCCGGC<u>TGC</u>GGCTACAACAACGGC-3' |
| S16C | 5'-CAACGGCTACTTCTAC<u>TGC</u>TACTGGAACGATGGCC-3' |
| N10C | 5'-CCGGCACGGGCTAC<u>TGC</u>AACGGCTACTTCTACTC-3' |
| N29C | 5'-GGCGTGACGTACACC<u>TGC</u>GGTCCCGGCGGGC-3' |
| L105C | 5'-GGCGCCACCAAG<u>TGC</u>GGCGAGGTCACC-3' |
| Q162C | 5'-GCGTGGGCTCAG<u>TGC</u>GGCCTGACGCTCG-3' |

Figure 18

Trichoderma reesei Xyl II protein (high pI xylanase)
the full sequence, including signal and pro sequence MVSFTSLLAGVAAISGVLAAPAAEVESVAVEKRQTIQPGTGYNNGYFYSYWNDGHGGVTYTNGPGGQFSVNWSNSGNFVG
GKGWQPGTKNKVINFSGSYNPNGNSYLSVYGWSRNPLIEYYIVENFGTYNPSTGATKLGEVTSDGSVYDIYRTQRVNQPS
IIGTATFYQYWSVRRNHRSSGSVNTANHFNAWAQQGLTLGTMDYQIVAVEGYFSSGSASITVS (SEQ. ID NO: 1)

Trichoderma reesei XynII gene (high pI xylanase)
DNA from start codon to stop codon (includes a single intron)

ATGGTCTCCTTCACCTCCCTCCTCGCCGGCGTCGCCGCCATCTCGGGCGTCCTCGCCGCCCCGGCCGAGGTCGAATC
CGTGGCTGTGGAGAAGCGCCAGACGATTCAGCCCGGCACGGGCTACAACAACGGCTACTTCTACTCGTACTGGAACGATG
GCCACGGCGGCGTGACGTACACCAATGGTCCCGGGGGCCAGTTCTCCGTCAACTGGTCCAACAGCGGCAACTTTGTCGGC
GGCAAGGGATGGCAGCCCGGCACCAAGAACAAGGTAAGACTACTAAGACTGTGTTTTCAAAAAAAGGGTCATCAACTTCTCGGGC
AGCTACAACCCCAACGGCAACAGCTACCTCTCCGTGTACGGCTGGTCCCGCAACCCCCTGATCGAGTACTACATCGTCGA
GAACTTTGGCACCTACAACCCGTCCACCGGGGCCACCAAGCTGGGCGAGGTCACCTCCGACGGCAGCGTCTACGACATTT
ACCGCACGCAGCGCGTCAACCAGCCGTCCATCATCGGCACCGCCACCTTCTACCAGTACTGGTCCGTCCGCCGCAACCAC
CGCTCGAGCGGCTCCGTCAACACGGCGAACCACTTCAACGCGTGGGCTCAGCAAGGCCTGACGCTCGGGACGATGGATTA
CCAGATTGTTGCCGTGGAGGGTTACTTTAGCTCTGGCTCTGCTTCCATCACCGTCAGCTAA (SEQ. ID NO: 2)

Figure 19

Trichoderma reesei EGL III protein (endoglucanase III)
the full sequence, including signal sequence MKFLQVLPALIPAALAQTSCDQWATFTGNGYTVSNNLWGASAGSGFGCVTAVSLSGGASWHADWQWSGGQNNVKSYQNSQ
IAIPQKRTVNSISSMPTTASWSYSGSNIRANVAYDLFTAANPNHVTYSGDYELMIWLGKYGDIGPIGSSQGTVNVGGQSW
TLYYGYNGAMQVYSFVAQTNTTNYSGDVKNFFNYLRDNKGYNAAGQYVLSYQFGTEPFTGSGTLNVASWTASIN
(SEQ. ID NO: 3)

Trichoderma reesei EG III gene (endoglucanase III)
DNA from start codon to stop codon (includes two introns)

ATGAAGTTCCTTCTTCAAGTCCTCCCTGCCCTCATACCGGCCGCCCTGGCCCAAACCAGCTGTGACCAGTGGGCAACCTTCAC
TGGCAACGGCTACACAGTCAGCAACAACCTTTGGGGAGCATCAGCGGCTCTGGATTTGGCTGCGTGACGGCGGGTATCGC
TCAGCGGGCGGGGCCCTCCTGGCACGCCAGACTGGTCCGGCGGCCAGAACAACGTCAAGTCGTACCAGAACTCTCAG
ATTGCCATTCCCCAGAAGAGACCGTCAACAGCATCAGCAGCATGCCCACCACTGCCAGCTACAGGGGAGCAA
CATCCGCGCTAATGTTGCGTATGAAGAAGTGACCCTCCTTGATAGTTTCGACTAACAACATGTCTTGAGGCTTGGCAAATACGGCGA
TGATCTGGTAAGCCATAAGAAGTGACCCTCCTCACAGGAACAGTCAAGTCGGTGGCCAGAGTCTTGAGGCTCTACTATGGCTACAACGGAG
TATTGGGCGATTGGGTCCTCACAGGAACAGTCAACGTCGGTGGCCAGAGTCTTGAGAACTTCTTCAATTATCTC
CCATGCAAGTCTATTCCTTGTGGCCCAGACCAACACTACCAACACTATGTCTTAGTAAGTCACCCTCACTGTGACTGGGCTGAGTTTGTTG
CGAGACAATAAAGGATACAACGCTGCAGGCCAATATGTCTTAGTAAGTCACCCTCACTGTGACTGGGCTGAGTTTGTTG
CAACGTTTGCTAACAAAACCTTCGTATAGGCTACCAATTTGGTACCGAGCCCTTCACGGGCAGTGGAACTCTGAACGTCG
CATCCTGGACCGCATCTATCAACTAA (SEQ. ID NO: 4)

Figure 20 atggtttgcctttccagcctcatctgcgctctccaccagcatcgccagtactctggcgatgcccacaggcctgagagcagtcaactgtcaacgtcacagagcgtggcatgtacgactttgttctt
ggagctcacaatgatcatcgccgtcgttgacgactgactgctagcatacgaccaaaactaccaaaactgccgacaagtcagctatccgccttccaaactcagttctctcagtgaactggaacactcaagatg
actttgtgggcgttggttggacgactggatctctgcgtaggaggactctcatcattctgcactttgaaaagcatctctgaccaaaagcttctcttagtccatcaacttggcggctctcttagtg
tcaacagcggaactggcctgtcttccgtcgtatgctggagcaccaaccactccgtgcaacagccttcaatcatgttgagtactacatcaggcacacacaggtacccgtcaaggaaccgtcacc
agcgacggagccactttaccaccatctggagaatacccgtgtcaacgagcttcatccaggcacagcgaccttcaaccagtacatttccgtgcgaactgcgcccaggaccagcggaactg
ttactgcagaaccacttcaatgcttggcctgcgcttcaatgcgccagtaactaccacaggttgtcgtcgaaggctgggtggtagtggttctgcctcacagagtgtcagcaac
tag Xylanase I Amino Acid sequence MVAFSSLICALTSIASTLAMPTGLEPESSVNVTERGMYDFVLGAHNDHRRASINYDQNYQTGGQVSYSPSNTGFSVNW
N
TQDDFVVGVGWTTGSSAEDSSSFCTLKASSDQKLLLVPSTLAALLVSTAELACFPSMAGAPTHWLSTTSWRTTTTQHR
VPSREPSPATEPLTPSGRIPVSTSLPSRAQRPSTSTFPCGTRPGPAELLCRTTSMLGPRLACTLGR.TTRLSLSKAGVV
VVLPHRVSAT

SEQUENCE LISTING

<160> NUMBER OF SEQ ID NOS: 51

<210> SEQ ID NO 1
<211> LENGTH: 223
<212> TYPE: PRT
<213> ORGANISM: Trichoderma reesei

<400> SEQUENCE: 1

Met Val Ser Phe Thr Ser Leu Leu Ala Gly Val Ala Ala Ile Ser Gly
 1               5                  10                  15

Val Leu Ala Ala Pro Ala Ala Glu Val Glu Ser Val Ala Val Glu Lys
            20                  25                  30

Arg Gln Thr Ile Gln Pro Gly Thr Gly Tyr Asn Asn Gly Tyr Phe Tyr
        35                  40                  45

Ser Tyr Trp Asn Asp Gly His Gly Gly Val Thr Tyr Thr Asn Gly Pro
    50                  55                  60

Gly Gly Gln Phe Ser Val Asn Trp Ser Asn Ser Gly Asn Phe Val Gly
65                  70                  75                  80

Gly Lys Gly Trp Gln Pro Gly Thr Lys Asn Lys Val Ile Asn Phe Ser
                85                  90                  95

Gly Ser Tyr Asn Pro Asn Gly Asn Ser Tyr Leu Ser Val Tyr Gly Trp
            100                 105                 110

Ser Arg Asn Pro Leu Ile Glu Tyr Tyr Ile Val Glu Asn Phe Gly Thr
        115                 120                 125

Tyr Asn Pro Ser Thr Gly Ala Thr Lys Leu Gly Glu Val Thr Ser Asp
    130                 135                 140

Gly Ser Val Tyr Asp Ile Tyr Arg Thr Gln Arg Val Asn Gln Pro Ser
145                 150                 155                 160

Ile Ile Gly Thr Ala Thr Phe Tyr Gln Tyr Trp Ser Val Arg Arg Asn
                165                 170                 175

His Arg Ser Ser Gly Ser Val Asn Thr Ala Asn His Phe Asn Ala Trp
            180                 185                 190

Ala Gln Gln Gly Leu Thr Leu Gly Thr Met Asp Tyr Gln Ile Val Ala
        195                 200                 205

Val Glu Gly Tyr Phe Ser Ser Gly Ser Ala Ser Ile Thr Val Ser
    210                 215                 220

<210> SEQ ID NO 2
<211> LENGTH: 781
<212> TYPE: DNA
<213> ORGANISM: Trichoderma reesei

<400> SEQUENCE: 2
atggtctcct tcacctccct cctcgccggc gtcgccgcca tctcgggcgt cttggccgct        60
cccgccgccg aggtcgaatc cgtggctgtg gagaagcgcc agacgattca gcccggcacg       120
ggctacaaca acggctactt ctactcgtac tggaacgatg gccacggcgg cgtgacgtac       180

```
accaatggtc ccggcgggca gttctccgtc aactggtcca actcgggcaa ctttgtcggc    240
ggcaagggat ggcagcccgg caccaagaac aagtaagact acctactctt accccctttg    300
accaacacag cacaacacaa tacaacacat gtgactacca atcatggaat cggatctaac    360
agctgtgttt tcaaaaaaaa gggtcatcaa cttctcgggc agctacaacc ccaacggcaa    420
cagctacctc tccgtgtacg gctggtcccg caaccccctg atcgagtact acatcgtcga    480
gaactttggc acctacaacc cgtccacggg cgccaccaag ctgggcgagg tcacctccga    540
cggcagcgtc tacgacattt accgcacgca gcgcgtcaac cagccgtcca tcatcggcac    600
cgccaccttt taccagtact ggtccgtccg ccgcaaccac cgctcgagcg gctccgtcaa    660
cacggcgaac cacttcaacg cgtgggctca gcaaggcctg acgctcggga cgatggatta    720
ccagattgtt gccgtggagg gttactttag ctctggctct gcttccatca ccgtcagcta    780
a                                                                    781
```

<210> SEQ ID NO 3
<211> LENGTH: 234
<212> TYPE: PRT
<213> ORGANISM: Trichoderma reesei

<400> SEQUENCE: 3

```
Met Lys Phe Leu Gln Val Leu Pro Ala Leu Ile Pro Ala Ala Leu Ala
1               5                   10                  15

Gln Thr Ser Cys Asp Gln Trp Ala Thr Phe Thr Gly Asn Gly Tyr Thr
            20                  25                  30

Val Ser Asn Asn Leu Trp Gly Ala Ser Ala Gly Ser Gly Phe Gly Cys
        35                  40                  45

Val Thr Ala Val Ser Leu Ser Gly Gly Ala Ser Trp His Ala Asp Trp
    50                  55                  60

Gln Trp Ser Gly Gly Gln Asn Asn Val Lys Ser Tyr Gln Asn Ser Gln
65                  70                  75                  80

Ile Ala Ile Pro Gln Lys Arg Thr Val Asn Ser Ile Ser Ser Met Pro
                85                  90                  95

Thr Thr Ala Ser Trp Ser Tyr Ser Gly Ser Asn Ile Arg Ala Asn Val
            100                 105                 110

Ala Tyr Asp Leu Phe Thr Ala Ala Asn Pro Asn His Val Thr Tyr Ser
        115                 120                 125

Gly Asp Tyr Glu Leu Met Ile Trp Leu Gly Lys Tyr Gly Asp Ile Gly
    130                 135                 140

Pro Ile Gly Ser Ser Gln Gly Thr Val Asn Val Gly Gly Gln Ser Trp
145                 150                 155                 160

Thr Leu Tyr Tyr Gly Tyr Asn Gly Ala Met Gln Val Tyr Ser Phe Val
                165                 170                 175

Ala Gln Thr Asn Thr Thr Asn Tyr Ser Gly Asp Val Lys Asn Phe Phe
            180                 185                 190

Asn Tyr Leu Arg Asp Asn Lys Gly Tyr Asn Ala Ala Gly Gln Tyr Val
        195                 200                 205

Leu Ser Tyr Gln Phe Gly Thr Glu Pro Phe Thr Gly Ser Gly Thr Leu
    210                 215                 220

Asn Val Ala Ser Trp Thr Ala Ser Ile Asn
225                 230
```

<210> SEQ ID NO 4
<211> LENGTH: 826
<212> TYPE: DNA

<213> ORGANISM: Trichoderma reesei

<400> SEQUENCE: 4

```
atgaagttcc ttcaagtcct ccctgccctc ataccggccg ccctggccca aaccagctgt    60
gaccagtggg caaccttcac tggcaacggc tacacagtca gcaacaacct ttggggagca   120
tcagccggct ctggatttgg ctgcgtgacg gcggtatcgc tcagcggcgg ggcctcctgg   180
cacgcagact ggcagtggtc cggcggccag aacaacgtca agtcgtacca gaactctcag   240
attgccattc cccagaagag gaccgtcaac agcatcagca gcatgcccac cactgccagc   300
tggagctaca gcgggagcaa catccgcgct aatgttgcgt atgacttgtt cacccgcagcc   360
aacccgaatc atgtcacgta ctcgggagac tacgaactca tgatctggta agccataaga   420
agtgaccctc cttgatagtt tcgactaaca acatgtcttg aggcttggca aatacggcga   480
tattgggccg attgggtcct cacagggaac agtcaacgtc ggtggccaga gctggacgct   540
ctactatggc tacaacggag ccatgcaagt ctattccttt gtggcccaga ccaacactac   600
caactacagc ggagatgtca agaacttctt caattatctc cgagacaata aaggatacaa   660
cgctgcaggc caatatgttc ttagtaagtc accctcactg tgactgggct gagtttgttg   720
caacgtttgc taacaaaacc ttcgtatagg ctaccaattt ggtaccgagc ccttcacggg   780
cagtggaact ctgaacgtcg catcctggac cgcatctatc aactaa                  826
```

<210> SEQ ID NO 5
<211> LENGTH: 222
<212> TYPE: PRT
<213> ORGANISM: Trichoderma reesei

<400> SEQUENCE: 5

```
Met Val Ser Phe Thr Ser Leu Leu Ala Ala Ser Pro Pro Ser Arg Ala
  1               5                  10                  15
Ser Cys Arg Pro Ala Ala Glu Val Glu Ser Val Ala Val Glu Lys Arg
                 20                  25                  30
Gln Thr Ile Gln Pro Gly Thr Gly Tyr Asn Asn Gly Tyr Phe Tyr Ser
             35                  40                  45
Tyr Trp Asn Asp Gly His Gly Gly Val Thr Tyr Thr Asn Gly Pro Gly
 50                  55                  60
Gly Gln Phe Ser Val Asn Trp Ser Asn Ser Gly Asn Phe Val Gly Gly
 65                  70                  75                  80
Lys Gly Trp Gln Pro Gly Thr Lys Asn Lys Val Ile Asn Phe Ser Gly
                 85                  90                  95
Ser Tyr Asn Pro Asn Gly Asn Ser Tyr Leu Ser Val Tyr Gly Trp Ser
                100                 105                 110
Arg Asn Pro Leu Ile Glu Tyr Tyr Ile Val Glu Asn Phe Gly Thr Tyr
             115                 120                 125
Asn Pro Ser Thr Gly Ala Thr Lys Leu Gly Glu Val Thr Ser Asp Gly
         130                 135                 140
Ser Val Tyr Asp Ile Tyr Arg Thr Gln Arg Val Asn Gln Pro Ser Ile
145                 150                 155                 160
Ile Gly Thr Ala Thr Phe Tyr Gln Tyr Trp Ser Val Arg Arg Asn His
                165                 170                 175
Arg Ser Ser Gly Ser Val Asn Thr Ala Asn His Phe Asn Ala Trp Ala
             180                 185                 190
Gln Gln Gly Leu Thr Leu Gly Thr Met Asp Tyr Gln Ile Val Ala Val
         195                 200                 205
```

```
Glu Gly Tyr Phe Ser Ser Gly Ser Ala Ser Ile Thr Val Ser
    210                 215                 220
```

<210> SEQ ID NO 6
<211> LENGTH: 227
<212> TYPE: PRT
<213> ORGANISM: Humicola insolens

<400> SEQUENCE: 6

```
Met Val Ser Leu Lys Ser Val Leu Ala Ala Thr Ala Val Ser Ser
1               5                   10                  15

Ala Ile Ala Ala Pro Phe Asp Phe Val Pro Arg Asp Asn Ser Thr Ala
            20                  25                  30

Leu Gln Ala Arg Gln Val Thr Pro Asn Ala Glu Gly Trp His Asn Gly
        35                  40                  45

Tyr Phe Tyr Ser Trp Trp Ser Asp Gly Gly Gln Val Gln Tyr Thr
    50                  55                  60

Asn Leu Glu Gly Ser Arg Tyr Gln Val Arg Trp Arg Asn Thr Gly Asn
65                  70                  75                  80

Phe Val Gly Gly Lys Gly Trp Asn Pro Gly Thr Gly Arg Thr Ile Asn
                85                  90                  95

Tyr Gly Gly Tyr Phe Asn Pro Gln Gly Asn Gly Tyr Leu Ala Val Tyr
                100                 105                 110

Gly Trp Thr Arg Asn Pro Leu Val Glu Tyr Tyr Val Ile Glu Ser Tyr
            115                 120                 125

Gly Thr Tyr Asn Pro Gly Ser Gln Ala Gln Tyr Lys Gly Thr Phe Tyr
        130                 135                 140

Thr Asp Gly Asp Gln Tyr Asp Ile Phe Val Ser Thr Arg Tyr Asn Gln
145                 150                 155                 160

Pro Ser Ile Asp Gly Thr Arg Thr Phe Gln Gln Tyr Trp Ser Ile Arg
                165                 170                 175

Lys Asn Lys Arg Val Gly Gly Ser Val Asn Met Gln Asn His Phe Asn
                180                 185                 190

Ala Trp Gln Gln His Gly Met Pro Leu Gly His Tyr Tyr Gln Val
            195                 200                 205

Val Ala Thr Glu Gly Tyr Gln Ser Ser Gly Glu Ser Asp Ile Tyr Val
    210                 215                 220

Gln Thr His
225
```

<210> SEQ ID NO 7
<211> LENGTH: 210
<212> TYPE: PRT
<213> ORGANISM: Bacillus stearothermophilus

<400> SEQUENCE: 7

```
Met Lys Leu Lys Lys Lys Met Leu Thr Leu Leu Leu Thr Ala Ser Met
1               5                   10                  15

Ser Phe Gly Leu Phe Gly Ala Thr Ser Ser Ala Ala Thr Asp Tyr Trp
            20                  25                  30

Gln Tyr Trp Thr Asp Gly Gly Gly Met Val Asn Ala Val Asn Gly Pro
        35                  40                  45

Gly Gly Asn Tyr Ser Val Thr Trp Gln Asn Thr Gly Asn Phe Val Val
    50                  55                  60

Gly Lys Gly Trp Thr Val Gly Ser Pro Asn Arg Val Ile Asn Tyr Asn
65                  70                  75                  80
```

```
Ala Gly Ile Trp Glu Pro Ser Gly Asn Gly Tyr Leu Thr Leu Tyr Gly
            85                  90                  95

Trp Thr Arg Asn Ala Leu Ile Glu Tyr Tyr Val Val Asp Ser Trp Gly
            100                 105                 110

Thr Tyr Arg Pro Thr Gly Asn Tyr Lys Gly Thr Val Asn Ser Asp Gly
            115                 120                 125

Gly Thr Tyr Asp Ile Tyr Thr Thr Met Arg Tyr Asn Ala Pro Ser Ile
    130                 135                 140

Asp Gly Thr Gln Thr Phe Gln Gln Phe Trp Ser Val Arg Gln Ser Lys
145                 150                 155                 160

Arg Pro Thr Gly Ser Asn Val Ser Ile Thr Phe Ser Asn His Val Asn
                165                 170                 175

Ala Trp Arg Ser Lys Gly Met Asn Leu Gly Ser Ser Trp Ala Tyr Gln
            180                 185                 190

Val Leu Ala Thr Glu Gly Tyr Gln Ser Ser Gly Arg Ser Asn Val Thr
        195                 200                 205

Val Trp
    210

<210> SEQ ID NO 8
<211> LENGTH: 229
<212> TYPE: PRT
<213> ORGANISM: Trichoderma reesei

<400> SEQUENCE: 8

Met Val Ala Phe Ser Ser Leu Ile Cys Ala Leu Thr Ser Ile Ala Ser
1               5                   10                  15

Thr Leu Ala Met Pro Thr Gly Leu Glu Pro Glu Ser Ser Val Asn Val
            20                  25                  30

Thr Glu Arg Gly Met Tyr Asp Phe Val Leu Gly Ala His Asn Asp His
            35                  40                  45

Arg Arg Arg Ala Ser Ile Asn Tyr Asp Gln Asn Tyr Gln Thr Gly Gly
    50                  55                  60

Gln Val Ser Tyr Ser Pro Ser Asn Thr Gly Phe Ser Val Asn Trp Asn
65                  70                  75                  80

Thr Gln Asp Asp Phe Val Val Gly Val Gly Trp Thr Thr Gly Ser Ser
            85                  90                  95

Ala Pro Ile Asn Phe Gly Gly Ser Phe Ser Val Asn Ser Gly Thr Gly
            100                 105                 110

Leu Leu Ser Val Tyr Gly Trp Ser Thr Asn Pro Leu Val Glu Tyr Tyr
            115                 120                 125

Ile Met Glu Asp Asn His Asn Tyr Pro Ala Gln Gly Thr Val Lys Gly
    130                 135                 140

Thr Val Thr Ser Asp Gly Ala Thr Tyr Thr Ile Trp Glu Asn Thr Arg
145                 150                 155                 160

Val Asn Glu Pro Ser Ile Gln Gly Thr Ala Thr Phe Asn Gln Tyr Ile
                165                 170                 175

Ser Val Arg Asn Ser Pro Arg Thr Ser Gly Thr Val Thr Val Gln Asn
            180                 185                 190

His Phe Asn Ala Trp Ala Ser Leu Gly Leu His Leu Gly Gln Met Asn
        195                 200                 205

Tyr Gln Val Val Ala Val Glu Gly Trp Gly Gly Ser Gly Ser Ala Ser
    210                 215                 220

Gln Ser Val Ser Asn
225
```

<210> SEQ ID NO 9
<211> LENGTH: 211
<212> TYPE: PRT
<213> ORGANISM: Aspergillus awamori

<400> SEQUENCE: 9

```
Met Lys Val Thr Ala Ala Phe Ala Gly Leu Leu Val Thr Ala Phe Ala
 1               5                  10                  15

Ala Pro Val Pro Glu Pro Val Leu Val Ser Arg Ser Ala Gly Ile Asn
                20                  25                  30

Tyr Val Gln Asn Tyr Asn Gly Asn Leu Gly Asp Phe Thr Tyr Asp Glu
             35                  40                  45

Ser Ala Gly Thr Phe Ser Met Tyr Trp Glu Asp Gly Val Ser Ser Asp
         50                  55                  60

Phe Val Val Gly Leu Gly Trp Thr Thr Gly Ser Ser Asn Ala Ile Thr
 65                  70                  75                  80

Tyr Ser Ala Glu Tyr Ser Ala Ser Gly Ser Ser Ser Tyr Leu Ala Val
                 85                  90                  95

Tyr Gly Trp Val Asn Tyr Pro Gln Ala Glu Tyr Tyr Ile Val Glu Asp
                100                 105                 110

Tyr Gly Asp Tyr Asn Pro Cys Ser Ser Ala Thr Ser Leu Gly Thr Val
             115                 120                 125

Tyr Ser Asp Gly Ser Thr Tyr Gln Val Cys Thr Asp Thr Arg Thr Asn
         130                 135                 140

Glu Pro Ser Ile Thr Gly Thr Ser Thr Phe Thr Gln Tyr Phe Ser Val
145                 150                 155                 160

Arg Glu Ser Thr Arg Thr Ser Gly Thr Val Thr Val Ala Asn His Phe
                165                 170                 175

Asn Phe Trp Ala Gln His Gly Phe Gly Asn Ser Asp Phe Asn Tyr Gln
            180                 185                 190

Val Met Ala Val Glu Ala Trp Ser Gly Ala Gly Ser Ala Ser Val Thr
        195                 200                 205

Ile Ser Ser
    210
```

<210> SEQ ID NO 10
<211> LENGTH: 330
<212> TYPE: PRT
<213> ORGANISM: Bacillus stearothermophilus

<400> SEQUENCE: 10

```
Met Cys Ser Ser Ile Pro Ser Leu Arg Glu Val Phe Ala Asn Asp Phe
 1               5                  10                  15

Arg Ile Gly Ala Ala Val Asn Pro Val Thr Leu Glu Ala Gln Gln Ser
                20                  25                  30

Leu Leu Ile Arg His Val Asn Ser Leu Thr Ala Glu Asn His Met Lys
             35                  40                  45

Phe Glu His Leu Gln Pro Glu Glu Gly Arg Phe Thr Phe Asp Ile Ala
         50                  55                  60

Ile Lys Ser Ser Thr Ser Pro Phe Ser His Gly Val Arg Gly His
 65                  70                  75                  80

Thr Leu Val Trp His Asn Gln Thr Pro Ser Trp Val Phe Gln Asp Ser
                 85                  90                  95

Gln Gly His Phe Val Gly Arg Asp Val Leu Leu Glu Arg Met Lys Ser
                100                 105                 110
```

-continued

His Ile Ser Thr Val Val Gln Arg Tyr Lys Gly Lys Val Tyr Cys Trp
            115                 120                 125

Asp Val Ile Asn Glu Ala Val Ala Asp Glu Gly Ser Glu Trp Leu Arg
130                 135                 140

Ser Ser Thr Trp Arg Gln Ile Ile Gly Asp Asp Phe Ile Gln Gln Ala
145                 150                 155                 160

Phe Leu Tyr Ala His Glu Ala Asp Pro Glu Ala Leu Leu Phe Tyr Asn
                165                 170                 175

Asp Tyr Asn Glu Cys Phe Pro Glu Lys Arg Glu Lys Ile Tyr Thr Leu
                180                 185                 190

Val Lys Ser Leu Arg Asp Lys Gly Ile Pro Ile His Gly Ile Gly Met
            195                 200                 205

Gln Ala His Trp Ser Leu Asn Arg Pro Thr Leu Asp Glu Ile Arg Ala
        210                 215                 220

Ala Ile Glu Arg Tyr Ala Ser Leu Gly Val Ile Leu His Ile Thr Glu
225                 230                 235                 240

Leu Asp Ile Ser Met Phe Glu Phe Asp Asp His Arg Lys Asp Leu Ala
                245                 250                 255

Ala Pro Thr Asn Glu Met Val Glu Arg Gln Ala Glu Arg Tyr Glu Gln
            260                 265                 270

Ile Phe Ser Leu Phe Lys Glu Tyr Arg Asp Val Ile Gln Asn Val Thr
        275                 280                 285

Phe Trp Gly Ile Ala Asp Asp His Thr Trp Leu Asp His Phe Pro Val
    290                 295                 300

Gln Gly Arg Lys Asn Trp Pro Leu Leu Phe Asp Glu Gln His Asn Pro
305                 310                 315                 320

Lys Pro Ala Phe Trp Arg Val Val Asn Ile
                325                 330

<210> SEQ ID NO 11
<211> LENGTH: 190
<212> TYPE: PRT
<213> ORGANISM: Trichoderma reesei

<400> SEQUENCE: 11

Gln Thr Ile Gln Pro Gly Thr Gly Tyr Asn Asn Gly Tyr Phe Tyr Ser
1               5                   10                  15

Tyr Trp Asn Asp Gly His Gly Gly Val Thr Tyr Thr Asn Gly Pro Gly
            20                  25                  30

Gly Gln Phe Ser Val Asn Trp Ser Asn Ser Gly Asn Phe Val Gly Gly
        35                  40                  45

Lys Gly Trp Gln Pro Gly Thr Lys Asn Lys Val Ile Asn Phe Ser Gly
    50                  55                  60

Ser Tyr Asn Pro Asn Gly Asn Ser Tyr Leu Ser Val Tyr Gly Trp Ser
65                  70                  75                  80

Arg Asn Pro Leu Ile Glu Tyr Tyr Ile Val Glu Asn Phe Gly Thr Tyr
                85                  90                  95

Asn Pro Ser Thr Gly Ala Thr Lys Leu Gly Glu Val Thr Ser Asp Gly
            100                 105                 110

Ser Val Tyr Asp Ile Tyr Arg Thr Gln Arg Val Asn Gln Pro Ser Ile
        115                 120                 125

Ile Gly Thr Ala Thr Phe Tyr Gln Tyr Trp Ser Val Arg Arg Asn His
    130                 135                 140

Arg Ser Ser Gly Ser Val Asn Thr Ala Asn His Phe Asn Ala Trp Ala

-continued

```
            145                 150                 155                 160
Gln Gln Gly Leu Thr Leu Gly Thr Met Asp Tyr Gln Ile Val Ala Val
                165                 170                 175
Glu Gly Tyr Phe Ser Ser Gly Ser Ala Ser Ile Thr Val Ser
            180                 185                 190

<210> SEQ ID NO 12
<211> LENGTH: 237
<212> TYPE: PRT
<213> ORGANISM: Aspergillus awamori

<400> SEQUENCE: 12

Met Lys Ala Phe His Leu Leu Ala Ala Leu Ser Gly Ala Ala Val Ala
 1               5                  10                  15

Gln Gln Ala Gln Leu Cys Asp Gln Tyr Ala Thr Tyr Thr Gly Gly Val
             20                  25                  30

Tyr Thr Ile Asn Asn Asn Leu Trp Gly Lys Asp Ala Gly Ser Gly Ser
         35                  40                  45

Gln Cys Thr Thr Val Asn Ser Ala Ser Ala Gly Thr Ser Trp Ser
     50                  55                  60

Thr Lys Trp Asn Trp Ser Gly Gly Glu Asn Ser Val Lys Ser Tyr Ala
 65                  70                  75                  80

Asn Ser Gly Leu Ser Phe Asn Lys Lys Leu Val Ser Gln Ile Ser His
                 85                  90                  95

Ile Pro Thr Ala Ala Arg Trp Ser Tyr Asp Asn Thr Cys Ile Arg Arg
            100                 105                 110

Gly Arg Ala Tyr Asp Leu Phe Thr Ala Ala Asp Ile Asn His Val Thr
        115                 120                 125

Trp Ser Gly Asp Tyr Glu Leu Met Ile Trp Leu Ala Arg Tyr Gly Gly
    130                 135                 140

Val Gln Pro Leu Gly Ser Gln Ile Ala Thr Ala Thr Val Glu Gly Gln
145                 150                 155                 160

Thr Trp Glu Leu Trp Tyr Gly Val Asn Gly Ala Gln Lys Thr Tyr Ser
                165                 170                 175

Phe Val Ala Ala Asn Pro Ile Thr Ser Phe Gln Gly Asp Ile Asn Asp
            180                 185                 190

Phe Phe Lys Tyr Leu Thr Gln Asn His Gly Phe Pro Ala Ser Ser Gln
        195                 200                 205

Tyr Leu Ile Thr Leu Gln Phe Gly Thr Glu Pro Phe Thr Gly Gly Pro
    210                 215                 220

Ala Thr Leu Asn Val Ala Asp Trp Ser Ala Ser Val Gln
225                 230                 235

<210> SEQ ID NO 13
<211> LENGTH: 233
<212> TYPE: PRT
<213> ORGANISM: Trichoderma viride

<400> SEQUENCE: 13

Met Lys Phe Leu Gln Ile Ala Pro Thr Leu Leu Pro Val Ala Leu Ala
 1               5                  10                  15

Gln Ser Ser Cys Ser Gln Tyr Ala Thr Phe Ser Gly Gly Asn Tyr Ala
             20                  25                  30

Leu Ser Asn Asn Leu Trp Gly Gln Ser Ala Gly Ser Gly Ser Gly Cys
         35                  40                  45

Ile Thr Asp Val Ser Leu Gly Gly Ser Ala Val Trp Ser Thr Thr Trp
```

```
                50                  55                  60
Asp Trp Ser Gly Gly Gln Ser Asn Val Lys Gly Tyr Pro Asn Ile Ala
 65                  70                  75                  80

Leu Asn Ile Pro Asn Lys Arg Leu Val Ser Ser Ile Ser Ser Met Pro
                 85                  90                  95

Thr Thr Ala Gln Trp Ser Tyr Ser Gly Ser Ser Ile Arg Ala Asp Val
            100                 105                 110

Ala Tyr Asp Leu Phe Thr Ala Ser Asn Pro Asn His Val Thr Tyr Ser
        115                 120                 125

Gly Asp Tyr Glu Leu Met Ile Trp Leu Gly Lys Tyr Gly Asp Ile Gln
    130                 135                 140

Pro Ile Gly Ser Ser Gln Gly Thr Val Asn Val Gly Gly Thr Ser Trp
145                 150                 155                 160

Asn Leu Trp Tyr Gly Pro Asn Gly Ser Met Gln Val Tyr Ser Phe Val
                165                 170                 175

Ala Pro Gly Asn Leu Thr Asn Trp Ser Gly Asp Val Lys Asn Phe Tyr
            180                 185                 190

Thr Tyr Leu Gln Asn Asn Lys Gly Tyr Pro Ala Ser Ser Gln Tyr Val
        195                 200                 205

Leu Ser Tyr Gln Phe Gly Thr Glu Ala Phe Thr Gly Ser Gly Thr Leu
    210                 215                 220

Asn Asn Thr Trp Thr Ala Ser Ile Asn
225                 230

<210> SEQ ID NO 14
<211> LENGTH: 234
<212> TYPE: PRT
<213> ORGANISM: Hypocrea koningii

<400> SEQUENCE: 14

Met Lys Leu Ile His Val Leu Pro Ala Leu Ile Pro Ala Ala Leu Ala
 1               5                  10                  15

Gln Thr Ser Cys Asp Gln Tyr Ala Val Phe Thr Gly Ser Asp Tyr Thr
            20                  25                  30

Val Ser Asn Asn Leu Trp Gly Gln Ser Ala Gly Ser Gly Phe Gly Cys
        35                  40                  45

Val Thr Ala Glu Ser Leu Ser Gly Ser Ala Ser Trp His Ala Asp Trp
    50                  55                  60

Gln Trp Ser Gly Gly Gln Asn Asn Val Lys Ser Tyr Gln Asn Ser Gln
 65                  70                  75                  80

Ile Pro Ile Pro Gln Lys Arg Thr Val Asn Ser Ile Ser Ser Met Pro
                 85                  90                  95

Thr Thr Ala Ser Trp Ser Tyr Thr Gly Ser Asp Ile Arg Ala Asn Val
            100                 105                 110

Ala Tyr Asp Leu Phe Thr Ala Ala Asn Pro Asn His Val Thr Tyr Ser
        115                 120                 125

Gly Asp Tyr Glu Leu Met Ile Trp Leu Gly Arg Tyr Gly Asp Ile Gly
    130                 135                 140

Pro Ile Gly Ser Ser Gln Gly Thr Val Asn Val Gly Gly Gln Ser Trp
145                 150                 155                 160

Thr Leu Tyr Tyr Gly Tyr Asn Gly Ala Met Gln Val Tyr Ser Phe Val
                165                 170                 175

Ala Gln Thr Asn Thr Thr Ser Tyr Ser Gly Asp Val Lys Asn Phe Phe
            180                 185                 190
```

```
Asn Tyr Leu Arg Asp Asn Lys Gly Tyr Asn Ala Ala Gly Gln Tyr Val
        195                 200                 205

Leu Ser Tyr Gln Phe Gly Thr Glu Pro Phe Thr Gly Ser Gly Thr Leu
        210                 215                 220

Asn Val Ala Ser Trp Thr Ala Ser Ile Asn
225                 230

<210> SEQ ID NO 15
<211> LENGTH: 234
<212> TYPE: PRT
<213> ORGANISM: Hypocrea schweinitzii

<400> SEQUENCE: 15

Met Lys Phe Leu Gln Val Leu Pro Ala Ile Leu Pro Ala Ala Leu Ala
1               5                   10                  15

Gln Thr Ser Cys Asp Gln Tyr Ala Thr Phe Ser Gly Asn Gly Tyr Ile
            20                  25                  30

Val Ser Asn Asn Leu Trp Gly Ala Ser Ala Gly Ser Gly Phe Gly Cys
        35                  40                  45

Val Thr Ser Val Ser Leu Asn Gly Ala Ala Ser Trp His Ala Asp Trp
50                  55                  60

Gln Trp Ser Gly Gly Gln Asn Asn Val Lys Ser Tyr Gln Asn Val Gln
65                  70                  75                  80

Ile Asn Ile Pro Gln Lys Arg Thr Val Asn Ser Ile Gly Ser Met Pro
                85                  90                  95

Thr Thr Ala Ser Trp Ser Tyr Ser Gly Ser Asp Ile Arg Ala Asn Val
            100                 105                 110

Ala Tyr Asp Leu Phe Thr Ala Ala Asn Pro Asn His Val Thr Tyr Ser
        115                 120                 125

Gly Asp Tyr Glu Leu Met Ile Trp Leu Gly Lys Tyr Gly Asp Ile Gly
130                 135                 140

Pro Ile Gly Ser Ser Gln Gly Thr Val Asn Val Gly Gly Gln Thr Trp
145                 150                 155                 160

Thr Leu Tyr Tyr Gly Tyr Asn Gly Ala Met Gln Val Tyr Ser Phe Val
                165                 170                 175

Ala Gln Ser Asn Thr Thr Ser Tyr Ser Gly Asp Val Lys Asn Phe Phe
            180                 185                 190

Asn Tyr Leu Arg Asp Asn Lys Gly Tyr Asn Ala Gly Gly Gln Tyr Val
        195                 200                 205

Leu Ser Tyr Gln Phe Gly Thr Glu Pro Phe Thr Gly Ser Gly Thr Leu
        210                 215                 220

Asn Val Ala Ser Trp Thr Ala Ser Ile Asn
225                 230

<210> SEQ ID NO 16
<211> LENGTH: 237
<212> TYPE: PRT
<213> ORGANISM: Stachybotrys echinata

<400> SEQUENCE: 16

Met Lys Val Ala Ala Leu Leu Val Ala Leu Ser Pro Leu Ala Phe Ala
1               5                   10                  15

Gln Ser Leu Cys Asp Gln Tyr Ser Tyr Ser Ser Asn Gly Tyr Glu
            20                  25                  30

Phe Asn Asn Asn Met Trp Gly Arg Asn Ser Gly Gln Gly Asn Gln Cys
        35                  40                  45
```

```
Thr Tyr Val Asp Tyr Ser Ser Pro Asn Gly Val Gly Trp Arg Val Asn
        50                  55                  60

Trp Asn Trp Ser Gly Gly Asp Asn Asn Val Lys Ser Tyr Pro Tyr Ser
65                  70                  75                  80

Gly Arg Gln Leu Pro Thr Lys Arg Ile Val Ser Trp Ile Gly Ser Leu
                85                  90                  95

Pro Thr Thr Val Ser Trp Asn Tyr Gln Gly Asn Asn Leu Arg Ala Asn
            100                 105                 110

Val Ala Tyr Asp Leu Phe Thr Ala Ala Asn Pro Asn His Pro Asn Ser
        115                 120                 125

Ser Gly Asp Tyr Glu Leu Met Ile Trp Leu Gly Arg Leu Gly Asn Val
    130                 135                 140

Tyr Pro Ile Gly Asn Gln Val Ala Thr Val Asn Ile Ala Gly Gln Gln
145                 150                 155                 160

Trp Asn Leu Tyr Tyr Gly Tyr Asn Gly Ala Met Gln Val Tyr Ser Phe
                165                 170                 175

Val Ser Pro Asn Gln Leu Asn Tyr Phe Ser Gly Asn Val Lys Asp Phe
            180                 185                 190

Phe Thr Tyr Leu Gln Tyr Asn Arg Ala Tyr Pro Ala Asp Ser Gln Tyr
        195                 200                 205

Leu Ile Thr Tyr Gln Phe Gly Thr Glu Pro Phe Thr Gly Gln Asn Ala
    210                 215                 220

Val Phe Thr Val Ser Asn Trp Ser Ala Gln Gln Asn Asn
225                 230                 235

<210> SEQ ID NO 17
<211> LENGTH: 238
<212> TYPE: PRT
<213> ORGANISM: Fusarium equiseti

<400> SEQUENCE: 17

Met Lys Ser Thr Leu Leu Ala Gly Ala Phe Ala Pro Leu Ala Phe
1               5                   10                  15

Ala Lys Asp Leu Cys Glu Gln Tyr Gly Tyr Leu Ser Ser Asp Gly Tyr
            20                  25                  30

Ser Leu Asn Asn Asn Val Trp Gly Lys Asp Ser Gly Thr Gly Asp Gln
        35                  40                  45

Cys Thr His Val Asn Trp Asn Asn Ala Asn Gly Ala Gly Trp Asp Val
    50                  55                  60

Glu Trp Asn Trp Ser Gly Gly Lys Asp Asn Val Lys Ser Tyr Pro Asn
65                  70                  75                  80

Ser Ala Leu Leu Ile Gly Glu Asp Lys Lys Thr Ile Ser Ser Ile Thr
                85                  90                  95

Asn Met Gln Ser Thr Ala Glu Trp Lys Tyr Ser Gly Asp Asn Leu Arg
            100                 105                 110

Ala Asp Val Ala Tyr Asp Leu Phe Thr Ala Ala Asp Pro Asn His Glu
        115                 120                 125

Thr Ser Ser Gly Glu Tyr Glu Leu Met Val Trp Leu Ala Arg Ile Gly
    130                 135                 140

Gly Val Gln Pro Ile Gly Ser Leu Gln Thr Ser Val Thr Ile Glu Gly
145                 150                 155                 160

His Thr Trp Glu Leu Trp Val Gly Met Asn Gly Ser Met Lys Val Phe
                165                 170                 175

Ser Phe Val Ala Pro Thr Pro Val Asn Asn Phe Asn Ala Asp Ile Lys
            180                 185                 190
```

```
Gln Phe Trp Asp Tyr Leu Thr Lys Ser Gln Asn Phe Pro Ala Asp Asn
            195                 200                 205

Gln Tyr Leu Leu Thr Phe Gln Phe Gly Thr Glu Pro Phe Thr Gly Asp
    210                 215                 220

Asn Ala Lys Phe Thr Val Thr Asn Phe Asn Ala His Leu Lys
225                 230                 235

<210> SEQ ID NO 18
<211> LENGTH: 237
<212> TYPE: PRT
<213> ORGANISM: Bionectria ochroleuca

<400> SEQUENCE: 18

Met Lys Thr Gly Ile Ala Tyr Leu Ala Ala Val Leu Pro Leu Ala Met
1               5                   10                  15

Ala Glu Ser Leu Cys Asp Gln Tyr Ala Tyr Leu Ser Arg Asp Gly Tyr
            20                  25                  30

Asn Phe Asn Asn Asn Glu Trp Gly Ala Ala Thr Gly Thr Gly Asp Gln
        35                  40                  45

Cys Thr Tyr Val Asp Ser Thr Ser Ser Gly Gly Val Ser Trp His Ser
50                  55                  60

Asp Trp Thr Asn Ser Gly Ser Glu Ser Glu Ile Lys Ser Tyr Pro Tyr
65                  70                  75                  80

Ser Gly Leu Asp Leu Pro Glu Lys Lys Ile Val Thr Ser Ile Gly Ser
                85                  90                  95

Ile Ser Thr Gly Ala Glu Trp Ser Tyr Ser Gly Ser Asn Ile Arg Ala
            100                 105                 110

Asp Val Ala Tyr Asp Ile Phe Thr Ala Ala Asp Pro Asn His Ala Thr
        115                 120                 125

Ser Ser Gly Asp Tyr Glu Val Met Ile Trp Leu Ala Asn Leu Gly Gly
130                 135                 140

Leu Thr Pro Ile Gly Ser Pro Ile Gly Thr Val Lys Ala Ala Gly Arg
145                 150                 155                 160

Asp Trp Glu Leu Trp Asp Gly Tyr Asn Gly Ala Met Arg Val Tyr Ser
                165                 170                 175

Phe Val Ala Pro Ser Gln Leu Asn Ser Phe Asp Gly Glu Ile Met Asp
            180                 185                 190

Phe Phe Tyr Val Val Lys Asp Met Arg Gly Phe Pro Ala Asp Ser Gln
        195                 200                 205

His Leu Leu Thr Val Gln Phe Gly Thr Glu Pro Ile Ser Gly Ser Gly
    210                 215                 220

Ala Lys Phe Ser Val Ser His Trp Ser Ala Lys Leu Gly
225                 230                 235

<210> SEQ ID NO 19
<211> LENGTH: 236
<212> TYPE: PRT
<213> ORGANISM: Bionectria ochroleuca

<400> SEQUENCE: 19

Met Lys Phe Gln Leu Leu Ser Leu Thr Ala Phe Ala Pro Leu Ser Leu
1               5                   10                  15

Ala Ala Leu Cys Gly Gln Tyr Gln Ser Gln Ser Gln Gly Gly Tyr Ile
            20                  25                  30

Phe Asn Asn Asn Lys Trp Gly Gln Gly Ser Gly Ser Gly Ser Gln Cys
        35                  40                  45
```

-continued

```
Leu Thr Ile Asp Lys Thr Trp Asp Ser Asn Val Ala Phe His Ala Asp
    50                  55                  60

Trp Ser Trp Ser Gly Gly Thr Asn Asn Val Lys Ser Tyr Pro Asn Ala
65                  70                  75                  80

Gly Leu Glu Phe Ser Arg Gly Lys Lys Val Ser Ser Ile Gly Thr Ile
                85                  90                  95

Asn Gly Gly Ala Asp Trp Asp Tyr Ser Gly Ser Asn Ile Arg Ala Asn
            100                 105                 110

Val Ala Tyr Asp Ile Phe Thr Ser Ala Asp Pro Asn His Val Thr Ser
        115                 120                 125

Ser Gly Asp Tyr Glu Leu Met Ile Trp Leu Gly Lys Leu Gly Asp Ile
    130                 135                 140

Tyr Pro Ile Gly Asn Ser Ile Gly Arg Val Lys Ala Ala Asn Arg Glu
145                 150                 155                 160

Trp Asp Leu His Val Gly Tyr Asn Gly Ala Met Lys Val Phe Ser Phe
                165                 170                 175

Val Ala Pro Ser Pro Val Thr Arg Phe Asp Gly Asn Ile Met Asp Phe
            180                 185                 190

Phe Tyr Val Met Arg Asp Met Gln Gly Tyr Pro Met Asp Lys Gln Tyr
        195                 200                 205

Leu Leu Thr Leu Gln Phe Gly Thr Glu Pro Phe Thr Gly Ser Asn Ala
    210                 215                 220

Lys Phe Ser Cys Trp Tyr Phe Gly Ala Lys Ile Lys
225                 230                 235

<210> SEQ ID NO 20
<211> LENGTH: 240
<212> TYPE: PRT
<213> ORGANISM: Bionectria ochroleuca

<400> SEQUENCE: 20

Met Lys Ala Asn Ile Val Ile Leu Ser Leu Phe Ala Pro Leu Ala Ala
  1               5                  10                  15

Val Ala Gln Thr Leu Cys Gly Gln Tyr Ser Ser Asn Thr Gln Gly Gly
                20                  25                  30

Tyr Ile Phe Asn Asn Asn Met Trp Gly Met Gly Ser Gly Ser Gly Ser
            35                  40                  45

Gln Cys Thr Tyr Val Asp Lys Val Trp Ala Glu Gly Val Ala Trp His
    50                  55                  60

Thr Asp Trp Ser Trp Ser Gly Gly Asp Asn Asn Val Lys Ser Tyr Pro
65                  70                  75                  80

Tyr Ser Gly Arg Glu Leu Gly Thr Lys Arg Ile Val Ser Ser Ile Lys
                85                  90                  95

Ser Ile Ser Ser Gly Ala Asp Trp Asp Tyr Thr Gly Ser Asn Leu Arg
            100                 105                 110

Ala Asn Ala Ala Tyr Asp Ile Phe Thr Ser Ala Asn Pro Asn His Ala
        115                 120                 125

Thr Ser Ser Gly Asp Tyr Glu Val Met Ile Trp Leu Gly Arg Tyr Gly
    130                 135                 140

Gly Val Tyr Pro Ile Gly Asn Ser Ile Gly Thr Val Arg Ala Ala Gly
145                 150                 155                 160

Arg Asp Trp Ala Leu His Ile Gly Tyr Asn Gly Ala Met Lys Val Phe
                165                 170                 175

Ser Phe Val Ala Ala Asn Pro Val Thr Arg Phe Asp Gly Glu Ile Met
```

-continued

```
                    180                 185                 190
Asp Phe Phe Tyr Leu Leu Arg Asp Met Gln Gly Tyr Pro Met Thr Ser
            195                 200                 205

Gln Tyr Leu Leu Thr Leu Gln Phe Gly Thr Glu Pro Phe Thr Gly Ser
        210                 215                 220

Gly Ala Lys Phe Asn Cys Trp Tyr Phe Gly Ala Thr Leu Ser Tyr Trp
225                 230                 235                 240

<210> SEQ ID NO 21
<211> LENGTH: 254
<212> TYPE: PRT
<213> ORGANISM: Humicola grisea

<400> SEQUENCE: 21

Met Leu Lys Ser Ala Leu Leu Gly Ala Ala Ala Val Ser Val Gln
1               5                   10                  15

Ser Ala Ser Ile Pro Thr Ile Pro Ala Asn Leu Glu Pro Arg Gln Ile
            20                  25                  30

Arg Ser Leu Cys Glu Leu Tyr Gly Tyr Trp Ser Gly Asn Gly Tyr Glu
        35                  40                  45

Leu Leu Asn Asn Leu Trp Gly Lys Asp Thr Ala Thr Ser Gly Trp Gln
    50                  55                  60

Cys Thr Tyr Leu Asp Gly Thr Asn Asn Gly Gly Ile Gln Trp Asn Thr
65                  70                  75                  80

Ala Trp Glu Trp Gln Gly Ala Pro Asp Asn Val Lys Asn Tyr Pro Tyr
                85                  90                  95

Val Gly Lys Gln Ile Gln Arg Gly Arg Lys Ile Ser Asp Ile Asn Ser
            100                 105                 110

Met Arg Thr Ser Val Ser Trp Thr Tyr Asp Arg Thr Asp Leu Arg Ala
        115                 120                 125

Asn Val Ala Tyr Asp Val Phe Thr Ala Arg Asp Pro Asp His Pro Asn
    130                 135                 140

Trp Gly Gly Asp Tyr Glu Leu Met Ile Trp Leu Ala Arg Tyr Gly Gly
145                 150                 155                 160

Ile Tyr Pro Ile Gly Thr Phe His Ser Gln Val Asn Leu Ala Gly Arg
                165                 170                 175

Thr Trp Asp Leu Trp Thr Gly Tyr Asn Gly Asn Met Arg Val Tyr Ser
            180                 185                 190

Phe Leu Pro Pro Ser Gly Asp Ile Arg Asp Phe Ser Cys Asp Ile Lys
        195                 200                 205

Asp Phe Phe Asn Tyr Leu Glu Arg Asn His Gly Tyr Pro Ala Arg Glu
    210                 215                 220

Gln Asn Leu Ile Val Tyr Gln Val Gly Thr Glu Cys Phe Thr Gly Gly
225                 230                 235                 240

Pro Ala Arg Phe Thr Cys Arg Asp Phe Arg Ala Asp Leu Trp
                245                 250

<210> SEQ ID NO 22
<211> LENGTH: 247
<212> TYPE: PRT
<213> ORGANISM: Chaetomium brasiliense

<400> SEQUENCE: 22

Met Lys Leu Thr Leu Val Leu Phe Val Ser Ser Leu Ala Ala Ala Thr
1               5                   10                  15

Pro Leu Gly Trp Arg Glu Arg Arg Gln Gln Val Ser Leu Cys Gly Gln
```

-continued

```
                    20                  25                  30
Ser Ser Ser Trp Ser Gly Asn Gly Tyr Gln Leu Asn Asn Asn Leu Trp
            35                  40                  45

Gly Gln Ser Arg Ala Thr Ser Gly Ser Gln Cys Thr Tyr Leu Asp Ser
         50                  55                  60

Ser Ser Asn Ser Gly Ile His Trp His Thr Thr Trp Thr Trp Glu Gly
 65                  70                  75                  80

Gly Glu Gly Glu Val Lys Ser Tyr Ala Tyr Ser Gly Arg Gln Val Ser
                 85                  90                  95

Thr Gly Leu Thr Ile Ala Ser Ile Asp Ser Met Gln Thr Ser Val Ser
             100                 105                 110

Trp Glu Tyr Asn Thr Thr Asp Ile Gln Ala Asn Val Ala Tyr Asp Ile
         115                 120                 125

Phe Thr Ala Glu Asp Pro Asp His Glu His Ser Ser Gly Asp Tyr Glu
     130                 135                 140

Val Met Ile Trp Leu Ala Arg Tyr Asn Asn Val Ser Pro Ile Gly Ser
145                 150                 155                 160

Ser Val Ala Thr Ala Thr Val Gly Gly Asp Thr Trp Asp Leu Phe Ala
                 165                 170                 175

Gly Ala Asn Gly Asp Met Glu Val Tyr Ser Phe Val Ala Glu Asn Thr
             180                 185                 190

Met Asn Ser Phe Ser Gly Asp Val Lys Asp Phe Asp Tyr Leu Glu
         195                 200                 205

Gln Asn Val Gly Phe Pro Val Asp Asp Gln Tyr Leu Leu Val Phe Glu
     210                 215                 220

Leu Gly Ser Glu Ala Phe Thr Gly Gly Pro Ala Thr Leu Ser Val Ser
225                 230                 235                 240

Gln Phe Ser Ala Asn Ile Ala
                 245

<210> SEQ ID NO 23
<211> LENGTH: 357
<212> TYPE: PRT
<213> ORGANISM: Bionectria ochroleuca

<400> SEQUENCE: 23

Met Lys Ser Ile Ile Ser Phe Phe Gly Leu Ala Thr Leu Val Ala Ala
  1               5                  10                  15

Ala Pro Ser Gln Asn Pro Thr Arg Thr Gln Pro Leu Glu Lys Arg Ala
             20                  25                  30

Thr Thr Leu Cys Gly Gln Trp Asp Ser Val Glu Thr Gly Gly Tyr Thr
         35                  40                  45

Ile Tyr Asn Asn Leu Trp Gly Gln Asp Asn Gly Ser Gly Ser Gln Cys
     50                  55                  60

Leu Thr Val Glu Gly Val Thr Asp Gly Leu Ala Ala Trp Ser Ser Thr
 65                  70                  75                  80

Trp Ser Trp Ser Gly Gly Ser Ser Val Lys Ser Tyr Ser Asn Ala
                 85                  90                  95

Val Leu Ser Ala Glu Ala Ala Arg Ile Ser Ala Ile Ser Ser Ile Pro
             100                 105                 110

Ser Lys Trp Glu Trp Ser Tyr Thr Gly Thr Asp Ile Val Ala Asn Val
         115                 120                 125

Ala Tyr Asp Leu Phe Ser Asn Thr Asp Cys Gly Asp Thr Pro Glu Tyr
     130                 135                 140
```

Glu Ile Met Ile Trp Leu Ser Ala Leu Gly Gly Ala Gly Pro Ile Ser
145                 150                 155                 160

Ser Thr Gly Ser Ser Ile Ala Thr Val Thr Ile Ala Gly Ala Ser Trp
            165                 170                 175

Asn Leu Trp Gln Gly Gln Asn Asn Gln Met Thr Val Phe Ser Phe Val
            180                 185                 190

Ala Glu Ser Asp Gln Lys Ser Phe Ser Gly Asp Leu Asn Asp Phe Ile
            195                 200                 205

Gln Tyr Leu Val Asp Ser Gln Gly Tyr Ser Gly Ser Gln Cys Leu Tyr
            210                 215                 220

Ser Ile Gly Ala Gly Thr Glu Pro Phe Thr Gly Thr Asp Ala Glu Phe
225                 230                 235                 240

Ile Thr Thr Gly Tyr Ser Val Ser Val Ser Ala Gly Asp Ser Gly Ser
            245                 250                 255

Asp Glu Thr Thr Thr Ser Ser Gln Ala Gln Ser Ser Thr Val Glu Thr
            260                 265                 270

Ser Thr Ala Thr Gln Pro Gln Ser Ser Ser Thr Val Val Pro Thr Val
            275                 280                 285

Thr Leu Ser Gln Pro Ser Asn Glu Ser Thr Thr Thr Pro Val Gln Ser
290                 295                 300

Gln Pro Ser Ser Val Glu Thr Thr Pro Thr Ala Gln Pro Gln Ser Ser
305                 310                 315                 320

Ser Val Gln Thr Thr Thr Thr Ala Gln Ala Gln Pro Thr Pro Glu Arg
            325                 330                 335

Ala Ala Pro Asp Ala Gly Ser Ala Glu Leu Leu Ser Ser Ala Thr Met
            340                 345                 350

His Leu Asp Arg Arg
            355

<210> SEQ ID NO 24
<211> LENGTH: 247
<212> TYPE: PRT
<213> ORGANISM: Emericella desertorum

<400> SEQUENCE: 24

Met Lys Leu Leu Ala Leu Ser Leu Val Ser Leu Ala Ser Ala Ala Ser
1               5                   10                  15

Ala Ala Ser Ile Leu Ser Asn Thr Phe Thr Arg Arg Ser Asp Phe Cys
            20                  25                  30

Gly Gln Trp Asp Thr Ala Thr Val Gly Asn Phe Ile Val Tyr Asn Asn
            35                  40                  45

Leu Trp Gly Gln Asp Asn Ala Asp Ser Gly Ser Gln Cys Thr Gly Val
    50                  55                  60

Asp Ser Ala Asn Gly Asn Ser Ile Ser Trp His Thr Thr Trp Ser Trp
65                  70                  75                  80

Ser Gly Gly Ser Ser Ser Val Lys Ser Tyr Ala Asn Ala Ala Tyr Gln
                85                  90                  95

Phe Thr Ser Thr Lys Leu Asn Ser Leu Ser Ser Ile Pro Thr Ser Trp
            100                 105                 110

Lys Trp Gln Tyr Ser Thr Thr Asp Ile Val Ala Asn Val Ala Tyr Asp
            115                 120                 125

Leu Phe Thr Ser Ser Ser Ala Gly Gly Asp Ser Glu Tyr Glu Ile Met
            130                 135                 140

Ile Trp Leu Ala Ala Leu Gly Gly Ala Gly Pro Ile Ser Ser Thr Gly
145                 150                 155                 160

-continued

```
Ser Ser Ile Ala Thr Val Thr Leu Gly Gly Val Thr Trp Ser Leu Tyr
            165                 170                 175

Ser Gly Pro Asn Gly Ser Met Gln Val Tyr Ser Phe Val Ala Ser Ser
            180                 185                 190

Thr Thr Glu Ser Phe Ser Ala Asp Leu Met Asp Phe Ile Asn Tyr Leu
            195                 200                 205

Ala Glu Asn Gln Gly Leu Ser Ser Gln Tyr Leu Thr His Val Gln
            210                 215                 220

Ala Gly Thr Glu Pro Phe Thr Gly Thr Asp Ala Thr Leu Thr Val Ser
225                 230                 235                 240

Ser Tyr Ser Val Ser Val Ser
            245

<210> SEQ ID NO 25
<211> LENGTH: 244
<212> TYPE: PRT
<213> ORGANISM: Fusarium solani

<400> SEQUENCE: 25

Met Lys Ser Ala Ile Val Ala Ala Leu Ala Gly Leu Ala Ala Ala Ser
1               5                   10                  15

Pro Thr Arg Leu Ile Pro Arg Gly Gln Phe Cys Gly Gln Trp Asp Ser
            20                  25                  30

Glu Thr Ala Gly Ala Tyr Thr Ile Tyr Asn Asn Leu Trp Gly Lys Asp
            35                  40                  45

Asn Ala Glu Ser Gly Glu Gln Cys Thr Thr Asn Ser Gly Glu Gln Ser
            50                  55                  60

Asp Gly Ser Ile Ala Trp Ser Val Glu Trp Ser Trp Thr Gly Gly Gln
65                  70                  75                  80

Gly Gln Val Lys Ser Tyr Pro Asn Ala Val Val Glu Ile Glu Lys Lys
                    85                  90                  95

Thr Leu Gly Glu Val Ser Ser Ile Pro Ser Ala Trp Asp Trp Thr Tyr
            100                 105                 110

Thr Gly Asn Gly Ile Ile Ala Asn Val Ala Tyr Asp Leu Phe Thr Ser
            115                 120                 125

Ser Thr Glu Ser Gly Asp Ala Glu Tyr Glu Phe Met Ile Trp Leu Ser
            130                 135                 140

Ala Leu Gly Gly Ala Gly Pro Ile Ser Asn Asp Gly Ser Pro Val Ala
145                 150                 155                 160

Thr Val Glu Leu Ala Gly Thr Ser Trp Lys Leu Tyr Gln Gly Lys Asn
            165                 170                 175

Asn Gln Met Thr Val Phe Ser Phe Val Ala Glu Ser Asp Val Asn Asn
            180                 185                 190

Phe Cys Gly Asp Leu Ala Asp Phe Thr Asp Tyr Leu Val Asp Asn His
            195                 200                 205

Gly Val Ser Ser Ser Gln Ile Leu Gln Ser Val Gly Ala Gly Thr Glu
            210                 215                 220

Pro Phe Glu Gly Thr Asn Ala Val Phe Thr Thr Asn Asn Tyr His Ala
225                 230                 235                 240

Asp Val Glu Tyr

<210> SEQ ID NO 26
<211> LENGTH: 250
<212> TYPE: PRT
<213> ORGANISM: Fusarium solani
```

```
<400> SEQUENCE: 26

Met Lys Phe Phe Gly Val Val Ser Ala Phe Leu Ala Ala Thr Ala Val
1               5                   10                  15

Ala Thr Pro Thr Pro Thr Glu Thr Ile Glu Lys Arg Asp Thr Thr
            20                  25                  30

Trp Cys Asp Ala Phe Gly Ser Leu Ala Thr Ser Gly Tyr Thr Val Tyr
        35                  40                  45

His Asn Asn Trp Gly Lys Gly Asp Ala Thr Ser Gly Ser Gln Cys Thr
 50                  55                  60

Thr Phe Thr Ser Val Ser Asn Asn Asn Phe Val Trp Ser Thr Ser Trp
65                  70                  75                  80

Thr Trp Ala Gly Gly Ala Gly Lys Val Lys Ser Tyr Ser Asn Val Ala
                85                  90                  95

Leu Glu Lys Ile Asn Lys Lys Ile Ser Asp Ile Lys Ser Val Ser Thr
            100                 105                 110

Arg Trp Ile Trp Arg Tyr Thr Gly Thr Lys Met Ile Ala Asn Val Ser
        115                 120                 125

Tyr Asp Leu Trp Phe Ala Pro Thr Ala Ser Ser Asn Asn Ala Tyr Glu
130                 135                 140

Ile Met Ile Trp Val Gly Ala Tyr Gly Gly Ala Leu Pro Ile Ser Thr
145                 150                 155                 160

Pro Gly Lys Gly Val Ile Asp Arg Pro Thr Leu Ala Gly Ile Pro Trp
                165                 170                 175

Asp Val Tyr Lys Gly Pro Asn Gly Asp Val Thr Val Ile Ser Phe Val
            180                 185                 190

Ala Ser Ser Asn Gln Gly Asn Phe Gln Ala Asp Leu Lys Glu Phe Leu
        195                 200                 205

Asn Tyr Leu Thr Ser Lys Gln Gly Leu Pro Ser Asn Tyr Val Ala Thr
210                 215                 220

Ser Phe Gln Ala Gly Thr Glu Pro Phe Glu Gly Thr Asn Ala Val Leu
225                 230                 235                 240

Lys Thr Ser Ala Tyr Thr Ile Ser Val Asn
                245                 250

<210> SEQ ID NO 27
<211> LENGTH: 371
<212> TYPE: PRT
<213> ORGANISM: Streptomyces sp. 11AG8

<400> SEQUENCE: 27

Met Arg Ser His Pro Arg Ser Ala Thr Met Thr Val Leu Val Val Leu
1               5                   10                  15

Ala Ser Leu Gly Ala Leu Leu Thr Ala Ala Pro Ala Gln Ala Asn
            20                  25                  30

Gln Gln Ile Cys Asp Arg Tyr Gly Thr Thr Ile Gln Asp Arg Tyr
        35                  40                  45

Val Val Gln Asn Asn Arg Trp Gly Thr Ser Ala Thr Gln Cys Ile Asn
 50                  55                  60

Val Thr Gly Asn Gly Phe Glu Ile Thr Gln Ala Asp Gly Ser Val Pro
65                  70                  75                  80

Thr Asn Gly Ala Pro Lys Ser Tyr Pro Ser Val Tyr Asp Gly Cys His
                85                  90                  95

Tyr Gly Asn Cys Ala Pro Arg Thr Thr Leu Pro Met Arg Ile Ser Ser
            100                 105                 110
```

-continued

```
Ile Gly Ser Ala Pro Ser Ser Val Ser Tyr Arg Tyr Thr Gly Asn Gly
        115                 120                 125

Val Tyr Asn Ala Ala Tyr Asp Ile Trp Leu Asp Pro Thr Pro Arg Thr
130                 135                 140

Asn Gly Val Asn Arg Thr Glu Ile Met Ile Trp Phe Asn Arg Val Gly
145                 150                 155                 160

Pro Val Gln Pro Ile Gly Ser Pro Val Gly Thr Ala His Val Gly Gly
                165                 170                 175

Arg Ser Trp Glu Val Trp Thr Gly Ser Asn Gly Ser Asn Asp Val Ile
            180                 185                 190

Ser Phe Leu Ala Pro Ser Ala Ile Ser Ser Trp Ser Phe Asp Val Lys
        195                 200                 205

Asp Phe Val Asp Gln Ala Val Ser His Gly Leu Ala Thr Pro Asp Trp
    210                 215                 220

Tyr Leu Thr Ser Ile Gln Ala Gly Phe Glu Pro Trp Glu Gly Gly Thr
225                 230                 235                 240

Gly Leu Ala Val Asn Ser Phe Ser Ser Ala Val Asn Ala Gly Gly Gly
                245                 250                 255

Asn Gly Gly Thr Pro Gly Thr Pro Ala Ala Cys Gln Val Ser Tyr Ser
            260                 265                 270

Thr His Thr Trp Pro Gly Gly Phe Thr Val Asp Thr Thr Ile Thr Asn
        275                 280                 285

Thr Gly Ser Thr Pro Val Asp Gly Trp Glu Leu Asp Phe Thr Leu Pro
    290                 295                 300

Ala Gly His Thr Val Thr Ser Val Trp Asn Ala Leu Ile Ser Pro Ala
305                 310                 315                 320

Ser Gly Ala Val Thr Ala Arg Ser Thr Gly Ser Asn Gly Arg Ile Ala
                325                 330                 335

Ala Asn Gly Gly Thr Gln Ser Phe Gly Phe Gln Gly Thr Ser Ser Gly
            340                 345                 350

Ala Gly Phe Thr Ala Pro Ala Gly Ala Arg Leu Asn Gly Thr Ser Cys
        355                 360                 365

Thr Val Arg
    370

<210> SEQ ID NO 28
<211> LENGTH: 221
<212> TYPE: PRT
<213> ORGANISM: Artificial Sequence
<220> FEATURE:
<223> OTHER INFORMATION: consensus sequence
<220> FEATURE:
<221> NAME/KEY: VARIANT
<222> LOCATION: (1)...(221)
<223> OTHER INFORMATION: Xaa = Any Amino Acid

<400> SEQUENCE: 28

Cys Xaa Gln Tyr Xaa Xaa Xaa Xaa Xaa Gly Tyr Xaa Xaa Xaa Asn
1               5                   10                  15

Asn Xaa Trp Gly Xaa Xaa Xaa Xaa Ser Gly Xaa Gln Cys Thr Xaa
                20                  25                  30

Xaa Xaa Xaa Xaa Xaa Xaa Xaa Xaa Xaa Xaa Trp Xaa Xaa Xaa Trp
            35                  40                  45

Xaa Trp Ser Gly Gly Xaa Xaa Xaa Val Lys Ser Tyr Xaa Xaa Xaa Xaa
    50                  55                  60

Xaa Xaa Xaa Xaa Xaa Xaa Xaa Xaa Xaa Xaa Ser Xaa Ile Xaa Ser Xaa
```

```
                65                  70                  75                  80
Xaa Xaa Xaa Xaa Xaa Trp Xaa Tyr Xaa Gly Xaa Xaa Xaa Ala Asn
                        85                  90                  95

Val Ala Tyr Asp Leu Phe Thr Xaa Xaa Xaa Pro Xaa His Xaa Xaa Xaa
            100                 105                 110

Xaa Gly Xaa Tyr Glu Xaa Met Ile Trp Leu Xaa Xaa Xaa Gly Gly Xaa
        115                 120                 125

Xaa Pro Ile Gly Ser Xaa Xaa Xaa Val Xaa Xaa Xaa Xaa Xaa
    130                 135                 140

Gly Xaa Xaa Trp Xaa Leu Xaa Xaa Gly Xaa Asn Gly Xaa Met Xaa Val
145                 150                 155                 160

Xaa Ser Phe Val Ala Xaa Ser Ser Ser Ser Ser Phe Xaa Gly Asp
        165                 170                 175

Xaa Xaa Xaa Phe Xaa Xaa Tyr Leu Xaa Xaa Xaa Xaa Gly Xaa Pro Xaa
            180                 185                 190

Xaa Xaa Gln Tyr Leu Xaa Xaa Xaa Gln Xaa Gly Thr Glu Pro Phe Thr
        195                 200                 205

Gly Xaa Xaa Ala Xaa Xaa Xaa Xaa Xaa Xaa Xaa Ala
    210                 215                 220

<210> SEQ ID NO 29
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 29
gaacgatggc aagggcggcg tgacg                                          25

<210> SEQ ID NO 30
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 30
cttctcgggc tgctacaacc caaacgg                                        27

<210> SEQ ID NO 31
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 31
acatcgtcga gtgttttggc acctac                                         26

<210> SEQ ID NO 32
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 32
catcgtcgag aactggggca cctacaacc                                      29

<210> SEQ ID NO 33
```

```
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 33
ggcacctacc gaccgtccac g                                      21

<210> SEQ ID NO 34
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 34
caagctgggc gagcacacct ccgac                                  25

<210> SEQ ID NO 35
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 35
cgccgcaact gtcgctcgag c                                      21

<210> SEQ ID NO 36
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 36
gtggagggtt accaaagctc tggctctgc                              29

<210> SEQ ID NO 37
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 37
tctggctctg cttgcatcac cgtcagc                                27

<210> SEQ ID NO 38
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 38
gagaagcgcc agtgcattca gcccggc                                27

<210> SEQ ID NO 39
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 39
```
gtgacgtact gcaatggtcc cggcggg                                          27

<210> SEQ ID NO 40
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 40
ggcaccaaga acagggtcat caacttctcg ggc                                   33

<210> SEQ ID NO 41
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 41
tccatcaccg tcagcgatta aaggggctc ttc                                    33

<210> SEQ ID NO 42
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 42
cccagacgat tcagtgcggc acgggctaca ac                                    32

<210> SEQ ID NO 43
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 43
cttctactcg tactggtgcg atggccacgg cg                                    32

<210> SEQ ID NO 44
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 44
cgattcagcc cggctgcggc tacaacaacg gc                                    32

<210> SEQ ID NO 45
<211> LENGTH: 35
<212> TYPE: DNA
<213> ORGANISM: Artificial Sequence
<220> FEATURE:
<223> OTHER INFORMATION: synthetic oligonucleotide

<400> SEQUENCE: 45
caacggctac ttctactgct actggaacga tggcc                                 35

<210> SEQ ID NO 46
<211> LENGTH: 34
<212> TYPE: DNA

<210> SEQ ID NO 47
<211> LENGTH: 31
<212> TYPE: DNA
<213> ORGANISM: Artificial Sequence
<220> FEATURE:
<223> OTHER INFORMATION: synthetic oligonucleotide

<400> SEQUENCE: 46
ccggcacggg ctactgcaac ggctacttct actc                                    34

<210> SEQ ID NO 47
<211> LENGTH: 31
<212> TYPE: DNA
<213> ORGANISM: Artificial Sequence
<220> FEATURE:
<223> OTHER INFORMATION: synthetic oligonucleotide

<400> SEQUENCE: 47
ggcgtgacgt acacctgcgg tcccggcggg c                                       31

<210> SEQ ID NO 48
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 48
ggcgccacca agtgcggcga ggtcacc                                            27

<210> SEQ ID NO 49
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 49
gcgtgggctc agtgcggcct gacgctcg                                           28

<210> SEQ ID NO 50
<211> LENGTH: 752
<212> TYPE: DNA
<213> ORGANISM: Trichoderma reesei

<400> SEQUENCE: 50
atggttgcct tttccagcct catctgcgct ctcaccagca tcgccagtac tctggcgatg        60
cccacaggcc tcgagcctga gagcagtgtc aacgtcacag agcgtggcat gtacgacttt       120
gttcttggag ctcacaatga tcatcgccgt cgtgctagca tcaactacga ccaaaactac       180
caaactggcg gacaagtcag ctattcgcct tccaacactg gcttctcagt gaactggaac       240
actcaagatg actttgttgt gggcgttggt tggacgactg gatcttctgc gtaggaggac       300
tcctcatcat tctgcacttt gaaagcatct tctgaccaaa agcttctctt agtcccatca       360
actttggcgg ctcttttagt gtcaacagcg gaactggcct gctttccgtc tatggctgga       420
gcaccaaccc actggttgag tactacatca tggaggacaa ccacaactac ccagcacagg       480
gtaccgtcaa gggaaccgtc accagcgacg gagccactta ccatctctgg gagaataccc       540
gtgtcaacga gccttccatc agggcacag cgaccttcaa ccagtacatt tccgtgcgga        600
actcgcccag gaccagcgga actgttactg tgcagaacca cttcaatgct gggcctcgc        660 ttggcctgca ccttgggcag atgaactacc aggttgtcgc tgtcgaaggc tggggtggta       720
gtggttctgc ctcacagagt gtcagcaact ag                                    752

```
-continued

<210> SEQ ID NO 51
<211> LENGTH: 248
<212> TYPE: PRT
<213> ORGANISM: Trichoderma reesei

<400> SEQUENCE: 51

Met Val Ala Phe Ser Ser Leu Ile Cys Ala Leu Thr Ser Ile Ala Ser
 1               5                  10                  15

Thr Leu Ala Met Pro Thr Gly Leu Glu Pro Glu Ser Ser Val Asn Val
             20                  25                  30

Thr Glu Arg Gly Met Tyr Asp Phe Val Leu Gly Ala His Asn Asp His
         35                  40                  45

Arg Arg Arg Ala Ser Ile Asn Tyr Asp Gln Asn Tyr Gln Thr Gly Gly
     50                  55                  60

Gln Val Ser Tyr Ser Pro Ser Asn Thr Gly Phe Ser Val Asn Trp Asn
 65                  70                  75                  80

Thr Gln Asp Asp Phe Val Val Gly Val Gly Trp Thr Thr Gly Ser Ser
                 85                  90                  95

Ala Glu Asp Ser Ser Ser Phe Cys Thr Leu Lys Ala Ser Ser Asp Gln
            100                 105                 110

Lys Leu Leu Leu Val Pro Ser Thr Leu Ala Ala Leu Leu Val Ser Thr
        115                 120                 125

Ala Glu Leu Ala Cys Phe Pro Ser Met Ala Gly Ala Pro Thr His Trp
    130                 135                 140

Leu Ser Thr Thr Ser Trp Arg Thr Thr Thr Thr Thr Gln His Arg Val
145                 150                 155                 160

Pro Ser Arg Glu Pro Ser Pro Ala Thr Glu Pro Leu Thr Pro Ser Gly
                165                 170                 175

Arg Ile Pro Val Ser Thr Ser Leu Pro Ser Arg Ala Gln Arg Pro Ser
                180                 185                 190

Thr Ser Thr Phe Pro Cys Gly Thr Arg Pro Gly Pro Ala Glu Leu Leu
            195                 200                 205

Leu Cys Arg Thr Thr Ser Met Leu Gly Pro Arg Leu Ala Cys Thr Leu
    210                 215                 220

Gly Arg Thr Thr Arg Leu Ser Leu Ser Lys Ala Gly Val Val Val Val
225                 230                 235                 240

Leu Pro His Arg Val Ser Ala Thr
                245
```

US 7,314,743 B2

MODIFIED ENZYMES, METHODS TO PRODUCE MODIFIED ENZYMES AND USE THEREOF

This application is a 371 US filing of PCT/US04/29575 filed on Sep. 10, 2004, which claims benefit of U.S. provisional application 60/503,251 filed on Sep. 15, 2003.

FIELD OF THE INVENTION

The invention is directed to modified enzymes having increased stability in harsh industrial environments, such as increased pH and/or temperature.

BACKGROUND OF THE INVENTION

Xylanases have been found in at least a hundred different organisms. Xylanases are glycosyl hydrolases which hydrolyse β-1,4-linked xylopyranoside chains. Within the sequence-based classification of glycosyl hydrolase families established by Henrissat and Bairoch (1993), most xylanases are found in families 10 and 11. Common features for family 11 members include high genetic homology, a size of about 20 kDa and a double displacement catalytic mechanism (Tenkanen et al., 1992; Wakarchuk et al., 1994). The families have now been grouped, based on structure similarities, into Clans (Henrissat and Davies, 1995). Family 11 glycosyl hydrolases, which are primarily xylanases, reside in Clan C along with family 12 enzymes, all of which are known to be cellulases.

Xylanases can be often used for important applications such as the bleaching of pulp, modification of textile fibers and in animal feed (e.g., xylanases can aid animal digestion, Prade, 1996). Xylanases are useful for production of human foods as well. For example, xylanase improves the properties of bread dough and the quality of bread. Xylanases can also aid the brewing process by improving filterability of xylan containing beers. Xylanases can be employed in the decomposition of vegetative matter including disposal/use of agricultural waste and waste resulting from processing of agricultural products, including production of fuels or other biobased products/materials from biomass.

Often, however, extreme conditions in these applications, such as high temperature and/or pH, etc, render the xylanases less effective than under normal conditions. During pulp bleaching, for example, material that comes from an alkaline wash stage can have a high temperature, sometimes greater than 80° C., and a high pH, such as a pH greater than 10. Since most xylanases do not function well under those conditions, pulp must be cooled and the alkaline pH neutralized before the normal xylanase can function. Taking some of these steps into account, the process can become more expensive since it must be altered to suit the xylanase.

In another example, xylanases are also useful in animal feed applications. There, the enzymes can face high temperature conditions for a short time (e.g. ~0.5-5 min at 95° C. or higher) during feed preparation. Inactivation of the enzyme can occur under these temperature conditions, and the enzymes are rendered useless when needed at a lower temperature such as, for example, ~37° C.

Xylanases with improved qualities have been found. Several thermostable, alkalophilic and acidophilic xylanases have been found and cloned from thermophilic organisms (Bodie et al., 1995; Fukunaga et al., 1998). However, it is often difficult to produce the enzymes in economically efficient quantities. *T. reesei*, on the other hand, produces xylanases, which are not as thermostable as xylanases from thermophilic organisms. *T. reesei* is known to produce different xylanases of which xylanases I and II (XynI and XynII, respectively) are the best characterized (Tenkanen et al., 1992). XynI has a size of 19 kDa, a pI of 5.5 and a pH of between 3 and 4. XynII has a size of 20 kDa, a pI of 9.0 and a pH optimum of 5.0-5.5 (Törrönen and Rouvinen, 1995). These xylanases exhibit a favorable pH profile, specificity and specific activity in a number of applications, and can be produced economically in large-scale production processes.

Efforts have been made to engineer a xylanase with favorable qualities. For example, some have tried to improve the stability of the *Bacillus circulans* xylanase by adding disulphide bridges which bind the N-terminus of the protein to the C-terminus and the N-terminal part of the α-helix to the neighbouring β-strand (Wakarchuk et al., 1994). Also, Campbell et al. (1995) modified *Bacillus circulans* xylanase by inter- and intramolecular disulphide bonds in order to increase thermostability. Similarly, the stability of *T. reesei* xylanase II has been improved by changing the N-terminal region to a respective part of a thermophilic xylanase (Sung et al., 1998). In addition to the improved thermostability, the activity range of the enzyme was broadened to include an alkaline pH. Single point mutations have also been used to increase the stability of *Bacillus pumilus* xylanase (Arase et al., 1993).

By comparing the structures of thermophilic and mesophilic enzymes much information has been obtained (Vogt et al., 1997). Structural analysis of thermophilic xylanases has also given information about factors influencing the thermostability of xylanases (Gruber et al., 1998; Harris et al., 1997).

Currently, however, there is a need for enzymes, especially xylanases, with improved properties in industrial conditions.

SUMMARY OF THE INVENTION

The current invention relates to modified enzymes. Specifically, the invention relates to modified enzymes with improved performance at extreme conditions of pH and temperature. The modification or substitution is numbered from the amino acid after the signal and pro sequence. The signal and pro sequences end at amino acid 33 in SEQ ID NO:1.

In a first aspect, the invention is drawn to a modified xylanase comprising a polypeptide having an amino acid sequence as set forth in SEQ ID NO:1, wherein the sequence has at least one substituted amino acid residue at a position selected from the group consisting of: 2, 5, 7, 10, 11, 16, 19, 22, 26, 28, 29, 30, 34, 36, 38, 57, 58, 61, 63, 65, 67 92, 93, 97, 105, 108, 110, 111, 113, 132, 143, 144, 147, 149, 151, 153, 157, 160, 162, 165, 169, 180, 184, 186, 188, 190 and +191, wherein the position of the substituted amino acid is numbered from the amino acid after the signal and pro sequence. Preferably, the substitution is selected from the group consisting of: 2, 22, 28, 58, 65, 92, 93, 97, 105, 108, 144, 162, 180, 186 and +191. Preferably, the modified xylanase has at least one substitution selected from the group consisting of: H22K, S65C, N92C, F93W, N97R, V108H, H144C, H144K, F180Q and S186C. Also, preferably, the modified xylanase exhibits Improved thermophilicity, alkaliphilicity or a combination thereof, in comparison to a wild-type xylanase.

In a second aspect, the invention is drawn to a modified enzyme, the modified enzyme comprising an amino acid sequence, the amino acid sequence being homologous to the sequence set forth in SEQ ID NO:1, the amino acid sequence having at least one substituted amino acid residue at a position equivalent to a position selected from the group consisting of: 2, 5, 7, 10, 11, 16, 19, 22, 26, 28, 29, 30, 34, 36, 38, 57, 58, 61, 63, 65, 67, 92, 93, 97, 105, 108, 110, 111, 113, 132, 143, 144, 147, 149, 151, 153, 157, 160, 162, 165, 169, 180, 184, 186, 188, 190 and +191. In a preferred embodiment, the amino acid sequence has at least one substituted amino acid residue at a position equivalent to a position selected from the group consisting of: 2, 22, 28, 58, 65, 92, 93, 97, 105, 108, 144, 162, 180, 186 and +191. In a preferred embodiment, the amino acid sequence has at least one substituted amino acid residue selected from the group consisting of: H22K, S65C, N92C, F93W, N97R, V108H, H144C, H144K, F180Q and S186C.

In a preferred embodiment of the invention, the modified enzyme is a glycosyl hydrolase of Clan C comprising an amino acid sequence, the amino acid sequence being homologous to the sequence set forth in SEQ ID NO:1 the amino acid sequence having at least one substituted amino acid residue at a position equivalent to a position selected from the group consisting of: 2, 5, 7, 10, 11, 16, 19, 22, 26, 28, 29, 30, 34, 36, 38, 57, 58, 61, 63, 65, 67, 92, 93, 97, 105, 108, 110, 111, 113, 132, 143, 144, 147, 149, 151, 153, 157, 160, 162, 165, 169, 180, 184, 186, 188, 190 and +191. In a preferred embodiment, the amino acid sequence has at least one substituted amino acid residue at a position equivalent to a position selected from the group consisting of: 2, 22, 28, 58, 65, 92, 93, 97, 105, 108, 144, 162, 180, 186 and +191. In a preferred embodiment, the amino acid sequence has at least one substituted amino acid residue selected from the group consisting of: H122K, S65C, N92C, F93W, N97R, V108H, H144C, H144K, F180Q and S186C. Preferred modified enzymes are as disclosed herein.

In a preferred embodiment, the modified enzyme is a family 11 xylanase comprising is an amino acid sequence, the amino acid sequence being homologous to the sequence set forth in SEQ ID NO:1, the amino acid sequence having at least one substituted amino acid residue at a position equivalent to a position selected from the group consisting of: 2, 5, 7, 10, 11, 16, 19, 22, 26, 28, 29, 30, 34, 36, 38, 57, 58, 61, 63, 65, 67, 92, 93, 97, 105, 108, 110, 111, 113, 132, 143, 144, 147, 149, 151, 153, 157, 160, 162, 165, 169, 180, 184, 186, 188, 190 and +191. In a preferred embodiment, the amino acid sequence has at least one substituted amino acid residue at a position equivalent to a position selected from the group consisting of: 2, 22, 28, 58, 65, 92, 93, 97, 105, 108, 144, 162, 180, 186 and +191. In a preferred embodiment, the amino acid sequence has at least one substituted amino acid residue selected from the group consisting of: H22K, S65C, N92C, F93W, N97R, V108H, H144C, H144K, F180Q and S186C. Preferred modified family 11 enzymes are as disclosed herein.

In another preferred embodiment, the modified enzyme is a family 12 cellulase comprising an amino acid sequence, the amino acid sequence being homologous to the sequence set forth in SEQ ID NO:1, the amino acid sequence having at least one substituted amino acid residue at a position equivalent to a position selected from the group consisting of: 2, 5, 7, 10, 11, 16, 19, 22, 26, 28, 29, 30, 34, 36, 38, 57, 58, 61, 63, 65, 67, 92, 93, 97, 105, 108, 110, 111, 113, 132, 143, 144, 147, 149, 151, 153, 157, 160, 162, 165, 169, 180, 184, 186, 188, 190 and +191. In a preferred embodiment, the amino acid sequence has at least one substituted amino acid residue at a position equivalent to a position selected from the group consisting of: 2, 22, 28, 58, 65, 92, 93, 97, 105, 108, 144, 162, 180, 186 and +191. In a preferred embodi-
ment, the amino acid sequence has at least one substituted amino acid residue selected from the group consisting of: H22K, S65C, N92C, F93W, N97R, V108H, H144C, H144K, F180Q and S186C, wherein the position is an equivalent position, as defined herein. Preferred family 12 modified enzymes are as disclosed herein.

In a preferred embodiment, the family 12 cellulase is *Trichoderma* EGIII cellulase as set forth in SEQ ID NO:3, the modification comprises at least one amino acid selected from the group consisting of: 2, 13, 28, 34, 77, 80, 86, 122, 123, 134, 137, 140, 164, 174, 183, 209, 215 and 218, the position numbering being with respect to SEQ ID NO:3. In a preferred embodiment, the substitution is at least one mutation selected from the group consisting of T2C, N13H, S28K, T34C, S77C, P80R, S86C, G122C, K123W, Q134H, Q134K, Q134R, V137H, G140C, N164C, N164K, N174C, K183H, N209C, A215D and is N218C, position numbering being with respect to SEQ ID NO:3.

Embodiments of the first and second aspects of the invention, as disclosed above, also pro vide for nucleic acids encoding any of the modified enzymes, as set forth above, as well as complements. In another preferred embodiment, the invention provides for compositions comprising at least one modified enzyme, as disclosed herein, and another ingredient. In another preferred embodiment, the invention provides vectors comprising a modified enzyme, as disclosed herein, cells comprising the modified enzyme and methods of expressing the modified enzyme.

In a third aspect, the invention is drawn to a method of modifying an enzyme comprising modifying a first site in the enzyme so that the first site can bind to a second site in the enzyme. In a preferred embodiment, the first site is in a loop or sequence adjacent to a β-sheet. In a preferred embodiment, the second site is located in a β-sheet.

In a preferred embodiment, the modified enzyme is a xylanase. For example, in a preferred embodiment; the invention is drawn to a modified xylanase, wherein the xylanase is modified by at least one of the following methods: (i) by modifying an N-terminal sequence so that the N-terminal sequence is bound by a disulphide bridge to an adjacent β-strand; (ii) by modifying a C-terminal sequence so that the C-terminal sequence is bound to an adjacent β-strand; (iii) by modifying an α-helix or sequence adjacent to an α-helix, so that the α-helix, or sequence adjacent to the α-helix, is bound more tightly to the body of the protein; (iv) by modifying a sequence adjacent to the β-strand so that the sequence adjacent to the β-strand can be bound more tightly to an adjacent sequence. For example, in a preferred embodiment, modification can occur in a β-strand next to the cord.

BRIEF DESCRIPTION OF FIGURES

FIG. 1 shows an amino acid alignment among family 11 xylanases. The amino acid numbering is compared with *T. Reesei* Xylanase II, as indicated at the top of the sequences. The residues common to at least 75% of family 11 xylanases are underlined. The following are aligned (by abbreviation) in the figure: XYN2_TRIRE Endo-1,4-beta-xylanase 2 precursor (EC 3.2.1.8) (Xylanase 2) (1,4-beta-D-xylan xylanohydrolase 2)—*Trichoderma reesei* (*Hypocrea jecorina*)>sp|P36217|; XYN1_TRIRE Endo-1,4-beta-xylanase 1 precursor (EC 3.2.1.8) (Xylanase 1) (1,4-beta-D-xylan xylanohydrolase 1)—*Trichoderma reesei* (*Hypocrea jecorina*)>sp|P36218|; XYN2_BACST Endo-1,4-beta-xylanase precursor (EC 3.2.1.8) (Xylanase) (1,4-beta-D-xylan xylanohydrolase)—*Bacillus stearothermophilus*>sp|P45703|;

XYN1_HUMIN Endo-1,4-beta-xylanase 1 precursor (EC 3.2.1.8) (Xylanase 1) (1,4-beta-D-xylanxylanohydrolase 1)—*Humicola insolens*>sp|P55334|; XYN1_ASPAW Endo-1,4-beta-xylanase I precursor (EC 3.2.1.8) (Xylanase I) (1,4-beta-D-xylan xylanohydrolase I)—*Aspergillus awamori*>sp|P55328|; XYNA_BACST Endo-1,4-beta-xylanase A precursor (EC 3.2.1.8) (Xylanase A) (1,4-beta-D-xylan>sp|P45705|.

Figure 2:
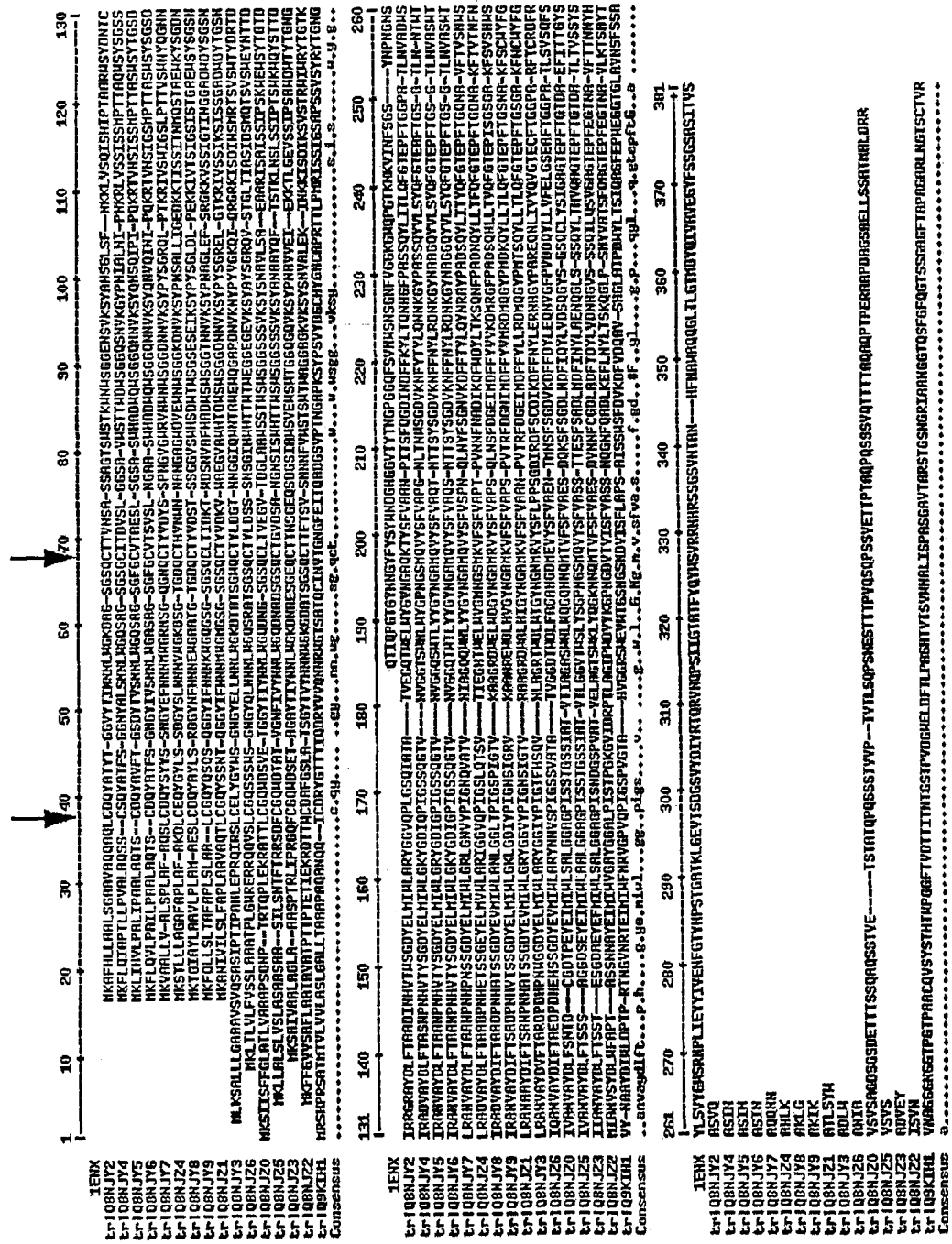

FIG. 2 shows an amino acid alignment of family 12 Cellulases with XynII. The following are aligned (by abbreviation) in the figure: 1ENX XylanaseII *Trichoderma reesei*, and cel12 family members Q8NJY2 *Aspergillus awamori*, Q8NJY3 *Humnicola grisea*, Q8NJY4 *Trichoderma viride*, Q8NJY5 *Hypocrea koningii*, Q8NJY6 *Hypocrea schweinitzii*, Q8NJY7 *Stachybotrys echinata*, Q8NJY8 *Bionectria ochroleuca*, Q8NJY9 *Bionectria ociroleuca*, Q8NJZ0 *Bionectria ochroleuca*, Q8NJZ1 *Bionectria ochroleuca*, Q8NJZ2 *Fusariuin solaini* (subsp. *Cucurbitae*), Q8NJZ3 *Fusariumlt solaini* (subsp. *cucurbitae*), Q8NJZ4 *Fusarium equiseti* (*Fusarium scirpi*), Q8NJZ5 *Emericella desertorum*, Q8NJZ6 *Chaetomium brasiliense*, Q9KIH1 *Streptomyces* sp. 11AG8. In the Figure, the two arrows indicates the position of the disulphide bridges (signal sequence not removed).

FIG. 3 shows the nucleotide sequence of the *Trichoderma reesei* oligonucleotides used in mutagenesis of the xylanase, with the codon changes underlined.

Figure 4:
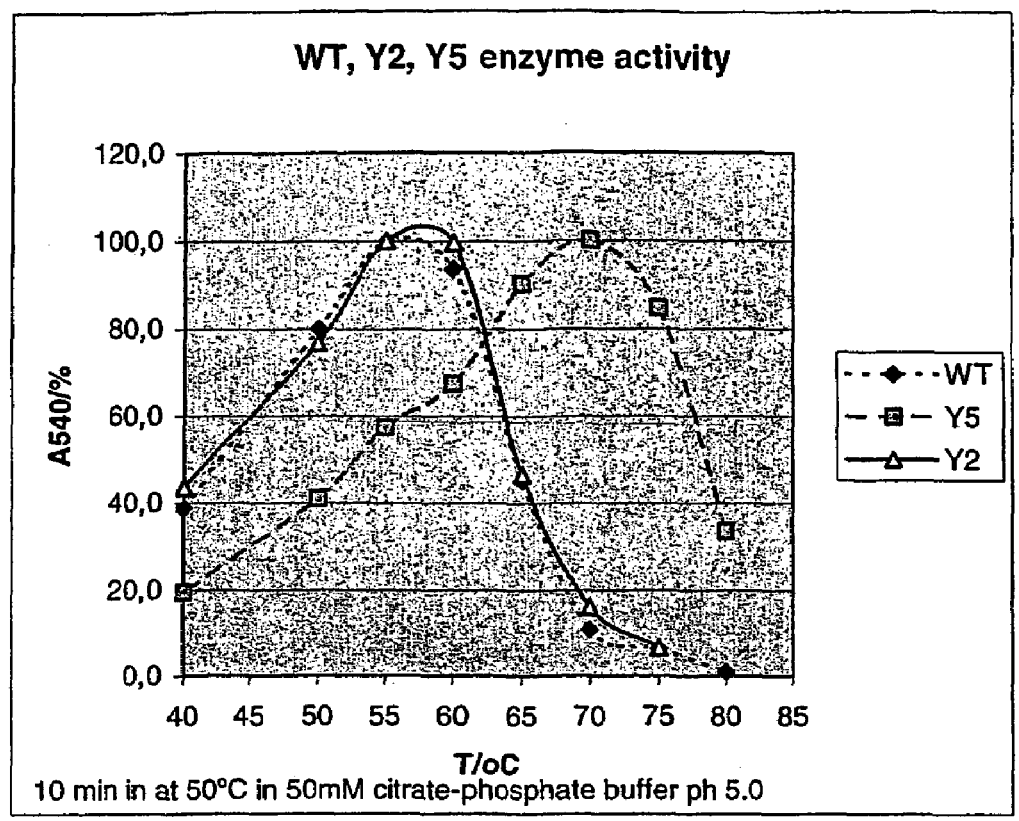

FIG. 4 shows a graph comparing activity with respect to temperature of the wild-type XynII with the Y2 and Y5 mutated xylanases. Mutated xylanases have the following mutations: K58R and an aspartic acid added to the C-terminal serine at position 190 (+191D)(=Y2); T2C, T28C, K58R+191D, (=Y5). The figure exemplifies that a salt bridge, alone, does not increase thermophilicity and thermal stability. Rather, introduction of a disulphide bridge increases stability and temperature dependent activity. Activity is measured as per Bailey at el., 1992.

Figure 5:
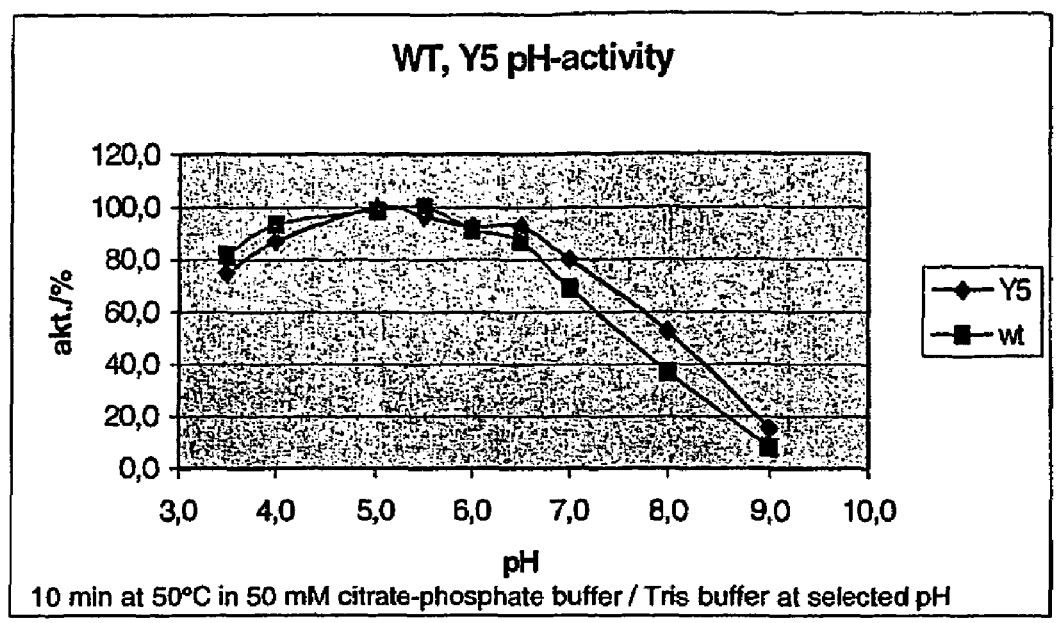

FIG. 5 shows a graph comparing the activity with respect to pH of the XynII wild-type with the Y5 mutated xylanase with the following mutations: T2C, T28C, K58R with an added aspartic acid added to the C-terminal serine position 190 (+191D). Activity is measured as per Bailey et al., 1992

Figure 6:
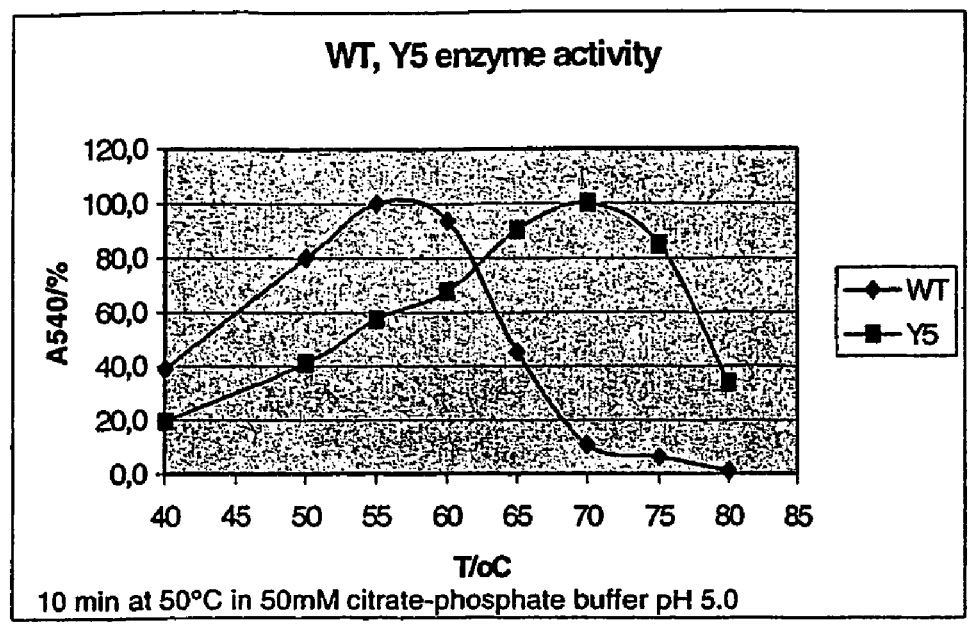

FIG. 6 shows a graph comparing the activity with respect to temperature of the is XynI wild-type with the Y5 mutated xylanase with the following mutations: T2C, T28C, K58R with an added aspartic acid added to the C-terminal serine position 190 (+191D). Activity is measured as per Bailey et al., 1992.

Figure 7:
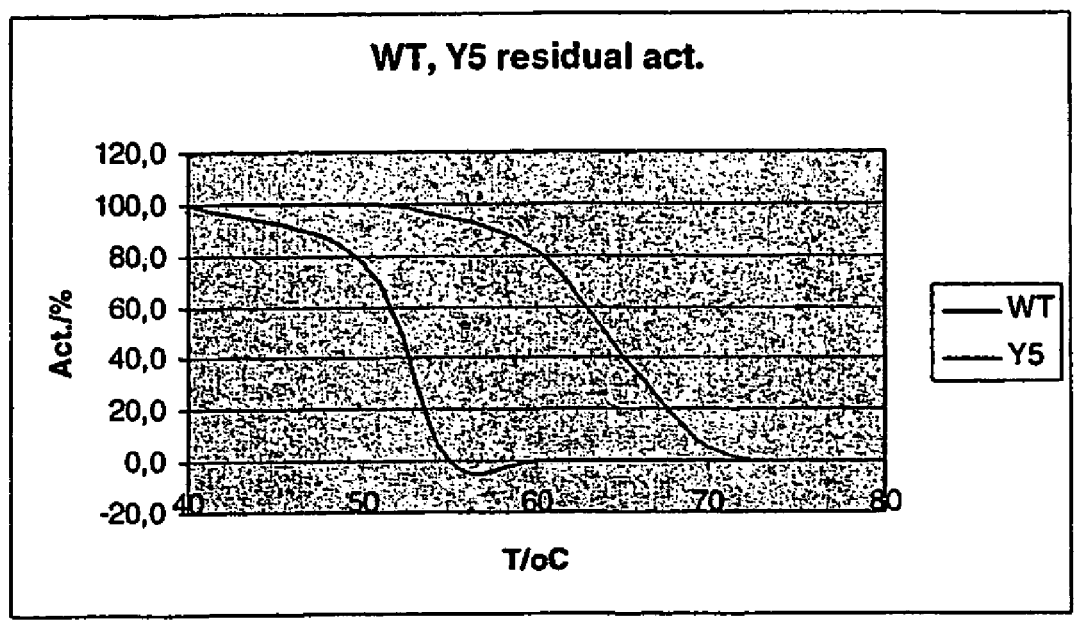

FIG. 7 shows a graph comparing the residual activity at pH 5.0, with inactivation at pH 8 with respect to temperature of the wild type XynII xylanase with the Y5 mutated xylanase having the following mutations: T2C, T28C, K58R with an added aspartic acid added to the C-terminal serine position 190 (+191D). Activity is measured as per Bailey et al., 1992.

Figure 8:
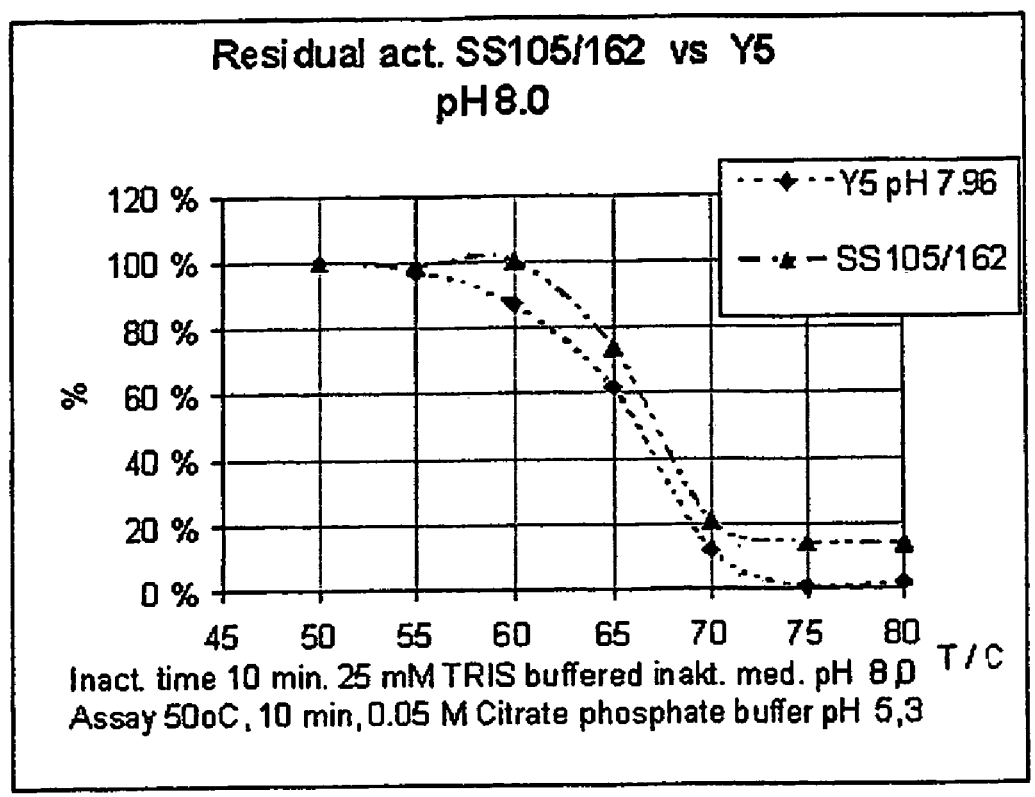

FIG. 8 shows a graph comparing the residual activity at pH 5.3, with inactivation at pH 8 with respect to temperature of the Y5 mutated xylanase with a XynII xylanase (SS105/162) having the following additional mutations Q162C and L105C. Activity is measured as per Bailey et al., 1992.

Figure 9:
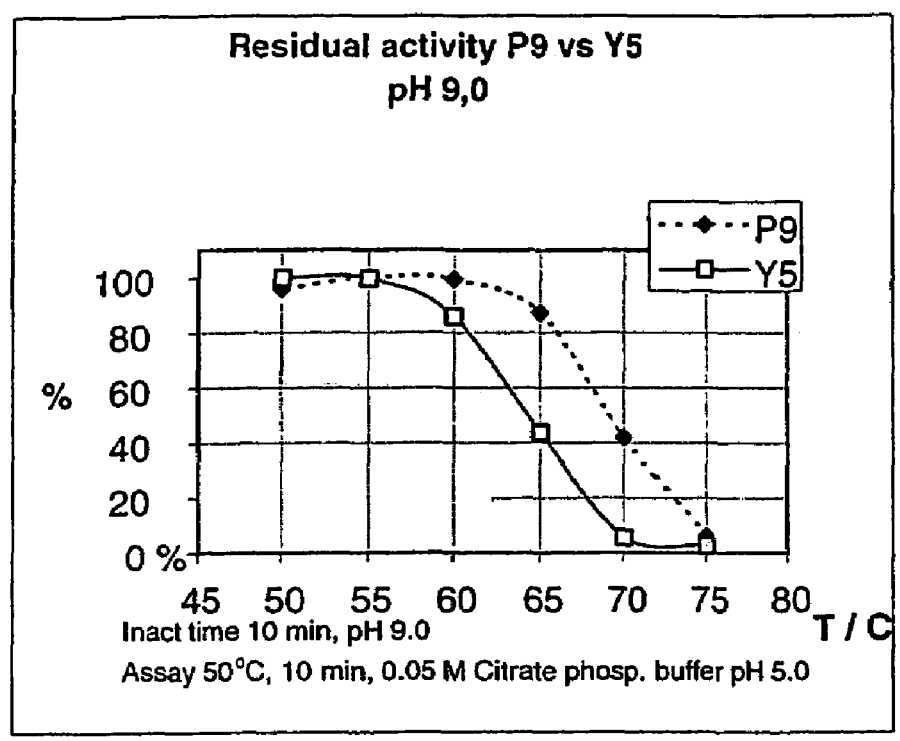

FIG. 9 shows a graph comparing the residual activity at pH 5, with inactivation at pH 9 with respect to temperature of the Y5 mutated xylanase with a XynII xylanase (P9) having the following additional mutations: F93W, N97R and H144K. Activity is measured as per Bailey et al., 1992.

Figure 10:
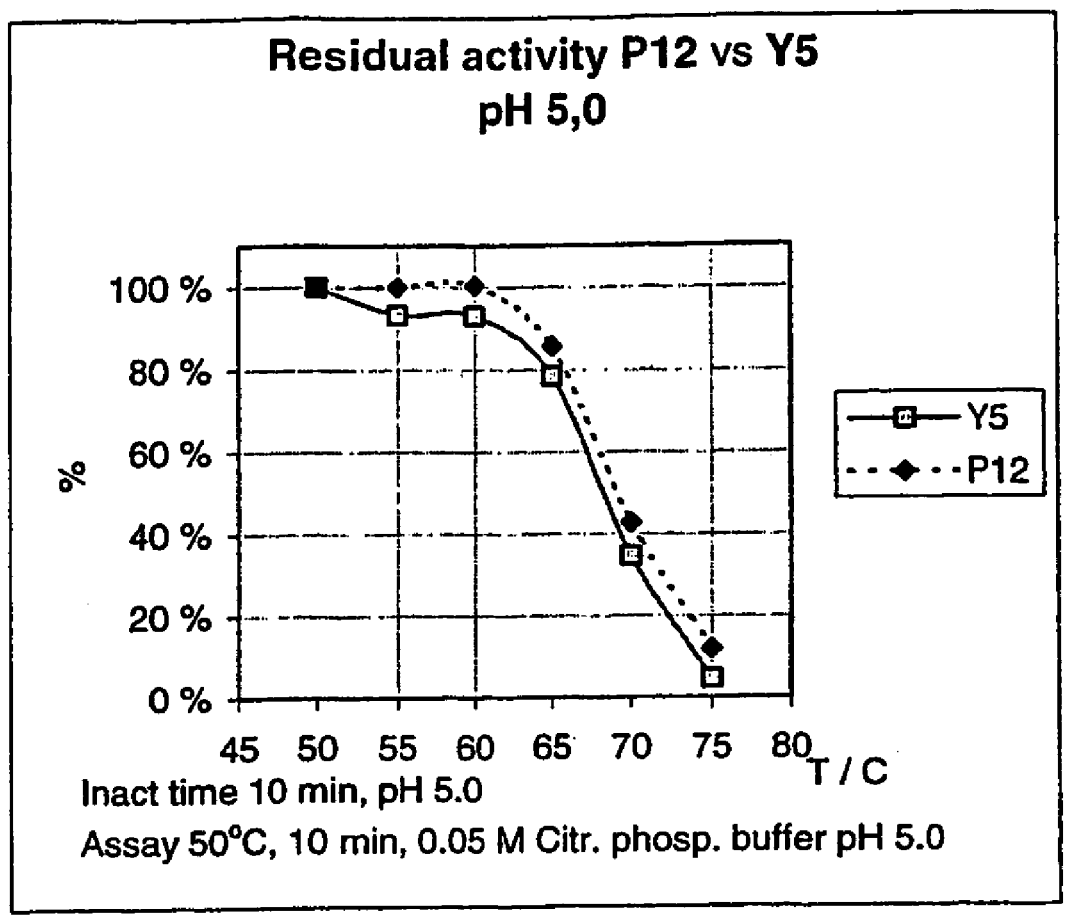

FIG. 10 shows a graph comparing the residual activity at pH 5, with inactivation at pH 5 with respect to temperature of the Y5 mutated xylanase with a XynII xylanase (P12) having the following additional mutations H144C and N92C. Activity is measured as per Bailey et al., 1992.

Figure 11:
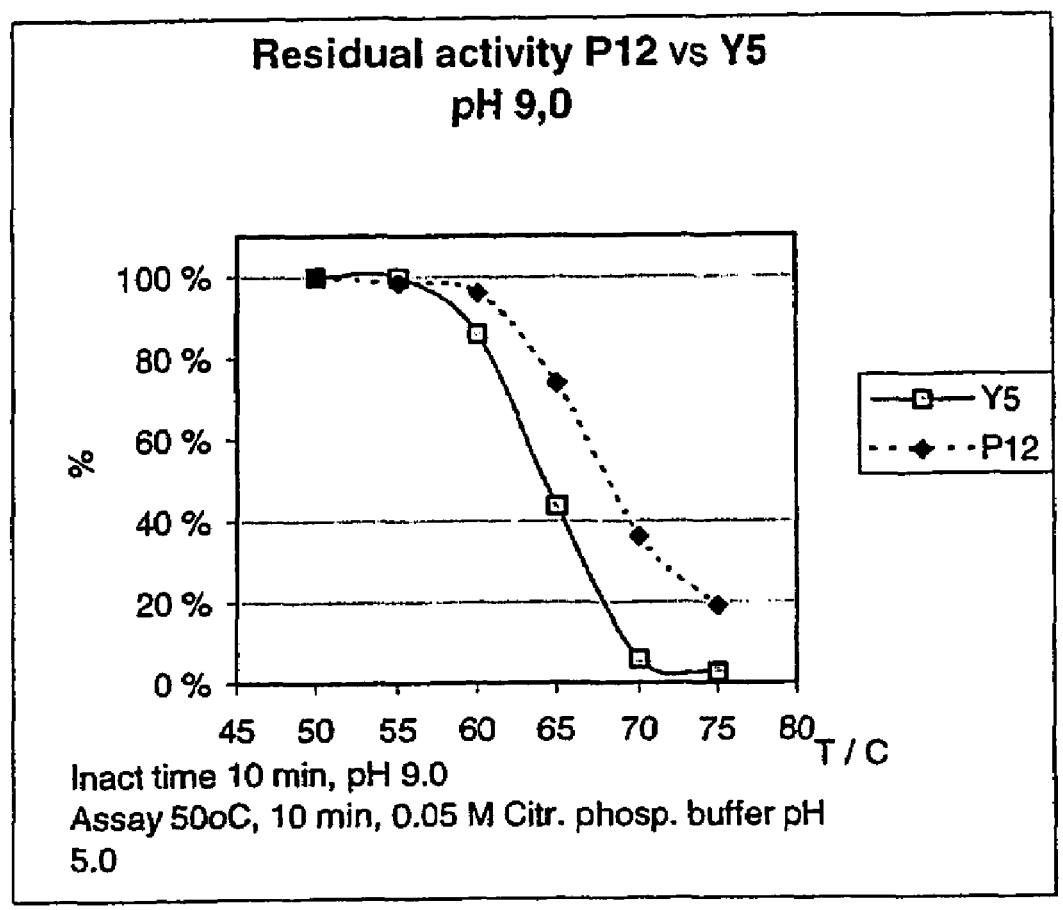

FIG. 11 shows a graph comparing the residual activity at pH 5, with inactivation at pH 9 with respect to temperature of the Y5 mutated xylanase with a XynII xylanase (P12) having the following additional mutations H144C and N92C. Activity is measured as per Bailey et al., 1992.

Figure 12:
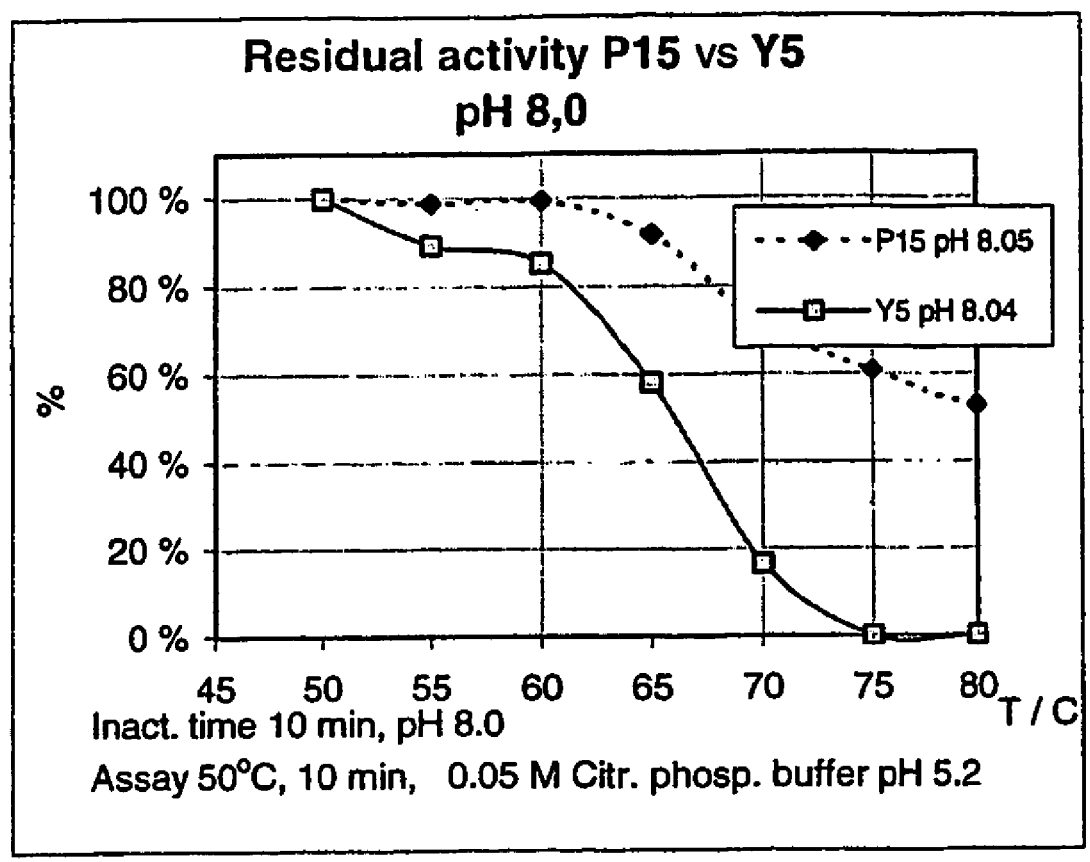

FIG. 12 shows a graph comparing the residual activity at pH 5.2, with inactivation at pH 8 with respect to temperature of the Y5 mutated xylanase with a XynII (P15) xylanase having the following additional mutations: F180Q, H144C and N92C. Activity is measured as per Bailey et al., 1992.

Figure 13:
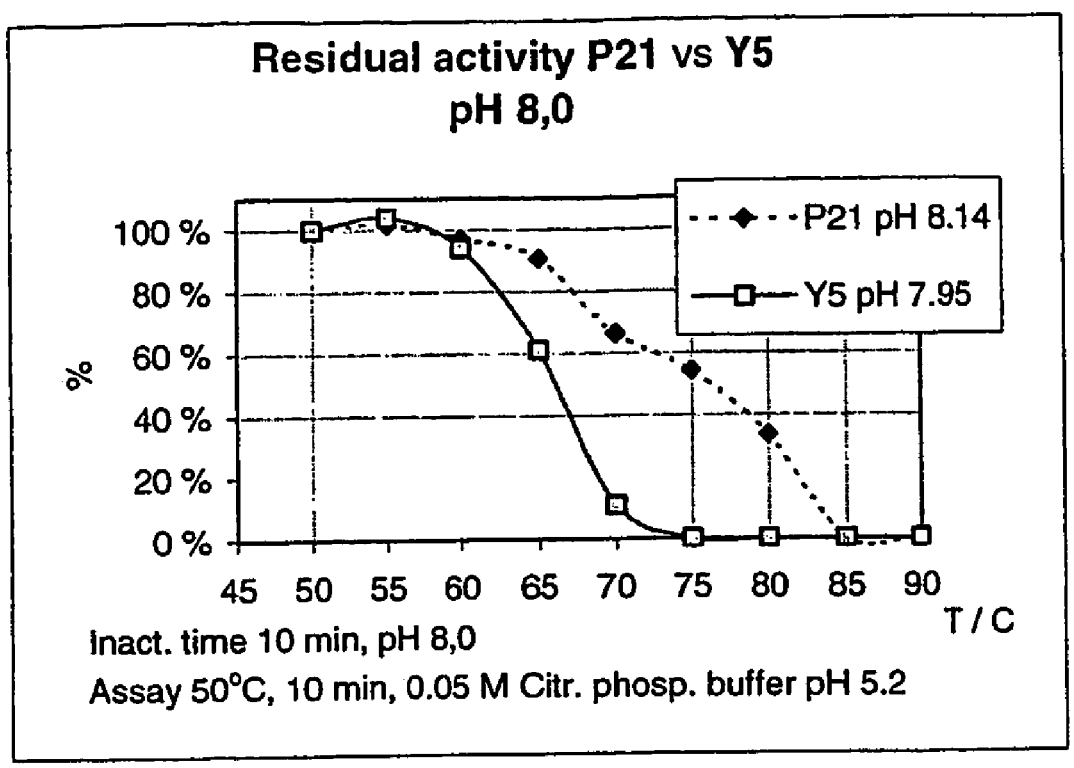

FIG. 13 shows a graph comparing the residual activity at pH 5, with inactivation at pH 8 with respect to temperature of the Y5 mutated xylanase with a XynII xylanase (P21) having the following additional mutations: H22K, F180Q, H144C and N92C. Activity is measured as per Bailey et al., 1992.

Figure 14:
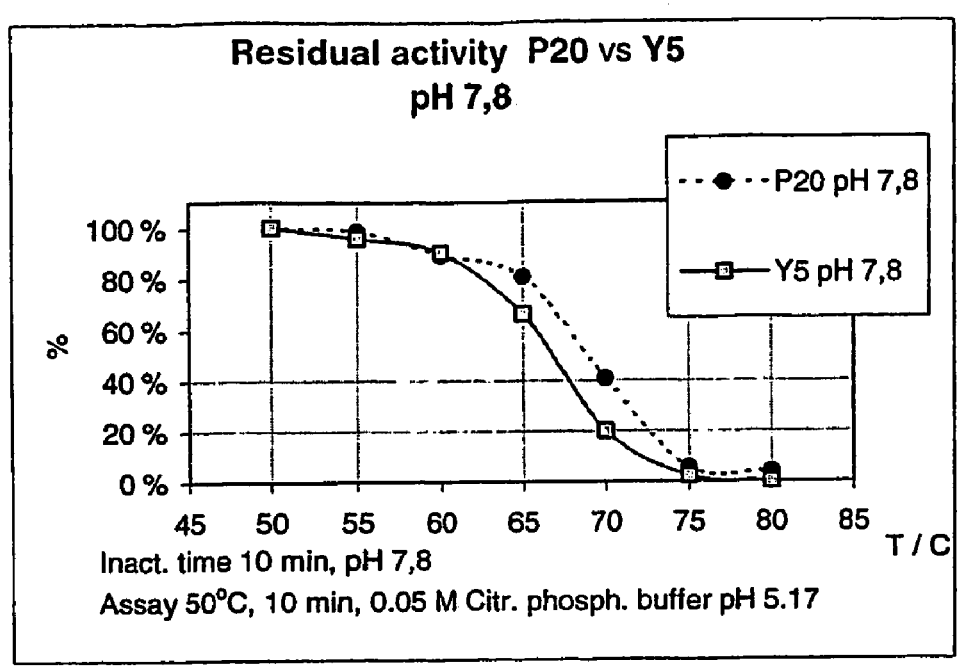

FIG. 14 shows a graph comparing the residual activity at pH 5.17 with inactivation at pH 7.8, with respect to temperature of the Y5 mutated xylanase with a XynII xylanase (P20) having the following additional mutations: H22K and F180Q. Activity is measured as per Bailey et al., 1992.

Figure 15:
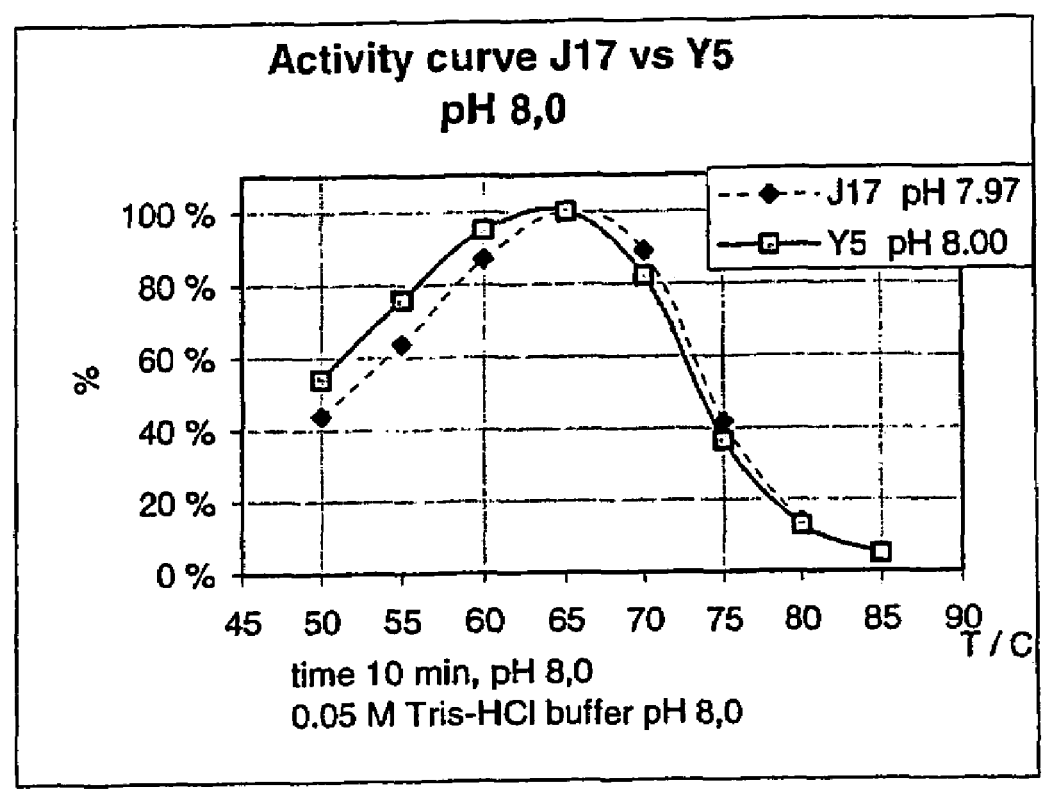

FIG. 15 shows a graph comparing the activity at pH 8 with respect to temperature of the Y5 mutated xylanase with a XynII xylanase (J17) having the following additional mutation: V108H. Activity is measured as per Bailey et al., 1992.

Figure 16:
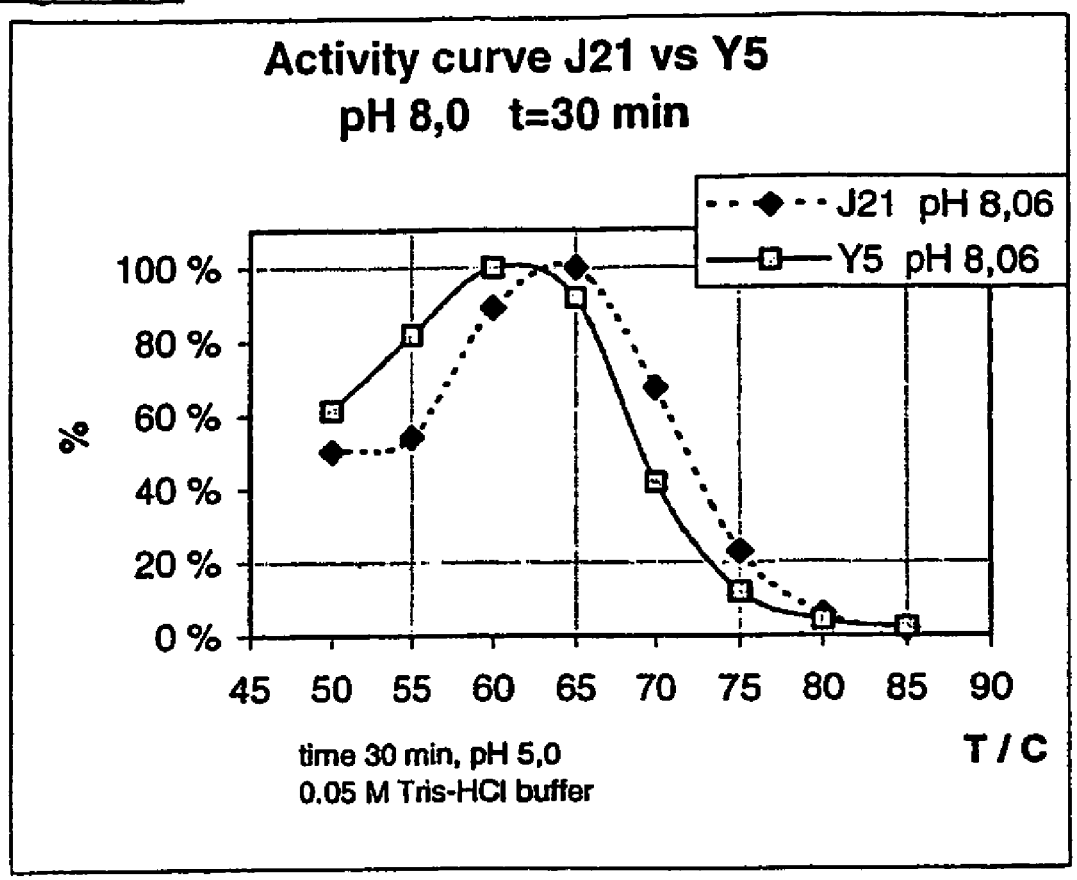

FIG. 16 shows a graph comparing the activity at pH 8 with respect to temperature of the Y5 mutated xylanase with a XynII xylanase (J21) having the following additional mutations: S65C and S186C (J21 in the graph). Activity is measured as per Bailey et al., 1992.

Figure 17:
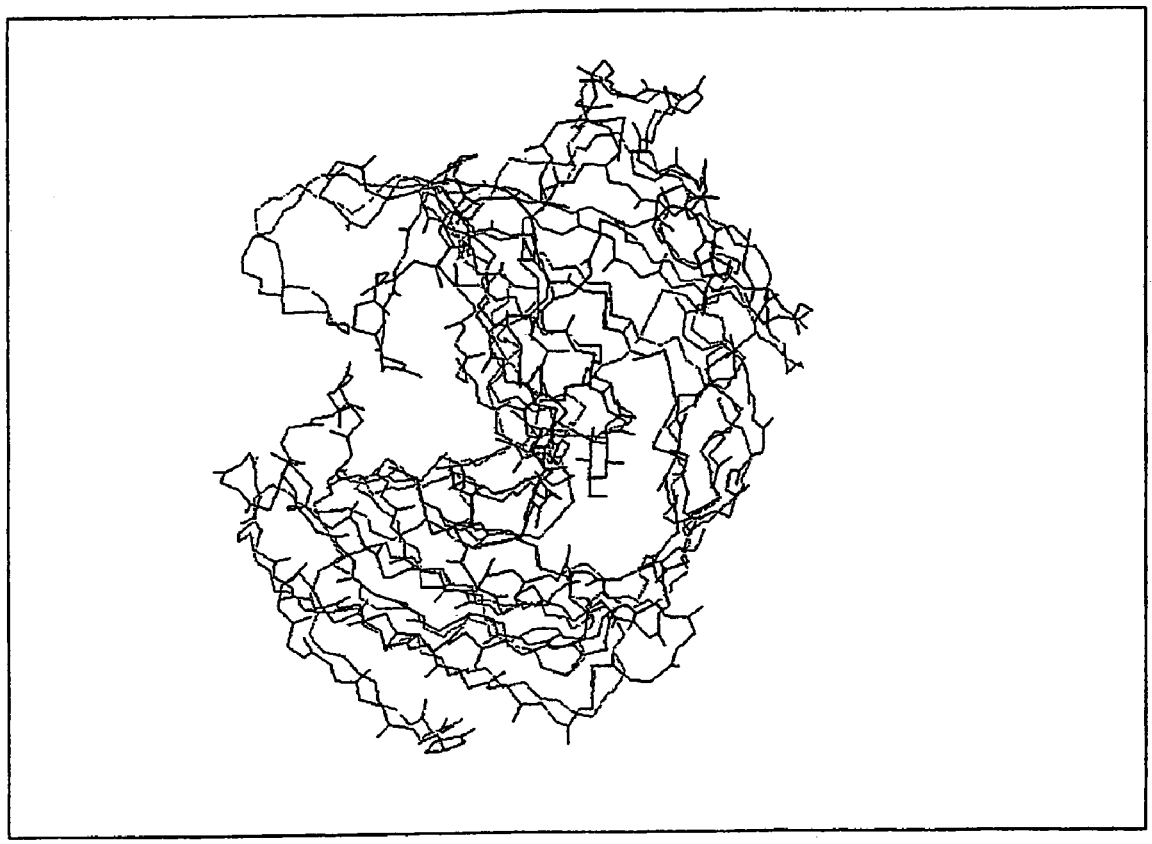

FIG. 17 shows a structural alignment of *Trichoderma reesei* xylanaseII (XynII, PDB 1 ENX, in blue;) and *Trichoderma reesei* endoglucanaseIII (Cal12A, PDB 1H8V, in red).

FIG. 18 sets forth the nucleotide amino acid of sequence of XynII.

FIG. 19 sets forth the nucleotide amino acid of sequence of EGIII.

FIG. 20 sets forth the nucleotide amino acid of sequence of Xyn1I.

DETAILED DESCRIPTION OF THE PREFERRED EMBODIMENTS

The invention will now be described in detail by way of reference only using the following definitions and examples. Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, N.Y. (1991) provide one of skill with a general dictionary of many of the terms used in this invention. Although any methods and materials similar or equivalent to those described herein can be used in the practice or testing of the present invention, the preferred methods and materials are described. Numeric ranges are inclusive of the numbers defining the range. Unless otherwise indicated, nucleic acids are written left to right in 5' to 3' orientation; amino acid sequences are written left to right in amino to carboxy orientation, respectively. Practitioners are particularly directed to Sambrook et al., 1989, and Ausubel F M et al., 1993, for definitions and terms of the art. It is to be understood that this invention is not limited to the particular methodology, protocols, and reagents described, as these may vary.

The headings provided herein are not limitations of the various aspects or embodiments of the invention which can be had by reference to the specification as a whole. Accordingly, the terms defined immediately below are more fully defined by reference to the specification as a whole.

All publications cited herein are expressly incorporated herein by reference for the purpose of describing and disclosing compositions and methodologies which might be used in connection with the invention.

As used herein, the term "polypeptide" refers to a compound made up of a single chain of amino acid residues linked by peptide bonds. The term "protein" herein may be synonymous with the term "polypeptide" or may refer, in addition, to a complex of two or more polypeptides.

As used herein, the term "expression" refers to the process by which a polypeptide is produced based on the nucleic acid sequence of the gene. The process includes both transcription and translation.

As used herein, the term "gene" means the segment of DNA involved in producing a polypeptide chain, that may or may not include regions preceding or following the coding region.

As used herein, when referring to position numbering, the term "equivalent" refers to positions as determined by sequence and structural alignments with *Trichoderma reesei* xylanase II (xynII) as a reference sequence or reference structure, as provided herein (see, for example, FIG. 2 for a multiple sequence alignment and *Trichoderma reesei* xylanaseII with other sequences, and FIG. 17 for a structural alignment of *Trichoderma reesei* Xyn II with *Trichoderma reesei* endoglucanaseIII). Position numbering shall be with respect to *Trichoderma reesei* xynII, as set forth in SEQ ID NO:1. The numbering system, even though it may use a specific sequence as a base reference point, is also applicable to all relevant homologous sequences. Sequence homology between proteins may be ascertained using well-known alignment programs and as described herein and by using hybridisation techniques described herein.

As used herein, the term "adjacent" refers to close linear and/or close spatial proximity between amino acid residues or regions or areas of a protein. For example, a first residue or first region or first area which is adjacent to a second residue or second region or second area (in a linear sense), respectively, shall have preferably about 7, preferably about 5, preferably about 2 intervening amino acid residues between them. Alternatively, for example, when a first set of residues or a first region or first area is adjacent to a second set of residues or a second region or second area, then the first set of residues or first region or first area shall be proximal (in space, as shown, for example, by the tertiary structure of a protein) to the second set of residues or second region or second area. One skilled in the art, when possible, would know how to solve the tertiary structure of a protein.

As used herein, when referring to sequence positions, the designation "+" followed by an integer shall mean that a polypeptide has been modified to include additional amino acid(s) at the putative position, as specified by the integer. For example, the designation +191 shall mean that a polypeptide which normally has 190 amino acids in the amino acid sequence has an added amino acid.

As used herein, the term "nucleic acid molecule" includes RNA, DNA and cDNA molecules. It will be understood that as a result of the degeneracy of the genetic code, a multitude of nucleotide sequences encoding a given protein, such as the mutant proteins of the invention, may be produced.

As used herein, the term "disulphide bridge" or "disulphide bond" refers to the bond formed between the sulphur atoms of cysteine residues in a polypeptide or a protein. In this invention, a disulphide bridge or disulphide bond may be non-naturally occurring and introduced by way of point mutation.

As used herein, the term "salt bridge" refers to the bond formed between oppositely charged residues, amino acids in a polypeptide or protein. In this invention, a salt bridge may be non-naturally occurring and introduced by way of point mutation.

As used herein, an "enzyme" refers to a protein or polypeptide that catalyzes a chemical reaction.

As used herein, the term "activity" refers to a biological activity associated with a particular protein, such as enzymatic activity associated with a protease. Biological activity refers to any activity that would normally be attributed to that protein by one skilled in the art.

As used herein, the term "xylanase" refers to glycosyl hydrolases that hydrolyse β-1,4-linked xylopyranoside chains.

As used herein, "XynI" refers to the *Trichoderma reesei* xylanase, xylanase I. XynI has a size of 19 kDa, a pI of 5.5 and a pH optimum of between 3 and 4.

As used herein, "XynII" refers to the *Trichoderma reesei* xylanase, xylanase II. XynII has a size of 20 kDa, a pI of 9.0 and a pH optimum of between 5 and 5.5.

As used herein, "xylopyranoside" refers to a β-1,4-linked polymer of xylose, including substituted polymers of xylose, i.e. branched β-D-1,4-linked xylophyranose polymers, highly substituted with acetyl, arabinosyl and uronyl groups (see, for example, Biely, P. (1985) Microbial Xylanolytic Systems. Trends Biotechnol., 3, 286-290.).

As used herein, the term "glycosyl hydrolase" refers to an enzyme which hydrolizes the glycosidic bond between two or more carbohydrates or between a carbohydrate and a non-carbohydrate moiety. Enzymatic hydrolysis of the glycosidic bond takes place via general acid catalysis and requires two critical residues: a proton donor and a nucleophile/base. The IUB-MB Enzyme nomenclature of glycosyl hydrolases is based on substrate specificity and occasionally on molecular mechanism.

As used herein, the term "hydrolase" refers to an enzyme that catalyzes a reaction whereby a chemical bond is enzymatically cleaved with the addition of a water molecule.

As used herein, "hydrolysis" refers to the process of the reaction whereby a chemical bond is cleaved with the addition of a water molecule.

As used herein, "Clan C" refers to groupings of families which share a common three-dimensional fold and identical catalytic machinery (see, for example, Henrissat, B. and Bairoch, A., (1996) Biochem. J., 316, 695-696).

As used herein, "family 11" refers to a family of enzymes as established by Henrissat and Bairoch (1993) Biochem J., 293, 781-788 (see, also, Henrissat and Davies (1997) Current Opinion in Structural Biol. 1997, &:637-644). Common features for family 11 members include high genetic homology, a size of about 20 kDa and a double displacement catalytic mechanism (see Tenkanen et al., 1992; Wakarchuk et al., 1994). The structure of the family 11 xylanases includes two large β-sheets made of β-strands and α-helices. Family 11 xylanases include the following: *Aspergillus niger* XynA, *Aspergillus kawachii* XynC, *Aspergillus tubigensis* XynA, *Bacillus circulans* XynA, *Bacillus pumilus* XynA, *Bacillus subtilis* XynA, *Neocallimastix patriciarum*

XynA, *Streptomyces lividans* XynB, *Streptomyces lividans* XynC, *Streptomyces thermoviolaceus* XynII, *Thermomonospora fusca* XynA, *Trichoderma harzianum* Xyn, *Trichoderma reesei* XynI, *Trichoderma reesei* XynII, *Trichoderma viride* Xyn.

As used herein, "family 12" refers to a family of enzymes established by Henrissat and Bairoch (1993) in which known glycosyl hydrolases were classified into families based on amino acid sequence similarities. To date all family 12 enzymes are cellulases. Family 12 enzymes hydrolyze the β-1,4-glycosidic bond in cellulose via a double displacement reaction and a glucosyl-enyzme intermediate that results in retention of the anomeric configuration of the product. Structural studies of family 12 members reveal a compact β-sandwich structure that is curved to create an extensive substrate binding site on the concave face of the β-sheet.

As used herein, the term "protease" refers to an enzyme that degrades by hydrolyzing at least some of their peptide bonds.

As used herein, "peptide bond" refers to the chemical bond between the carbonyl group of one amino acid and the amino group of another amino acid.

As used herein, "wild-type" refers to a sequence or a protein that is native or naturally occurring.

As used herein, "point mutations" refers to a change in a single nucleotide of DNA, especially where that change shall result in a change in a protein.

As used herein, "mutant" refers to a version of an organsim or protein where the version is other than wild-type. The change may be affected by methods well known to one skilled in the art, for example, by point mutation in which the resulting protein may be referred to as a mutant.

As used herein, "mutagenesis" refers to the process of affecting a change from a wild-type into a mutant.

As used herein, "substituted" and "modified" are used interchangeably and refer to a sequence, such as an amino acid sequence comprising a polypeptide, that includes a deletion, insertion, replacement or interruption of a naturally occurring sequence. Often in the context of the invention, a substituted sequence shall refer, for example, to the replacement of a naturally occurring residue.

As used herein, "modified enzyme" refers to an enzyme that includes a deletion, insertion, replacement or interruption of a naturally occurring sequence.

As used herein, "β-strands" refers to that portion of an amino acid sequence that forms a linear sequence that occurs in a β-sheets.

As used herein, "β-sheets" refers to the sheet-type structure that results when amino acids hydrogen-bond to each other to form a sheet like structure.

As used herein, "α-helix" refers to the structure that results when a single polypeptide chain turns regularly about itself to make a rigid cylinder in which each peptide bond is regular hydrogen-bonded to other peptide bonds in the nearby chain.

As used herein, "thumb" refers to a loop between β-strands B7 and B8 in XynI and in XynII (see, for example, in Torronen, A. and Rouvinen, J.; Biochemistry 1995, 34, 847-856).

As used herein, "cord" refers to a loop between β-strands B7 and B8 which make a thumb and a part of the loop between β-strands B6a and B9 which crosses the cleft on one side (see, for example, Torronen, A. and Rouvinen, J.; Biochemistry 1995, 34, 847-856).

As used herein, "alkaline" refers to the state or quality of being basic.

As used herein, "alkalophilic" refers to the quality of being more robust in an alkaline atmosphere than a non-alkalophilic member. For example, an alkalophilic organism refers to an organism that survives or thrives under alkaline conditions where a normal organism may not, and an alkalophilic protein is one whose activity is active or more robust under alkaline conditions where a normal protein would be less active.

As used herein, "acidic" refers to the state or quality of being acidic.

As used herein, "acidophilic" refers to the quality of being more robust in an acidic atmosphere than a non-acidophilic member. For example, an acidophilic organism refers to an organism that survives or thrives under acidic conditions where a normal organism may not, and an acidophilic protein is one whose activity is active or more robust under acidic conditions where a normal protein would be less active.

As used herein, "thermostable" refers to the quality of being stable in an atmosphere involving temperature. For example, a thermostable organism is one that is more stable under specified temperature conditions than a non-thermostable organism.

As used herein, "thermostability," refers to the quality of being thermostable.

As used herein, "thermophilic" refers to the quality of being more robust in an hot atmosphere than a non-thermophilic member. For example, a thermophilic organism refers is to an organism that survives or thrives under hot conditions where a normal organism may not, and a thermophilic protein is one whose activity is active or more robust under hot conditions where a normal protein would be less active.

As used herein, "mesophilic" refers to the quality of being more robust in an normal atmosphere than a non-mesophilic member. For example, a mesophilic organism refers to an organism that survives or thrives under normal conditions where another organism may not, and a mesophilic protein is one whose activity is active or more robust under normal conditions where another protein would be less active.

As used herein, "oligonucleotides" refers to a short nucleotide sequence which may be used, for example, as a primer in a reaction used to create mutant proteins. As used herein, "codon" refers to a sequence of three nucleotides in a DNA or mRNA molecule that represents the instruction for incorporation of a specific amino acid into a polypeptide chain.

As used herein, "Y5" refers to a mutant xylanase as disclosed, for example, in publication number WO 01/27252.

As used herein, the following designations shall refer to the following mutants:

"P2"=N97R+H144K/Y5
"P3"=F93W+H144K in Y5
"P8"=F180Q in Y5
"P9"=N97R in F93W+H144K in Y5
"P12"=H144C+N92C in Y5
"P15"=F180Q in H144C+N92C in Y5
"P16"=N97R in H144C+N92C in Y5
"P18"=H22K in Y5
"P20"=H22K+F180Q in Y5
"P21"=H22K+F180Q+H144C+N92C in Y5
"J17"=V108H in Y5
"J21"=S65C+S186C in Y5 wherein position numbering shall be with respect to XynII, wherein the position of the substituted amino acid is numbered from the amino acid after the signal and pro sequence of SEQ ID NO:1.

The present invention relates to modified enzymes with improved performance in extreme conditions, such as temperature and pH.

In a first aspect, the invention is drawn to a modified xylanase comprising a polypeptide having an amino acid sequence as set forth in SEQ ID NO:1, wherein the sequence has at least one substituted amino acid residue at a position selected from the group consisting of: 2, 5, 10, 11, 16, 19, 22, 26, 28, 29, 30, 34, 36, 38, 57, 58, 61, 63, 65, 67 92, 93, 97, 105, 108, 110, 111, 113, 132, 143, 144, 147, 149, 151, 153, 157, 160, 162, 165, 169, 180, 184, 186, 188, 190 and +191, where position numbering is with respect to SEQ ID NO:1. Preferably, the substitution is selected from the group consisting of: 2, 22, 28, 58, 65, 92, 93, 97, 105, 108, 144, 162, 180, 186 and +191. Preferably, the modified xylanase has at least one substitution selected from the group consisting of H22K, S65C, N92C, F93W, N97R, V180H, H144C, H144K, F180Q and S186C. Also, preferably, the modified xylanase exhibits improved thermophilicity, alkalophilicity or a combination thereof, in comparison to a wild-type xylanase, wherein the position of the substituted amino acid is numbered from the amino acid after the signal and pro sequence.

In a second aspect, the invention is drawn to a modified enzyme, the modified enzyme comprising an amino acid sequence, the amino acid sequence being homologous to the sequence set forth in SEQ ID NO:1, the amino acid sequence having at least one substituted amino acid residue at a position equivalent to a position selected from the group consisting of: 2, 5, 7, 10, 11, 16, 19, 22, 26, 28, 29, 30, 34, 36, 38, 44, 57, 58, 61, 63, 65, 67, 92, 93, 97, 105, 108, 110, 111, 113, 132, 143, 144, 147, 149, 151, 153, 157, 160, 162, 165, 169, 180, 184, 186, 188, 190 and +191, wherein position numbering is with respect to SEQ ID NO:1. In a preferred embodiment, the amino acid sequence has at least one substituted amino acid residue at a position equivalent to a position selected from the group consisting of: 2, 22, 28, 58, 65, 92, 93, 97, 105, 108, 144, 162, 180, 186 and +191. In a preferred embodiment, the amino acid sequence has at least one substituted amino acid residue selected from the group consisting of: H22K, S65C, N92C, F93W, N97R, V108H, H144C, H144K, F180Q and S186C.

In a preferred embodiment of the invention, the modified enzyme is a glycosyl hydrolase of Clan C comprising an amino acid sequence, the amino acid sequence being homologous to the sequence set forth in SEQ ID NO:1, the amino acid sequence having at least one substituted amino acid residue at a position equivalent to a position selected from the group consisting of: 2, 5, 7, 10, 11, 16, 19, 22, 26, 28, 29, 30, 34, 36, 38, 57, 58, 61, 63, 65, 67, 92, 93, 97, 105, 110, 108, 110, 111, 113, 132, 143, 144, 147, 149, 151, 153, 157, 160, 162, 165, 169, 180, 184, 186, 188, 190 and +191. In a preferred embodiment, the amino acid sequence has at least one substituted amino acid residue at a position equivalent to a position selected from the group consisting of: 2, 22, 28, 58, 65, 92, 93, 97, 105, 108, 144, 162, 180, 186 and +191. In a preferred embodiment, the amino acid sequence has at least one substituted amino acid residue selected from the group consisting of: H22K, S65C, N92C, F93W, N97R, V108H, H144C, H144K, F180Q and S186C. Preferred modified enzymes are as disclosed herein.

In a preferred embodiment, the modified enzyme is a family 11 xylanase comprising an amino acid sequence, the amino acid sequence being homologous to the sequence set forth in SEQ ID NO:1, the amino acid sequence having at least one substituted amino acid residue at a position equivalent to a position selected from the group consisting of: 2, 5, 7, 10, 11, 16, 19, 22, 26, 28, 29, 30, 34, 36, 38, 57, 58, 61, 63, 65, 67, 92, 93, 97, 105, 108, 110, 111, 113, 132, 143, 144, 147, 149, 151, 153, 157, 160, 162, 165, 169, 180, 184, 186, 188, 190 and +191. In a preferred embodiment, the amino acid sequence has at least one substituted amino acid residue at a position equivalent to a position selected from the group consisting of: 2, 22, 28, 58, 65, 92, 93, 97, 105, 108, 144, 162, 180, 186 and +191. In a preferred embodiment, the amino acid sequence has at least one substituted amino acid residue selected from the group consisting of: H22K, S65C, N92C, F93W, N97R, V108H, H144C, H144K, F180Q and S186C. Preferred modified family 11 enzymes are as disclosed herein.

In another preferred embodiment, the modified enzyme is a family 12 cellulase comprising an amino acid sequence, the amino acid sequence being homologous to the sequence set forth in SEQ ID NO:1, the amino acid sequence having at least one substituted amino acid residue at a position equivalent to a position selected from the group consisting of: 2, 5, 7, 10, 11, 16, 19, 22, 26, 28, 29, 30, 34, 36, 38, 57, 58, 61, 63, 65, 67, 92, 93, 97, 105, 108, 110, 111, 113, 132, 143, 144, 147, 149, 151, 153, 157, 160, 162, 165, 169, 180, 184, 186, 188, 190 and +191. In a preferred embodiment, the amino acid sequence has at least one substituted amino acid residue at a position equivalent to a position selected from the group consisting of: 2, 22, 28, 58, 65, 92, 93, 97, 105, 108, 144, 162, 180, 186 and +191. In a preferred embodiment, the amino acid sequence has at least one substituted amino acid residue selected from the group consisting of: H22K, S65C, N92C, F93W, N97R, V108H, H144C, H144K, F180Q and S186C. Preferred family 12 modified enzymes are as disclosed herein.

In a preferred embodiment, the family 12 cellulase is *Trichoderma* EGIII cellulase as set forth in SEQ ID NO:3, the modification comprises at least one amino acid selected from the group consisting of: 2, 13, 28, 34, 77, 80, 86, 122, 123, 134, 137, 140, 164, 174, 183, 209, 215 and 218, position numbering being with respect to SEQ ID NO:3. In a preferred embodiment, the substitution is at least one mutation selected from the group consisting of T2C, N13H, S28K, T34C, S77C, P80R, S86C, G122C, K123W, Q134H, Q134K, Q134R, V137H, G140C, N164C, N164K, N174C, K183H, N209C, A215D and N218C, position numbering being with respect to SEQ ID NO:3.

XynII exhibits a significant amino acid homology with other members of family 11, approximately 20-90%, as well as overall structural similarity. Homology, as used herein, may be determined by one skilled in the art; specifically, homologies of at least 20%, preferably 30% or more, preferably 40% or more, preferably 50% or more, preferably 60% or more, preferably 70% or more, preferably 80% or more, preferably 90% or more, preferably 95% or more and preferably 97% or more are contemplated (as calculated at the amino acid level and the nucleotide level and as used herein). There are structural similarities between family 11 and family 12 enzymes. Beta proteins have two stacked beta sheets, and one alpha helix packed against one of the beta sheets forming a so-called beta-jelly roll structure. (see Stirk, H. J., Woolfson, D. N., Hutchison, E. G. and Thornton, J. M. (1992) Depicting topology and handedness in jellyroll structures. *FEBS Letters* 308 p 1-3).

Based on this structural similarity, both enzyme families have been assigned to a "super family" referred to as Clan C (see Sandgren, M. et. al., J. Mol. Bio. (2001) 308, 295-310.)).

Although the sequence homology between families 11 and 12 is low, the overall structural similarity of the two families is remarkable as seen by comparing FIGS. 2 and 16. The length of the loops connecting the two beta-sheets comprises the major structural differences between the families (Sandgren et. al., J. Mol., Biol., 2001). Presently, no family 11 enzymes are known to contain N terminal disulphide bridges while many family 12 cellulases, in general appear to contain a disulphide bridge near the N-terminus (e.g, between residues 4 and 32 in *T. reesei* Cel 12A). That disulphide bridge in family 12 enzymes is located near the position where a disulphide was introduced into the *Trichoderma* (Y5) variant, although further away from the N-terminus (see, for example, publication WO 01/27252). The importance of a restriction stabilizing the N-terminal region of family 11 enzymes was examined in *Trichoderma reesei* xylanase II (XynII). By inserting a non-natural disulphide bridge between residues (T2C and T28C), an increase in $T_m$ of 11° C. was achieved. In these two structurally similar families, family 11 and family 12, the N-terminal disulphide bridges play a similar roles regarding stability. This has is been demonstrated by replacing the cysteine at position 32 with an alanine in Cel12A resulting in a significant decrease in $T_m$ of 18.5° C. Interestingly, the magnitude of the change in stability for adding a non-natural N-terminal disulphide into XynII is comparable to that of removing a natural one from Cel 12A (see table A).

TABLE A

| Enzyme | Delta Tm | Tm (degrees C.) |
|---|---|---|
| WT Cel12A | | 54.4 |
| C32A | −18.5 | 35.9 |
| WT xynII | | 58.6 |
| Y5 | +10.7 | 69.3 |

Table A shows the melting temperatures, $T_m$ of the wild type Cel12A compared to the variant with the substitution at position 32, and the wild type XynII compared to the Y5 variant of this enzyme.

The three dimensional structures of the N-terminal disulphide bridges of the three publicly known structures for family 12 glycosyl hydrolases (*Trichoderma reesei*—PDB 1H8V, *Aspergillus niger*—PDB 1KS5, *Streptomyces lividans*—PDB 2NLR), show a shift in the position of the disulphide bridge as compared to the non-natural disulphide bridge at sites 2 and 28 in Y5 xylanase. Table B shows the position of the disulphide bridge in a Y5 xylanase ("PDB 1ENX" being wild type XynII xylanase) and in the three known family 12 structures. The structural positions of the mutations at 2 and 28 of Y5 xylanase can be translated to the corresponding residues in the Cel 12 structures. In each case, the non-native disulphide from Y5 is closer to the N-terminus; and for the *A. niger* structure (PDB 1KS5) a disulphide could be designed that would utilize the N-terminal residue itself (at residues Q1C, V35C, according to *A. niger* numbering). Instead of being limited by the natural sequence, X-ray data could be used to design extensions and truncations of the N-terminus to facilitate non-native disulphides that specifically attach to the new N-terminal residues.

TABLE B

| Code | WT N-terminal S—S position | Corresponding site to 2-28 of xynII | Where (according to structure) could a S—S be inserted at the N-terminal |
|---|---|---|---|
| PDB 1ENX | No | — | |
| Y5 | C2-C28 | T2-T28 | T2C-T28C |
| PDB 1H8V | C4-C32 | T2-T34 | T2C-T34C |
| PDB 1KS5 | C4-C32 | T2-Y34 | Q1C-V35C |
| PDB 2NLR | C5-C31 | T3-T33 | T3C-T33C |

A large number of family 12 sequences (Table C) are known which could potentially be stabilized through an N-terminal disulphide bridge, particularly those molecules where a non-native disulphide bridge could be introduced or a native disulphide could be moved closer to an N-terminus. Table C lists a number of sequences where a predicted removal of the signal sequence produces mature protein sequences very similar to the ones of the known family 12 structures. Table C also lists the distance between the two N-terminal cysteines (26-28 amino acids) similar to the disulphide bond of Y5. In the cleavage site predictions, a signal sequences is theoretically removed by the means of known, acknowledged parameters (see, for example, "Identification of prokaryotic and eukaryotic signal peptides and prediction of their cleavage sites". Henrik Nielsen, Jacob Engelbrecht, Søren Brunak and Gunnar von Heijne, *Protein Engineering* 10, 1-6 (1997)).

A large group of sequences of unknown three dimensional structures in Table C fall within the structurally similar group of family 12 enzymes, which have in a similar manner a cysteine residue at the N-terminal at site 5+/−2 residues, forming a disulphide bridge with residue 32+/−7, such that the first beta strand or strands of the beta sheet can be bound to the adjacent beta sheet. All of these sequences could be treated in the manner described in the discussion around table B to improve stability.

TABLE C

| ID | Sequence | Eucaryote/ Gram−/ Gram+ | Predicted cleavage site | Number of adequate cysteine ($1^{st}$ in ss bond) | aa's to $2^{nd}$ cysteine in ss bond |
|---|---|---|---|---|---|
| Q8NJY2 | Endoglucanase {GENE: CEL12B} *Aspergillus awamori* (var. *kawachi*) | Eu | 16-17 | 6 | 28 |
| Q8NJY4 | Endoglucanase {GENE: CEL12A} - *Trichoderma viride* | Eu | 16-17 | 4 | 28 |
| Q8NJY5 | Endoglucanase {GENE: CEL12A} - *Hypocrea koningii* | Eu | 16-17 | 4 | 28 |
| Q8NJY6 | Endoglucanase {GENE: CEL12A} - *Hypocrea schweinitzii* | Eu | 16-17 | 4 | 28 |

TABLE C-continued

| ID | Sequence | Eucaryote/Gram-/Gram+ | Predicted cleavage site | Number of adequate cysteine (1$^{st}$ in ss bond) | aa's to 2$^{nd}$ cysteine in ss bond |
|---|---|---|---|---|---|
| Q8NJY7 | Endoglucanase {GENE: CEL12A} - Stachybotrys echinata | Eu | 16-17 | 4 | 28 |
| Q8NJY8 | Endoglucanase {GENE: CEL12D} - Bionectria ochroleuca | Eu | 17-18 | 4 | 28 |
| Q8NJY9 | Endoglucanase {GENE: CEL12C} - Bionectria ochroleuca | Eu | 17-18 | 3 | 28 |
| Q8NJZ1 | Endoglucanase {GENE: CEL12A} - Bionectria ochroleuca | Eu | 18-19 | 4 | 28 |
| Q8NJZ4 | Endoglucanase {GENE: CEL12A} - Fusarium equiseti (Fusarium scirpi) | Eu | 17-18 | 4 | 28 |
| Q9KIH1 | Cellulase 12A {GENE: CEL12A} - Streptomyces sp. 11AG8 | Gram+ | 31-32 | 5 | 26 |

Table D lists further a number of sequences of family 12 enzymes with uncleaved signal sequence. They all have cysteines 30-39 amino acids apart, and after a removal of the signal sequence (removal can be performed as in table C) are structurally capable of forming a disulphide bridge at the N-terminal (as seen in the publicly known structures, see table B). The proposed mutation site correlates to the corresponding site of the disulphide bridge between sites 2-28 of the Y5 mutant. The glycosyl hydrolase sequences were aligned using the program MOE (Chemical Computing Corp) using standard sequence matching methods.

TABLE D

| Sequence code | enzyme | Species | Mutations |
|---|---|---|---|
| Tr O94218 | Cel12 | Aspergillus aculeatus | D22C/G52C |
| Sp P22669 | Cel12 | Aspergillus aculeatus | Q20C/T52C |
| Sp Q12679 | Cel12 | Aspergillus awamori | T18C/Y50C |
| Tr O13454 | Cel12 | Aspergillus oryzae | E18C/Y50C |
| Sp P16630 | Cel12 | Erwina carotovora | A32C/I68C |
| Tr O31030 | Cel12 | Pectobacterium carotovora | A32C/V68C |
| Tr Q9V2TO | Cel12 | Pyrococcus furiosus | P57C/T96C |
| Tr O33897 | Cel12 | Rhodothermus marinus | E40C/E70C |
| Tr Q9RJY3 | Cel12 | Streptomyces coelicolor | T43C/T73C |
| Tr O08468 | Cel12 | Streptomyces halstedii | L40C/T70C |
| Tr Q59963 | Cel12 | Streptomyces rochei | T40C/T70C |
| Tr Q9KIH1 | Cel12 | Streptomyces sp. 11AG8 | Q34C/N64C |
| Tr Q60032 | Cel12 | Thermotoga maritima | V2C/K38C |
| Tr Q60033 | Cel12 | Thermotoga maritime | V20C/K56C |
| Tr O08428 | Cel12 | Thermotoga neopolitana | V2C/R38C |
| Tr P96492 | Cel12 | Thermotoga neopolitana | V20C/K56C |
| AF435072 | Cel12A | Aspergillus Kawachi | Q20C/T52C |
| AF434180 | Cel12A | Chaetium brasilience | S28C/Y61C |
| AF434181 | Cel12A | Emericella desertorum | D30C/G63C |
| AF434182 | Cel12A | Fusarium equiseti | D19C/H51C |
| AF434183 | Cel12A | Nectria ipomoeae | Q25C/T58C |
| AF434184 | Cel12B | Nectria ipomoeae | T32C/T65C |
| AF435063 | Cel12A | Bionectria ochroleuca | T20C/Y52C |
| AF435064 | Cel12B | Bionectria ochroleuca | T34C/T66C |
| AF435065 | Cel12C | Bionectria ochroleuca | A18C/T50C |
| AF435066 | Cel12D | Bionectria ochroleuca | S19C/Y51C |
| AF435071 | Cel12A | Humicola grisea | S34C/Y67C |
| AF435068 | Cel12A | Hypochrea schweinitzii | T18C/T50C |
| AF435067 | Cel12A | Stachybotrys echinata | S18C/Y50C |

Not only does the N-terminal region show high structural similarity between families 11 and 12; both families show a hand like structure, the one of a "partly closed right hand" as described in Torronen et al. 1997. The two β-sheets form "fingers", and a twisted pair from one β-sheet and the a-helix forms a "palm". The long loop between β-strands B7 and B8 makes the "thumb" and a part of the loop between β-strands B6b (residues 95-102 in xynII and 125-131 in Cel12A) and B9 forms a "cord", which crosses the cleft on one side (Torronen A. and Rouvinen, J. Biochem. 1995, 34, 847-0856). The stabilizing effect of inserting rigidifying substitutions between beta strand B6b and the adjacent loop and/or the "cord" is seen in the mutation at sites 92, 93, 144 (N92C—H144C, at least one of the following mutations N97R, F93W+H144K (XynI), and can in a similar way be introduced into corresponding sites in family 12.

Table E shows the numbering of a selection of structurally equivalent sites between xynII and Cel 12A. The high structural similarity between the two families enables a large number of similar substitutions (see Sandgren et. al., J. Mol., Biol., 2001 for structural comparison).

TABLE E

| Examples of equivalent sites | |
|---|---|
| XynII | Cell2A |
| T2C | T2C |
| T28C | T34C |
| N92C | G122C |
| H144C, K | N164C, K |
| F93W | K123W |
| Q162H | K183H |

The modified enzymes of the invention may comprise one or more mutations in is addition to those set out above. Other mutations, such as deletions, insertions, substitutions, transversions, transitions and inversions, at one or more other locations, may also be included. Likewise, the modified enzyme may be missing at least one of the substitutions set forth above.

The modified enzyme may also comprise a conservative substitution that may occur as a like-for-like substitution (e.g., basic for basic, acidic for acidic, polar for polar etc.) Non-conservative substitutions may also occur, i.e. from one class of residue to another or alternatively involving the inclusion of unnatural amino acids such as ornithine, diaminobutyric acid ornithine, norleucine ornithine, pyriylalanine, thienylalanine, naphthylalanine and phenylglycine.

The sequences may also have deletions, insertions or substitutions of amino acid residues that produce a silent change and result in a functionally equivalent substance. Deliberate amino acid substitutions may be made on the basis of similarity in amino acid properties (such as polarity, charge, solubility, hydrophobicity, hydrophilicity, and/or the amphipathic nature of the residues) and it is therefore useful to group amino acids together in functional groups. Amino acids can be grouped together based on the properties of their side chain alone. However it is more useful to include mutation data as well. The sets of amino acids thus derived are likely to be conserved for structural reasons. These sets can be described in the form of a Venn diagram (Livingstone C. D. and Barton G. J. (1993) "Protein sequence alignments: a strategy for the hierarchical analysis of residue conservation" Comput. Appl Biosci. 9: 745-756)(Taylor W. R. (1986) "The classification of amino acid conservation" J. Theor. Biol. 119; 205-218). Conservative substitutions may be made, for example according to the table below which describes a generally accepted Venn diagram grouping of amino acids.

Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package the default gap penalty for amino acid sequences is −12 for a gap and −4 for each extension.

Calculation of maximum % homology therefore firstly requires the production of an optimal alignment, taking into

| Set | | Sub-set | |
|---|---|---|---|
| Hydrophobic | F W Y H K M I L V A G C | Aromatic | F W Y H |
| | | Aliphatic | I L V |
| Polar | W Y H K R E D C S T N Q | Charged | H K R E D |
| | | Positively charged | H K R |
| | | Negatively charged | E D |
| Small | V C A G S P T N D | Tiny | A G S |

Variant amino acid sequences may also include suitable spacer groups inserted between any two amino acid residues of the sequence including alkyl groups such as methyl, ethyl or propyl groups in addition to amino acid spacers such as glycine or β-alanine residues. A further form of variation involves the presence of one or more amino acid residues in peptoid form.

Homology comparisons can be conducted by eye, or more usually, with the aid of readily available sequence comparison programs. These commercially available computer programs can calculate % homology between two or more sequences. % homology may be calculated over contiguous sequences, i.e. one sequence is aligned with the other sequence and each amino acid in one sequence is directly compared with the corresponding amino acid in the other sequence one residue at a time. This is called an "ungapped" alignment. Typically, such ungapped alignments are performed over a relatively short number of residues.

Although this is a very simple and consistent method, it fails to take into consideration that, for example, in an otherwise identical pair of sequences, one insertion or deletion will cause following amino acid residues to be put out of alignment, thus potentially resulting in a large reduction in % homology when a global alignment is is performed.

consideration gap penalties. A suitable computer program for carrying out such an alignment is the GCG Wisconsin Bestfit package (Devereux et al 1984 Nuc. Acids Research 12 p 387). Examples of other software than can perform sequence comparisons include, but are not limited to, the BLAST package (see Ausubel et al., 1999 Short Protocols in Molecular Biology, 4$^{th}$ Ed—Chapter 18), FASTA (Altschul et al., 1990 J. Mol. Biol. 403-410) and the GENEWORKS suite of comparison tools. Both BLAST and FASTA are available for offline and online searching (see Ausubel et al., 1999, Short Protocols in Molecular Biology, pages 7-58 to 7-60). However, for some applications, it is preferred to use the GCG Bestfit program. BLAST 2 Sequences is also available for comparing protein and nucleotide sequence (see FEMS Microbiol Lett 1999 174(2): 247-50; FEMS Microbiol Lett 1999 177(1): 187-8 and tatiana@ncbi.nlm.nih.gov).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). For some applications, it is preferred to use the public default values for the GCG package, or in the case of other software, the default matrix, such as BLOSUM62.

Alternatively, percentage homologies may be calculated using the multiple alignment feature in DNASIS™ (Hitachi Software), based on an algorithm, analogous to CLUSTAL (Higgins D G & Sharp P M (1988), Gene 73(1), 237-244).

Once the software has produced an optimal alignment, it is possible to calculate % homology, preferably % sequence identity. The software typically does this as part of the sequence comparison and generates a numerical result.

Embodiments of the first and second aspects of the invention, as disclosed above, provide a nucleic acid encoding any of the modified enzymes, as set forth above, as well as complements thereof. In another preferred embodiment, the invention provides for compositions comprising at least one modified enzyme, as disclosed herein, and another ingredient. In another preferred embodiment, the invention provides vectors comprising a modified enzyme, as disclosed herein, cells comprising the modified enzyme and methods of expressing the modified enzyme.

One skilled in the art will be aware of the relationship between nucleic acid sequence and polypeptide sequence, in particular, the genetic code and the degeneracy of this code, and will be able to construct such modified enzymes without difficulty. For example, one skilled in the art will be aware that for each amino acid substitution in the modified enzyme sequence there may be one or more codons which encode the substitute amino acid. Accordingly, it will be evident that, depending on the degeneracy of the genetic code with respect to that particular amino acid residue, one or more modified enzyme nucleic acid sequences may be generated corresponding to that modified enzyme polypeptide sequence.

Mutations in amino acid sequence and nucleic acid sequence may be made by any of a number of techniques, as known in the art. In particularly preferred embodiments, the mutations are introduced into parent sequences by means of PCR (polymerase chain reaction) using appropriate primers, as illustrated in the Examples. The parent enzymes may be modified at the amino acid level or the nucleic acid level to generate the modified is enzyme sequences described herein. Therefore, a preferred embodiment provides for the generation of modified enzymes by introducing one or more corresponding codon changes in the nucleotide sequence encoding a modified enzyme.

It will be appreciated that the above codon changes can be made in any modified enzyme nucleic acid sequence. For example, sequence changes can be made to any of the homologous sequences described herein.

The modified enzyme may comprise the "complete" enzyme, i.e., in its entire length as it occurs in nature (or as mutated), or it may comprise a truncated form thereof. The modified enzyme derived from such may accordingly be so truncated, or be "full-length". The truncation may be at the N-terminal end or the C-terminal end. The modified enzyme may lack one or more portions, such as sub-sequences, signal sequences, domains or moieties, whether active or not.

A nucleotide sequence encoding either an enzyme which has the specific properties as defined herein or an enzyme which is suitable for modification, such as a modified enzyme, may be identified and/or isolated and/or purified from any cell or organism producing said enzyme. Various methods are well known within the art for the identification and/or isolation and/or purification of nucleotide sequences. By way of example, PCR amplification techniques to prepare more of a sequence may be used once a suitable sequence has been identified and/or isolated and/or purified.

By way of further example, a genomic DNA and/or cDNA library may be constructed using chromosomal DNA or messenger RNA from the organism producing the enzyme. If the amino acid sequence of the enzyme or a part of the amino acid sequence of the enzyme is known, labelled oligonucleotide probes may be synthesised and used to identify enzyme-encoding clones from the genomic library prepared from the organism. Alternatively, a labelled oligonucleotide probe containing sequences homologous to another known enzyme gene could be used to identify enzyme-encoding clones. In the latter case, hybridisation and washing conditions of lower stringency are used.

Alternatively, enzyme-encoding clones could be identified by inserting fragments of genomic DNA into an expression vector, such as a plasmid, transforming enzyme-negative bacteria with the resulting genomic DNA library and then plating the transformed bacteria onto agar plates containing a substrate for enzyme thereby allowing clones expressing the is enzyme to be identified.

In a yet further alternative, the nucleotide sequence encoding the modified enzyme may be prepared synthetically by established standard methods, e.g. the phosphoroamidite method described by Beucage S. L. et al., (1981) *Tetrahedron Letters* 22, p 1859-1869 or the method described by Matthes et al., (1984) *EMBO J.* 3, p 801-805. In the phosphoroamidite method, oligonucleotides are synthesised, e.g. in an automatic DNA synthesiser, purified, annealed, ligated and cloned in appropriate Vectors.

The nucleotide sequence may be of mixed genomic and synthetic origin, mixed synthetic and cDNA origin or mixed genomic and cDNA origin, prepared by ligating fragments of synthetic, genomic or cDNA origin in accordance with standard techniques. Each ligated fragment corresponds to various parts of the entire nucleotide sequence. The DNA sequence may also be prepared by polymerase chain reaction (PCR) using specific primers, for instance as described in U.S. Pat. No. 4,683,202 or in Saiki R K et al., (*Science* (1988) 239, pp 481-491).

The nucleotide sequences described here, and suitable for use in the methods and compositions described here may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule. For the purposes of this document, it is to be understood that the nucleotide sequences described herein may be modified by any method available in the art. Such modifications may be carried out in order to enhance the in vivo activity or life span of nucleotide sequences.

A preferred embodiment of the invention provides for nucleotide sequences and the use of nucleotide sequences that are complementary to the sequences presented herein, or any derivative, fragment or derivative thereof. If the sequence is complementary to a fragment thereof then that sequence can be used as a probe to identify similar coding sequences in other organisms etc.

Polynucleotides which are not 100% homologous to the modified enzyme sequences may be obtained in a number of ways. Other variants of the sequences described herein may be obtained for example by probing DNA libraries made from a range of individuals, for example individuals from different populations. In addition, other homologues may be obtained and such homologues and fragments thereof in general will be capable of selectively hybridising to the sequences shown in the sequence listing herein. Such sequences may be obtained by probing cDNA libraries made from or genomic DNA libraries from other species and probing such libraries with probes comprising all or part of any one of the sequences in the attached sequence listings under conditions of medium to high stringency. Similar considerations apply to obtaining species homologues and allelic variants of the polypeptide or nucleotide sequences described here.

Variants and strain/species homologues may also be obtained using degenerate PCR which will use primers designed to target sequences within the variants and homologues encoding conserved amino acid sequences. The primers used in degenerate PCR will contain one or more degenerate positions and will be used at stringency conditions lower than those used for cloning sequences with single sequence primers against known sequences. Conserved sequences can be predicted, for example, by aligning the amino acid sequences from several variants/homologies. Sequence alignments can be performed using computer software known in the art as described herein.

Alternatively, such polynucleotides may be obtained by site directed mutagenesis of characterised sequences, as provided herein. This may be useful where, for example, silent codon sequence changes are required to optimise codon preferences for a particular host cell in which the polynucleotide sequences are being expressed. Other sequence changes may be desired in order to introduce restriction enzyme recognition sites, or to alter the property or function of the polypeptides encoded by the polynucleotides.

The polynucleotides may be used to produce a primer, e.g. a PCR primer, a primer for an alternative amplification reaction, a probe e.g. labelled with a revealing label by conventional means using radioactive or non-radioactive labels or the polynucleotides may be cloned into vectors. Such primers, probes and other fragments will be at least 15, preferably at least 20, for example at least 25, 30 or 40 nucleotides in length, and are also encompassed by the term polynucleotides.

Polynucleotides such as DNA polynucleotides and probes may be produced recombinantly, synthetically or by any means available to those of skill in the art. They may also be cloned by standard techniques. In general, primers will be produced by synthetic means, involving a stepwise manufacture of the desired nucleic acid sequence one nucleotide at a time. Techniques for accomplishing this using automated techniques are readily available in the art.

Longer polynucleotides will generally be produced using recombinant means, for example using a PCR (polymerase chain reaction) cloning techniques. The primers may be designed to contain suitable restriction enzyme recognition sites so that the amplified DNA can be cloned into a suitable cloning vector. Preferably, the variant sequences are at least as biologically active as the sequences presented herein.

A preferred embodiment of the invention includes sequences that are complementary to the modified enzyme or sequences that are capable of hybridising either to the nucleotide sequences of the modified enzymes (including complementary sequences of those presented herein), as well as nucleotide sequences that are complementary to sequences that can hybridise to the nucleotide sequences of the modified enzymes (including complementary sequences of those presented herein). A preferred embodiment provides polynucleotide sequences that are capable of hybridising to the nucleotide sequences presented herein under conditions of intermediate to maximal stringency.

A preferred embodiment includes nucleotide sequences that can hybridise to the nucleotide sequence of the modified enzyme nucleic acid, or the complement thereof, under stringent conditions (e.g. 50° C. and 0.2×SSC). More preferably, the nucleotide sequences can hybridise to the nucleotide sequence of the modified enzyme, or the complement thereof, under high stringent conditions (e.g. 65° C. and 0.1×SSC).

It may be desirable to mutate the sequence in order to prepare a modified enzyme. Accordingly, a mutant may be prepared from the modified enzymes provided herein. Mutations may be introduced using synthetic oligonucleotides. These oligonucleotides contain nucleotide sequences flanking the desired mutation sites. A suitable method is disclosed in Morinaga et al., (*Biotechnology* (1984) 2, p 646-649). Another method of introducing mutations into enzyme-encoding nucleotide sequences is described in Nelson and Long (*Analytical Biochemistry* (1989), 180, p 147-151). A further method is described in Sarkar and Sommer (*Biotecliniques* (1990), 8, p404-407—"The megaprimer method of site directed mutagenesis"). Other methods to mutate the sequence are employed and disclosed herein.

In a preferred embodiment, the sequence for use in the methods and compositions described here is a recombinant sequence—i.e. a sequence that has been prepared using recombinant DNA techniques. Such techniques are explained, for example, in the literature, for example, J. Sambrook, E. F. Fritsch, and T. Maniatis, 1989, *Molecular Cloning: A Laboratory Manual*, Second Edition, Books 1-3, Cold Spring Harbor Laboratory Press.

Another embodiment provides for compositions and formulations comprising modified enzymes. The compositions include the modified enzyme together with another component.

Another embodiment provides vectors comprising the modified enzyme, cells comprising the modified enzyme and methods of expressing the modified enzyme. The nucleotide sequence for use in the methods and compositions described herein may be incorporated into a recombinant replicable vector. The vector may be used to replicate and express the nucleotide sequence, in enzyme form, in and/or from a compatible host cell. Expression may be controlled using control sequences, e.g., regulatory sequences. The enzyme produced by a host recombinant cell by expression of the nucleotide sequence may be secreted or may be contained intracellularly depending on the sequence and/or the vector used. The coding sequences may be designed with signal sequences which direct secretion of the substance coding sequences through a particular prokaryotic or eukaryotic cell membrane. Polynucleotides can be incorporated into a recombinant replicable vector. The vector may be used to replicate the nucleic acid in a compatible host cell. The vector comprising the polynucleotide sequence may be transformed into a suitable host cell. Suitable hosts may include bacterial, yeast, insect and fungal cells.

Modified enzymes and their polynucleotides may be expressed by introducing a polynucleotide into a replicable vector, introducing the vector into a compatible host cell and growing the host cell under conditions which bring about replication of the vector. The vector may be recovered from the host cell.

The modified enzyme nucleic acid may be operatively linked to transcriptional and translational regulatory elements active in a host cell of interest. The modified enzyme nucleic acid may also encode a fusion protein comprising signal sequences such as, for example, those derived from the glucoamylase gene from *Schwanniomyces occidentalis*, α-factor mating type gene from *Saccharomyces cerevisiae* and the TAKA-amylase from *Aspergillus oryzae*. Alternatively, the modified enzyme nucleic acid may encode a fusion protein comprising a membrane binding domain.

The modified enzyme may be expressed at the desired levels in a host organism is using an expression vector. An expression vector comprising a modified enzyme nucleic acid can be any vector capable of expressing the gene encoding the modified enzyme nucleic acid in the selected host organism, and the choice of vector will depend on the host cell into which it is to be introduced. Thus, the vector can be an autonomously replicating vector, i.e. a vector that exists as an episomal entity, the replication of which is independent of chromosomal replication, such as, for example, a plasmid, a bacteriophage or an episomal element, a minichromosome or an artificial chromosome. Alternatively, the vector may be one which, when introduced into a host cell, is integrated into the host cell genome and replicated together with the chromosome.

The expression vector typically includes the components of a cloning vector, such as, for example, an element that permits autonomous replication of the vector in the selected host organism and one or more phenotypically detectable markers for selection purposes. The expression vector normally comprises control nucleotide sequences encoding a promoter, operator, ribosome binding site, translation initiation signal and optionally, a repressor gene or one or more activator genes. Additionally, the expression vector may comprise a sequence coding for an amino acid sequence capable of targeting the modified enzyme to a host cell organelle such as a peroxisome or to a particular host cell compartment. Such a targeting sequence includes but is not limited to the sequence SKL. For expression under the direction of control sequences, the nucleic acid sequence the modified enzyme is operably linked to the control sequences in proper manner with respect to expression.

Preferably, a polynucleotide in a vector is operably linked to a control sequence that is capable of providing for the expression of the coding sequence by the host cell, i.e. the vector is an expression vector. The control sequences may be modified, for example, by the addition of further transcriptional regulatory elements to make the level of transcription directed by the control sequences more responsive to transcriptional modulators. The control sequences may in particular comprise promoters.

In the vector, the nucleic acid sequence encoding for the modified enzyme is operably combined with a suitable promoter sequence. The promoter can be any DNA sequence having transcription activity in the host organism of choice and can be derived from genes that are homologous or heterologous to the host organism. Examples of suitable promoters for directing the transcription of the modified nucleotide sequence, such as modified enzyme nucleic acids, in a bacterial host include the promoter of the lac operon of *E. coli*, the *Streptomyces coelicolor* agarase gene dagA promoters, the promoters of the *Bacillus licheniformis* α-amylase gene (amyL), the aprE promoter of *Bacillus subtilis*, the promoters of the *Bacillus stearothermophilus* maltogenic amylase gene (amyM), the promoters of the *Bacillus amyloliquefaciens* α-amylase gene (amyQ), the promoters of the *Bacillus subtilis* xylA and xylB genes and a promoter derived from a *Lactococcus* sp.—derived promoter including the P170 promoter. When the gene encoding the modified enzyme is expressed in a bacterial species such as *E. coli*, a suitable promoter can be selected, for example, from a bacteriophage promoter including a T7 promoter and a phage lambda promoter. For transcription in a fungal species, examples of useful promoters are those derived from the genes encoding the, *Aspergillus oryzae* TAKA amylase, *Rhizomucor miehei* aspartic proteinase, *Aspergillus niger* neutral α-amylase, *A. niger* acid stable α-amylase, *A. niger* glucoamylase, *Rhizomucor miehei* lipase, *Aspergillus oryzae* alkaline protease, *Aspergillus oryzae* triose phosphate isomerase or *Aspergillus nidulans* acetamidase. Examples of suitable promoters for the expression in a yeast species include but are not limited to the Gal 1 and Gal 10 promoters of *Saccharomyces cerevisiae* and the *Pichia pastoris* AOX1 or AOX2 promoters.

Examples of suitable bacterial host organisms are gram positive bacterial species such as *Bacillaceae* including *Bacillus subtilis*, *Bacillus licheniformis*, *Bacillus lentus*, *Bacillus brevis*, *Bacillus stearothermophilus*, *Bacillus alkalophilus*, *Bacillus amyloliquefaciens*, *Bacillus coagulans*, *Bacillus lautus*, *Bacillus megaterium* and *Bacillus thuringiensis*, *Streptomyces* species such as *Streptomyces murinus*, lactic acid bacterial species including *Lactococcus* spp. such as *Lactococcus lactis*, *Lactobacillus* spp. including *Lactobacillus reuteri*, *Leuconostoc* spp., *Pediococcus* spp. and *Streptococcus* spp. Alternatively, strains of a gram-negative bacterial species belonging to *Enterobacteriaceae* including *E. coli*, or to *Pseudomonadaceae* can be selected as the host organism. A suitable yeast host organism can be selected from the biotechnologically relevant yeasts species such as but not limited to yeast species such as *Pichia* sp., *Hansenula* sp or *Kluyveromyces*, *Yarrowinia* species or a species of *Saccharomyces* including *Saccharomyces cerevisiae* or a species belonging to *Schizosaccharomyce* such as, for example, *S. Pombe* species. Preferably a strain of the methylotrophic yeast species *Pichia pastoris* is used as the host organism. Preferably the host organism is a *Hansenula* species. Suitable host organisms among filamentous fungi include species of *Aspergillus*, e.g. *Aspergillus niger*, *Aspergillus oryzae*, *Aspergillus tubigensis*, *Aspergillus awamori* or *Aspergillus nidulans*. Alternatively, strains of a *Fusarium* species, e.g. *Fusarium oxysporum* or of a *Rhizomucor* species such as *Rhizomucor miehei* can be used as the host organism. Other suitable strains include *Thermomyces* and *Mucor* species.

Host cells comprising polynucleotides may be used to express polypeptides, such as the modified enzymes disclosed herein, fragments, homologues, variants or derivatives thereof. Host cells may be cultured under suitable conditions which allow expression of the proteins. Expression of the polypeptides may be constitutive such that they are continually produced, or inducible, requiring a stimulus to initiate expression. In the case of inducible expression, protein production can be initiated when required by, for example, addition of an inducer substance to the culture medium, for example dexamethasone or IPTG. Polypeptides can be extracted from host cells by a variety of techniques known in the art, including enzymatic, chemical and/or osmotic lysis and physical disruption. Polypeptides may also be produced recombinantly in an in vitro cell-free system, such as the TnT™ (Promega) rabbit reticulocyte system.

In a third aspect, the invention is drawn to a method of modifying an enzyme comprising modifying a first site in the enzyme part of a structurally defined region so that the first site can bind to a second site. In a preferred embodiment, the first site is in a loop or sequence adjacent to a β-sheet. In a preferred embodiment, the second site is located in a β-sheet. In a preferred embodiment, the modified enzyme is a xylanase or Clan C.

In a preferred embodiment, the invention is drawn to a modified xylanase or a method of modifying a xylanase (or modified enzyme), according to at least one of the following: (i) modifying the N-terminal sequence so that the N-terminal region is bound by a disulphide bridge to an adjacent β-strand (see Gruber, et al., 1998 in *T. reesei* XynII the amino acids 1-4 and 24-30 respectively); (ii) modifying the C-terminal (in *T reesei* XynII amino acids 183-190, see Gruber, et al., 1998) so that it is bound to an adjacent β-strand; (iii) modifying an α-helix of the enzyme so that it can be bound more tightly to the body of the protein; (iv) modifying at least one adjacent loop so that it binds adjacent beta strand B6a (in *T. reesei* XynII amino acids 91-94, Gruber, et al., 1998) or (v) modifying residue as equivalent to XynII, as provided above.

As another embodiment, (per the examples) mutagenesis may be used to create disulphide bridges, salt bridges and separate point mutations at different regions. For example, the enzyme may be modified to create at least one disulphide bridge, so that at least one disulphide bridge may: 1) stabilize the N-terminal region or bind the N-terminal beta strand to the adjacent beta sheet (positions 2-28, 5-19, 7-16, 10-29 in XynII, or an equivalent position, as disclosed herein); 2) stabilize the alpha helix region (positions 105-162, 57-153, 110-151, 111-151, in XynII or an equivalent position as disclosed herein); 3) stabilize the C-terminal region (positions 63-188, 61-190, 36-186 or 34-188 in XynII, or an equivalent position as disclosed herein); or 4) stabilize the loop by binding to the beta strand such as B6b (92-144, 113-143 in XynII or an equivalent position as disclosed herein) and/or 5) stabilize the beta sheet (positions 26-38, 61-149, 63-147, 65-186, 67-184 in XynII, or an equivalent position, as provided herein).

Salt bridges may be created at different sites of the enzyme: (e.g., positions 22, 180, 58 or +191D in XynI, or an equivalent position, as provided herein) and single point mutations may be introduced at different sites of the molecule (e.g., positions 108, 26, 30, 67, 93, 97, 132, 157, 160, 165, 169 or 186 in XynII, or an equivalent position, as provided herein) thereby increasing the thermostability and/or thermophilicity and or alkalophilicity the protein. As with the Y5 mutant, the C-terminus may be bound more tightly to the body of the enzyme by adding as a recombinant change one amino acid (e.g. aspartic acid or glutamic acid) which then can form a salt bridge from the C-terminus to the body of the enzyme. If appropriate, a suitable amino acid replacement can be made in the body of the protein, so as to enable the formation of a salt bridge or to stabilize the enzyme in the C-terminal part via the α-helix or a region near the α-helix.

Additional mutants can be created according to this aspect of the invention. The structure of the N-terminal beta strand A1 or N-terminal loop in family 11 and 12 enzymes is described as the beta strand, a part of the beta sheet A prior to/up to a beta bend structure leading to beta strand B1 or the N-terminal loop prior to the first beta strand of the beta sheet. (see, Törrönen et al., Biochemistry 1995, 34, 847-856; Sandgren, et. al., J. Mol. Bio. (2001) 308, 295-310; Gruber, et al., 1998). The B1 beta strand of the N-terminal region is described as the beta strand part of the beta sheet B prior to/up to a beta bend structure leading to beta strand B2 or the loop prior to the first beta strand of the beta sheet. The is beta strand A1 region is bound preferably to beta strand A2 or to any other adjacent region (XynII or an equivalent thereof). The beta strand B1 region is bound preferably to beta strand B2 or to any other adjacent region (XynII or an equivalent thereof). In XynII A1 comprises residues 1-4, A2 residues 25-30, B1 residues 6-10 and B2 residues 13-19.

The structure of the C-terminal beta strand A4 or C-terminal loop in family 11 and 12 enzymes is the beta strand part of the beta sheet A between beta strands A3 and A5 or the loop as following beta sheet A4 (see Törrönen et al., Biochemistry 1995, 34, 847-856; Sandgren, et. al., J. Mol. Bio. (2001) 308, 295-310; Gruber, et al., 1998). The beta strand A4 region is bound preferably to beta strand A3 or A5, or to any other adjacent region. In XynII A4 is residues 183-190, A3 is residues 33-39 and A5 is residues 61-69. The cord of family 11 and 12 is described as the loop connecting beta strands B6b and B9. The beta strand of family 11 and 12 B6b is described as the beta strand prior to the cord (Törrönen et al., Biochemistry 1995, 34, 847-856; Sandgren, et. al., J. Mol. Bio. (2001) 308, 295-310; Gruber, et al., 1998). The beta strand B6b region may be bound to the cord or to the loop between beta strands A6 and B7, or to any other adjacent region. In XynII, B6b is residues 90-94 and B9 is residues 103-110, the cord is 95-102, beta strand A6 is residues 148-152, beta strand B7 is residues 134-142 and the loop between beta stands A6 and B7 is residues 143-147.

The helix of family 11 and 12 enzymes is described as region following beta strand A6 and forming a helical structure parallel to beta strand B9 (Törrönen et al., Biochemistry 1995, 34, 847-856; Sandgren, et. al., J. Mol.). The helix of family 11 and 12 enzymes is bound preferably to beta strand B9 or any other adjacent region. In XynII the helix is residues 153-162, beta strand A6 is residues 148-152 and beta strand B9 is residues 103-110.

EXAMPLES

Example 1

Plasmids Used for Xylanase II Expression and Mutagenesis Template

The open reading frame encoding *Trichoderma reesei* XYNII gene product was amplified by polymerase chain reaction (PCR) from the *T. reesei* cDNA library. XYNII cDNA was cloned into pKKtac (VTT, Espoo, Finland) or alternatively into pALK143 (ROAL, Rajamäki, Finland).

Example 2

Site-Directed Mutagenesis for Generation of Mutant of Xylanase II

Expression vectors containing cDNA-encoding xylanase II as described in Example 1 were used as template in the stepwise site-directed mutagenesis in consecutive PCR amplifications. Synthetic oligonucleotide primers containing the altered codons for the mutations X-Y were used for insertion of the desired alteration into the native xylanase II primary amino acid sequence. By this approach the residues of sites 92, 93 and 144 of the wild-type enzyme mutants were generated to bind the loop N143-S146 of xynII to the neighbouring β-strand. Additionally, mutagenesis was performed to generate the mutations at sites 22, 65, 97 and 108 into the xylanase primary sequence. The oligonucleotide sequences used in the mutagenesis are shown FIG. 3. PCR was carried out as described in the Quick Change Site-directed mutagenesis (Stratagene, La Jolla, Calif., USA) according to standard PCR procedures. PfuTurbo (Stratagene) was used as DNA polymerase to amplify plasmid DNA. Plasmid DNA from the site-directed mutagenesis PCR amplification was transformed to E. coli XL-1 blue and the transformed bacterial cells were then propagated on LB, with ampicillin 100 ug/ml for plasmid DNA selection and amplification of the mutated DNA. Plasmids were isolated and sequenced to confirm that they contain the desired mutations. The mutated plasmid DNA encoding the mutant variants was over-expressed in E. coli to examine the influence of the mutagenesis on the T. reesei xylanase Y5 mutants enzymatic properties.

Example 3

Production of the Modified XYNII Gene Products in E. coli Strain and Assay for Xylanase Activity E. coli strains over-expressing the mutated variants of the xylanase II were cultivated on plates supplemented with 1% birchwood xylan (Sigma, Steinheim, Germany) coupled with Rhemazol Brilliant Blue. Rhemazol Brilliant Blue coupled to xylan was utilized to detect xylanase activity that was readily visualized by a characteristic halo formation due to the blue colour disappearance around the bacterial colonies expressing xylanase activity (Biely et al., 1985).

The mutated xylanase genes (see above; Example 2) were expressed in E. coli at +37° C. in shake flasks in LB culture medium. Cell cultures expressing the enzyme variants is were centrifuged and the cell pellet separated from the supernatant harbouring the enzyme that was secreted from the cells into the culture medium. The xylanase enzyme activity assay was performed according to standard methods. The growth medium containing the secreted xylanase mutants were incubated for 10 min in 1% birchwood xylan (Sigma) at 50° C. in 50 mM citrate-phosphate buffer (ph 5.0-t) and 50 mM Tris-HCl at pH 7-9. (Bailey et al., 1992). If needed, heat inactivated growth medium was used to dilute the samples. The enzymatic activity of the mutant variants was examined in comparison to the wild type and the Y5 mutation enzyme at varying conditions (see, for Bailey et al, 1992).

Example 4

Determination of the Temperature Dependent Stability and pH Dependent Activity of the Xylanase II Mutants Activity as a Function of Temperature;

The xylanase activity of the mutant variants was determined at varying temperatures and selected pH values (see Figures herein). The mutants were incubated for 10 min with 1% birchwood xylan (Sigma) in 50 mM citrate-phosphate buffer (ph 4.5-7) or 50 mM Tris-HCl at pH 7-9. The relative amount of released reducing sugars was detected with the DNS method assay as described in example 3.

Residual Activity

The mutant variants were incubated for 10 minutes at varying temperatures without substrate. After the inactivation, the samples were cooled on ice and the residual activity was determined by DNS-method as described in example 3.

pH Dependent Activity

The pH-dependent xylanase activity was determined by detecting the enzyme activity at varying pH ranging from XX-YY for 10 min in 1% birchwood xylan at selected so temperatures (see pictures) in 50 mM citrate-phosphate buffer (ph 4.5-7) and 50 mM Tris-HCl at pH 7.5-9. This was followd by the DNS assay as described in example 3.

Example 5

Preparation and Testing of Mutant Xylanases for Improved Properties

Mutant xylanases were prepared having substitutions at one or more substitutions at different regions of the molecule. The substitutions were either separate point mutations in contact with other separate point mutations or they were prepared to act on a structural element found commonly in both family 11 and family 12 enzymes. The enzyme assays were performed as outlined in the examples. Examples of "structural" substitutions are disclosed herein and shown in the examples.

The disulphide bridge can be placed between sites 2 and 28 (T2C, T28C). FIG. 4 shows the importance of the N-terminal region in substituting residues of the wt for a more thermophilic variant. In a similar way removal of the native disulphide bridge (residues C4 and C32, Cel12A numbering) of T. reesei EGIII affects greatly the stability of the enzyme, as shown in the figures provided and tables herein (see, especially, Table A).

The region of the beta sheet common to both family 11 and 12 named beta strand B6b (as in Gruber et al), is shown to be of importance for stability, especially at alkali conditions. This effect is seen in the substitutions (as compared to the Y5 variant) as improved stability at pH 9 vs pH5 for P112, as shown in the figures (see, for example, FIG. 9, FIG. 10 and FIG. 11).

The importance of the region is clearly demonstrated by a different set of mutations (although in the same region) affecting the same beta strand. When sites 93, 97 and 144 are substituted (F93W, N97R, H144K, P9 in the graph), a similar effect in stabilization of the enzyme as when substituting the sites 92 and 144 (N92C, H144C=P12 in the graph) can be seen in the FIG. 9.

An example of the improved characteristics of separate substitutions at sites 22 and 180 is seen below. The variant containing the substitutions H22K and F180Q (P20 in FIG. 14) shows enhanced thermal stability over Y5 at pH 7.8.

Also the C-terminal region is of important for stability. In the substitution S65C, S186C (J21 in the graph) the enzyme shows improved activity with respect to temperature at pH 8.

One skilled in the art would readily appreciate that the present invention is well adapted to carry out the objects and obtain the ends and advantages mentioned, as well as those inherent therein. The molecular complexes and the methods, procedures, treatments, molecules specific compounds described herein are presently representative of preferred embodiments, are exemplary, and are not intended as limitations on the scope of the invention. It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

The invention claimed is:

1. A modified xylanase comprising a polypeptide having an amino acid sequence as set forth in SEQ ID NO:1, comprising amino acid substitutions at positions 2, 28, 58, and +191, further comprising at least one other substituted amino acid residue at a position selected from the group consisting of: 5, 7, 10, 11, 16, 19, 22, 26, 29, 30, 34, 36, 38, 57, 61, 63, 65, 67 92, 93, 97, 105, 108, 110, 111, 113, 132, 143, 144, 147, 149, 151, 153, 157, 160, 162, 165, 169, 180, 184, 186, 188, and 190, wherein the position of the substituted amino acid is numbered from the amino acid after the signal and pro sequence, wherein said modified xylanase has at least 90% sequence identity to SEQ ID NO:1 and has xylanase activity.

2. The xylanase according to claim 1, wherein the at least one other substitution is at residue 144.

3. The xylanase according to claim 2, wherein the substitution is H144C, or H144K.

4. The xylanase according to claim 3, wherein the xylanase has at least an additional substitution selected from the group consisting of: H22K, S65C, N92C, V108H, F93W, N97R, F180Q and S186C.

5. The xylanase according to claim 3, wherein the xylanase has the following mutations: H144C and N92C.

6. The xylanase according to claim 3, wherein the xylanase has the following mutations: F180Q, H144C and N92C.

7. The xylanase according to claim 3, wherein the xylanase has the following mutations: H22K, F180Q, H144C and N92C.

8. A modified family 11 xylanase comprising an amino acid sequence, the amino acid sequence having a substituted amino acid residue at a position equivalent to 144 in SEQ ID NO: 1, wherein the position of the substituted amino acid is numbered from the amino acid after the signal and pro sequence, wherein said modified xylanase has at least 90% sequence identity to SEQ ID NO:1 and has xylanase activity.

9. The xylanase according to claim 8, wherein the amino acid sequence has at least one further substituted amino acid residue at a position equivalent to a position selected from the group consisting of: 2, 22, 28, 58, 65, 92, 93, 97, 105, 108, 162, 180, 186 and +191.

10. The xylanase of claim 2, further comprising an additional substitution at a position selected from the group consisting of: 22, 65, 92, 93, 97, 105, 108, 144, 162, 180, and 186.

11. The xylanase of claim 8, further comprising at least one substituted amino acid residue at a position equivalent to a position selected from the group consisting of: 2, 5, 7, 10, 11, 16, 19, 22, 26, 28, 29, 30, 34, 36, 38, 57, 58, 61, 63, 65, 67, 92, 93, 97, 105, 108, 110, 111, 113, 132, 143, 147, 149, 151, 153, 157, 160, 162, 165, 169, 180, 184, 186, 188, 190 and +191.

12. The xylanase of claim 1, wherein the at least one other substitution is selected from the group consisting of H144C, H144K, H22K, S65C, N92C, V108H, F93W, N97R, F180Q and S186C.

13. The xylanase of claim 1, wherein the modified xylanase has increased thermostability or pH-stability at high pH with respect to the corresponding wild-type xylanase.

* * * * *